United States Patent
Hamner et al.

(10) Patent No.: US 11,596,785 B2
(45) Date of Patent: *Mar. 7, 2023

(54) SYSTEMS AND METHODS FOR PERIPHERAL NERVE STIMULATION IN THE FINGER OR HAND TO TREAT HAND TREMORS

(71) Applicant: Cala Health, Inc., Burlingame, CA (US)

(72) Inventors: Samuel Richard Hamner, San Francisco, CA (US); Kathryn H. Rosenbluth, San Francisco, CA (US); Serena HanYing Wong, Palo Alto, CA (US); Swaril Mathur, Laguna Niguel, CA (US); Paula Jean Chidester, Menlo Park, CA (US); Terence D. Sanger, Los Angeles, CA (US)

(73) Assignee: Cala Health, Inc., San Mateo, CA (US)

( * ) Notice: Subject to any disclaimer, the term of this patent is extended or adjusted under 35 U.S.C. 154(b) by 193 days.

This patent is subject to a terminal disclaimer.

(21) Appl. No.: 16/833,388

(22) Filed: Mar. 27, 2020

(65) Prior Publication Data
US 2020/0289814 A1  Sep. 17, 2020

Related U.S. Application Data

(63) Continuation of application No. 15/762,043, filed as application No. PCT/US2016/053513 on Sep. 23, 2016, now Pat. No. 10,603,482.
(Continued)

(51) Int. Cl.
*A61N 1/04* (2006.01)
*A61N 1/36* (2006.01)

(52) U.S. Cl.
CPC .......... *A61N 1/0456* (2013.01); *A61N 1/048* (2013.01); *A61N 1/0484* (2013.01); *A61N 1/36003* (2013.01); *A61N 1/36031* (2017.08)

(58) Field of Classification Search
None
See application file for complete search history.

(56) References Cited

U.S. PATENT DOCUMENTS

| | | |
|---|---|---|
| 3,204,637 A | 9/1965 | Frank et al. |
| 3,870,051 A | 3/1975 | Brindley |
| | (Continued) | |

FOREIGN PATENT DOCUMENTS

| | | |
|---|---|---|
| AU | 2019/250222 | 6/2021 |
| AU | 2017211048 | 3/2022 |
| | (Continued) | |

OTHER PUBLICATIONS

APARTIS; Clinical neurophysiology in movement disorders. Handb Clin Neurol; 111; Pediatric Neurology Pt. 1; pp. 87-92;Apr. 2013.
(Continued)

*Primary Examiner* — Michael W Kahelin
(74) *Attorney, Agent, or Firm* — Knobbe Martens Olson & Bear LLP

(57) ABSTRACT

Systems, devices, and methods for stimulating peripheral nerves in the fingers or hand to treat tremor are described. For example, a wearable ring device for delivering electrical stimulation to sensory nerves in a patient's finger can include an annular ring having a plurality of electrodes and a detachable unit having a power source and a pulse generator.

21 Claims, 23 Drawing Sheets

Related U.S. Application Data

(60) Provisional application No. 62/251,617, filed on Nov. 5, 2015, provisional application No. 62/222,210, filed on Sep. 23, 2015.

(56) References Cited

U.S. PATENT DOCUMENTS

| | | |
|---|---|---|
| 4,300,575 A | 11/1981 | Wilson |
| 4,458,696 A | 7/1984 | Larimore |
| 4,461,075 A | 7/1984 | Bailey |
| 4,539,996 A | 9/1985 | Engel |
| 4,569,351 A | 2/1986 | Tang |
| 4,582,049 A | 4/1986 | Ylvisaker |
| 4,729,377 A | 3/1988 | Granek et al. |
| 4,739,764 A | 4/1988 | Lue et al. |
| 4,763,659 A | 8/1988 | Dunseath, Jr. |
| 4,771,779 A | 9/1988 | Tanagho et al. |
| 4,981,146 A | 1/1991 | Bertolucci |
| 4,982,432 A | 1/1991 | Clark et al. |
| 5,003,978 A | 4/1991 | Dunseath, Jr. |
| 5,052,391 A | 10/1991 | Silverstone et al. |
| 5,070,862 A | 12/1991 | Berlant |
| 5,137,507 A | 8/1992 | Park |
| 5,330,516 A | 7/1994 | Nathan |
| 5,397,338 A | 3/1995 | Grey et al. |
| 5,514,175 A | 5/1996 | Kim et al. |
| 5,540,235 A | 7/1996 | Wilson |
| 5,562,707 A | 10/1996 | Prochazka et al. |
| 5,562,717 A | 10/1996 | Tippey et al. |
| 5,573,011 A | 11/1996 | Felsing |
| 5,575,294 A | 11/1996 | Perry et al. |
| 5,606,968 A | 3/1997 | Mang |
| 5,643,173 A | 7/1997 | Welles |
| 5,775,331 A | 7/1998 | Raymond et al. |
| 5,833,709 A | 11/1998 | Rise et al. |
| 5,833,716 A | 11/1998 | Bar-Or et al. |
| 5,899,922 A | 5/1999 | Loos |
| 6,016,449 A | 1/2000 | Fischell et al. |
| 6,076,018 A * | 6/2000 | Sturman ............ A61N 1/378 607/2 |
| 6,081,744 A | 6/2000 | Loos |
| 6,161,044 A | 12/2000 | Silverstone |
| 6,178,352 B1 | 1/2001 | Gruzdowich et al. |
| 6,351,674 B2 | 2/2002 | Silverstone |
| 6,366,813 B1 | 4/2002 | DiLorenzo |
| 6,445,955 B1 | 9/2002 | Michelson et al. |
| 6,449,512 B1 | 9/2002 | Boveja |
| 6,505,074 B2 | 1/2003 | Boveja et al. |
| 6,546,290 B1 | 4/2003 | Shloznikov |
| 6,564,103 B2 | 5/2003 | Fischer et al. |
| 6,579,270 B2 | 6/2003 | Sussman et al. |
| 6,652,449 B1 | 11/2003 | Gross et al. |
| 6,701,185 B2 | 3/2004 | Burnett et al. |
| 6,704,603 B1 | 3/2004 | Gesotti |
| 6,731,987 B1 | 5/2004 | McAdams et al. |
| 6,735,474 B1 | 5/2004 | Loeb et al. |
| 6,735,480 B2 | 5/2004 | Giuntoli et al. |
| 6,788,976 B2 | 9/2004 | Gesotti |
| 6,819,956 B2 | 11/2004 | DiLorenzo |
| 6,829,510 B2 | 12/2004 | Nathan et al. |
| 6,836,684 B1 | 12/2004 | Rijkhoff et al. |
| 6,862,480 B2 | 3/2005 | Cohen et al. |
| 6,892,098 B2 | 5/2005 | Ayal et al. |
| 6,937,905 B2 | 8/2005 | Carroll et al. |
| 6,959,215 B2 | 10/2005 | Gliner et al. |
| 6,959,216 B2 | 10/2005 | Faghri |
| 6,988,005 B2 | 1/2006 | McGraw et al. |
| 7,010,352 B2 | 3/2006 | Hogan |
| 7,089,061 B2 | 8/2006 | Grey |
| 7,146,220 B2 | 12/2006 | Dar et al. |
| 7,162,305 B2 | 1/2007 | Tong et al. |
| 7,171,266 B2 | 1/2007 | Gruzdowich et al. |
| 7,177,694 B2 | 2/2007 | Elbaum |
| 7,177,703 B2 | 2/2007 | Boveja et al. |
| 7,209,787 B2 | 4/2007 | DiLorenzo |
| 7,228,178 B2 | 6/2007 | Carroll et al. |
| 7,231,254 B2 | 6/2007 | DiLorenzo |
| 7,236,830 B2 | 6/2007 | Gliner |
| 7,254,444 B2 | 8/2007 | Moore et al. |
| 7,277,758 B2 | 10/2007 | DiLorenzo |
| 7,324,851 B1 | 1/2008 | DiLorenzo |
| 7,326,235 B2 | 2/2008 | Edwards |
| 7,328,068 B2 | 2/2008 | Spinelli et al. |
| 7,349,739 B2 | 3/2008 | Harry et al. |
| 7,353,064 B2 | 4/2008 | Gliner et al. |
| 7,369,896 B2 | 5/2008 | Gesotti |
| 7,499,747 B2 | 3/2009 | Kieval et al. |
| 7,529,582 B1 | 5/2009 | DiLorenzo |
| 7,558,610 B1 | 7/2009 | Odderson |
| 7,636,602 B2 | 12/2009 | Baru Fassio et al. |
| 7,643,880 B2 | 1/2010 | Tanagho et al. |
| 7,643,882 B2 | 1/2010 | Boston |
| 7,647,112 B2 | 1/2010 | Tracey et al. |
| 7,650,190 B2 | 1/2010 | Zhou et al. |
| 7,742,820 B2 | 6/2010 | Wyler et al. |
| 7,761,166 B2 | 7/2010 | Giftakis et al. |
| 7,769,464 B2 | 8/2010 | Gerber et al. |
| 7,857,771 B2 | 12/2010 | Alwan et al. |
| 7,899,527 B2 | 3/2011 | Yun et al. |
| 7,899,556 B2 | 3/2011 | Nathan et al. |
| 7,917,201 B2 | 3/2011 | Gozani et al. |
| 7,930,034 B2 | 4/2011 | Gerber |
| 7,949,403 B2 | 5/2011 | Palermo et al. |
| 7,957,814 B2 | 6/2011 | Goetz et al. |
| 7,974,696 B1 | 7/2011 | DiLorenzo |
| 7,974,698 B2 | 7/2011 | Tass et al. |
| 7,991,476 B2 | 8/2011 | Nachum |
| 7,996,088 B2 | 8/2011 | Marrosu et al. |
| 7,998,092 B2 | 8/2011 | Avni et al. |
| 8,000,796 B2 | 8/2011 | Tass et al. |
| 8,025,632 B2 | 9/2011 | Einarsson |
| 8,046,083 B2 | 10/2011 | Tegenthoff et al. |
| 8,075,499 B2 | 12/2011 | Nathan et al. |
| 8,086,318 B2 | 12/2011 | Strother et al. |
| 8,121,694 B2 | 2/2012 | Molnar et al. |
| 8,145,316 B2 | 3/2012 | Deem et al. |
| 8,165,668 B2 | 4/2012 | Dacey, Jr. et al. |
| 8,165,685 B1 | 4/2012 | Knutson et al. |
| 8,170,658 B2 | 5/2012 | Dacey, Jr. et al. |
| 8,175,718 B2 | 5/2012 | Wahlgren et al. |
| 8,187,209 B1 | 5/2012 | Guiffrida et al. |
| 8,195,287 B2 | 6/2012 | Dacey, Jr. et al. |
| 8,209,036 B2 | 6/2012 | Nathan et al. |
| 8,219,188 B2 | 7/2012 | Craig |
| 8,233,988 B2 | 7/2012 | Errico et al. |
| 8,260,439 B2 | 9/2012 | Diubaldi et al. |
| 8,265,763 B2 | 9/2012 | Fahey |
| 8,301,215 B2 | 10/2012 | Lee |
| 8,306,624 B2 | 11/2012 | Gerber et al. |
| 8,308,665 B2 | 11/2012 | Harry et al. |
| 8,313,443 B2 | 11/2012 | Tom |
| 8,326,432 B2 | 12/2012 | Kalisek |
| 8,343,026 B2 | 1/2013 | Gardiner et al. |
| 8,364,257 B2 | 1/2013 | Van Den Eerenbeemd et al. |
| 8,374,701 B2 | 2/2013 | Hyde et al. |
| 8,380,314 B2 | 2/2013 | Panken et al. |
| 8,382,688 B2 | 2/2013 | Dar et al. |
| 8,391,970 B2 | 3/2013 | Tracey et al. |
| 8,396,556 B2 | 3/2013 | Libbus et al. |
| 8,409,116 B2 | 4/2013 | Wang et al. |
| 8,412,338 B2 | 4/2013 | Faltys |
| 8,414,507 B2 | 4/2013 | Asada |
| 8,417,351 B2 | 4/2013 | Kilger |
| 8,428,719 B2 | 4/2013 | Napadow |
| 8,430,805 B2 | 4/2013 | Burnett et al. |
| 8,435,166 B2 | 5/2013 | Burnett et al. |
| 8,447,411 B2 | 5/2013 | Skelton et al. |
| 8,452,410 B2 | 5/2013 | Emborg et al. |
| 8,463,374 B2 | 6/2013 | Hudson et al. |
| 8,473,064 B2 | 6/2013 | Castel et al. |
| 8,548,594 B2 | 10/2013 | Thimineur et al. |
| 8,571,687 B2 | 10/2013 | Libbus et al. |
| 8,581,731 B2 | 11/2013 | Purks et al. |
| 8,583,238 B1 | 11/2013 | Heldman et al. |

(56) References Cited

U.S. PATENT DOCUMENTS

| | | |
|---|---|---|
| 8,588,884 B2 | 11/2013 | Hegde et al. |
| 8,588,917 B2 | 11/2013 | Whitehurst et al. |
| 8,608,671 B2 | 12/2013 | Kinoshita et al. |
| 8,626,305 B2 | 1/2014 | Nielsen et al. |
| 8,639,342 B2 | 1/2014 | Possover |
| 8,644,904 B2 | 2/2014 | Chang et al. |
| 8,644,938 B2 | 2/2014 | Craggs |
| 8,660,656 B2 | 2/2014 | Moser et al. |
| 8,666,496 B2 | 3/2014 | Simon et al. |
| 8,679,038 B1 | 3/2014 | Giuffrida |
| 8,682,441 B2 | 3/2014 | De Ridder |
| 8,688,220 B2 | 4/2014 | Degiorgio et al. |
| 8,694,104 B2 | 4/2014 | Libbus et al. |
| 8,694,110 B2 | 4/2014 | Nathan et al. |
| 8,702,584 B2 | 4/2014 | Rigaux et al. |
| 8,702,629 B2 | 4/2014 | Giuffrida et al. |
| 8,706,241 B2 | 4/2014 | Firlik et al. |
| 8,718,780 B2 | 5/2014 | Lee |
| 8,738,143 B2 | 5/2014 | Tucker et al. |
| 8,740,825 B2 | 6/2014 | Ehrenreich et al. |
| 8,744,587 B2 | 6/2014 | Miesel et al. |
| 8,755,892 B2 | 6/2014 | Amurthur et al. |
| 8,768,452 B2 | 7/2014 | Gerber |
| 8,788,045 B2 | 7/2014 | Gross et al. |
| 8,788,049 B2 | 7/2014 | Lasko et al. |
| 8,792,977 B2 | 7/2014 | Kakei et al. |
| 8,798,698 B2 | 8/2014 | Kim et al. |
| 8,821,416 B2 | 9/2014 | Johansson et al. |
| 8,825,163 B2 | 9/2014 | Grill et al. |
| 8,825,165 B2 | 9/2014 | Possover |
| 8,843,201 B1 | 9/2014 | Heldman et al. |
| 8,845,494 B2 | 9/2014 | Whitall et al. |
| 8,845,557 B1 | 9/2014 | Giuffrida et al. |
| 8,855,775 B2 | 10/2014 | Leyde |
| 8,862,238 B2 | 10/2014 | Rahimi et al. |
| 8,862,247 B2 | 10/2014 | Schoendorf et al. |
| 8,868,177 B2 | 10/2014 | Simon et al. |
| 8,874,227 B2 | 10/2014 | Simon et al. |
| 8,880,175 B2 | 11/2014 | Simon |
| 8,886,321 B2 | 11/2014 | Rohrer et al. |
| 8,892,200 B2 | 11/2014 | Wagner et al. |
| 8,897,870 B2 | 11/2014 | De Ridder |
| 8,903,494 B2 | 12/2014 | Goldwasser et al. |
| 8,920,345 B2 | 12/2014 | Greenberg et al. |
| 8,923,970 B2 | 12/2014 | Bar-Yoseph et al. |
| 8,948,876 B2 | 2/2015 | Gozani et al. |
| 8,961,439 B2 | 2/2015 | Yang et al. |
| 8,972,017 B2 | 3/2015 | Dar et al. |
| 8,989,861 B2 | 3/2015 | Su et al. |
| 9,002,477 B2 | 4/2015 | Burnett |
| 9,005,102 B2 | 4/2015 | Burnett et al. |
| 9,008,781 B2 | 4/2015 | Ahmed |
| 9,011,310 B2 | 4/2015 | Ahmed |
| 9,017,273 B2 | 4/2015 | Burbank et al. |
| 9,026,216 B2 | 5/2015 | Rossi et al. |
| 9,042,988 B2 | 5/2015 | Dilorenzo |
| 9,060,747 B2 | 6/2015 | Salorio |
| 9,089,691 B2 | 7/2015 | Libbus et al. |
| 9,095,351 B2 | 8/2015 | Sachs et al. |
| 9,095,417 B2 | 8/2015 | Dar et al. |
| 9,107,614 B2 | 8/2015 | Halkias et al. |
| 9,119,964 B2 | 9/2015 | Marnfeldt |
| 9,155,885 B2 | 10/2015 | Wei et al. |
| 9,155,890 B2 | 10/2015 | Guntinas-Lichius et al. |
| 9,162,059 B1 | 10/2015 | Lindenthaler |
| 9,168,374 B2 | 10/2015 | Su |
| 9,174,045 B2 | 11/2015 | Simon et al. |
| 9,186,095 B2 | 11/2015 | Machado et al. |
| 9,192,763 B2 | 11/2015 | Gerber et al. |
| 9,220,431 B2 | 12/2015 | Holzhacker |
| 9,220,895 B2 | 12/2015 | Siff et al. |
| 9,227,056 B1 | 1/2016 | Heldman et al. |
| 9,238,137 B2 | 1/2016 | Einav et al. |
| 9,238,142 B2 | 1/2016 | Heldman et al. |
| 9,242,085 B2 | 1/2016 | Hershey et al. |
| 9,248,285 B2 | 2/2016 | Haessler |
| 9,248,286 B2 | 2/2016 | Simon et al. |
| 9,248,297 B2 | 2/2016 | Hoyer et al. |
| 9,254,382 B2 | 2/2016 | Ahmad et al. |
| 9,259,577 B2 | 2/2016 | Kaula et al. |
| 9,265,927 B2 | 2/2016 | Yonce et al. |
| 9,282,928 B1 | 3/2016 | Giffrida |
| 9,289,607 B2 | 3/2016 | Su et al. |
| 9,301,712 B2 | 4/2016 | McNames et al. |
| 9,302,046 B1 | 4/2016 | Giuffrida et al. |
| 9,311,686 B2 | 4/2016 | Roush et al. |
| 9,314,190 B1 | 4/2016 | Giuffrida et al. |
| 9,314,622 B2 | 4/2016 | Embrey et al. |
| 9,332,918 B1 | 5/2016 | Buckley et al. |
| 9,339,213 B2 | 5/2016 | Otsamo et al. |
| 9,339,641 B2 | 5/2016 | Rajguru et al. |
| 9,345,872 B2 | 5/2016 | Groteke |
| 9,364,657 B2 | 6/2016 | Kiani et al. |
| 9,364,672 B2 | 6/2016 | Marnfeldt |
| 9,375,570 B2 | 6/2016 | Kiani et al. |
| 9,387,338 B2 | 7/2016 | Burnett |
| 9,393,430 B2 | 7/2016 | Demers et al. |
| 9,408,683 B2 | 8/2016 | St. Anne et al. |
| 9,414,776 B2 | 8/2016 | Sillay et al. |
| 9,415,205 B2 | 8/2016 | Lasko et al. |
| 9,452,287 B2 | 9/2016 | Rosenbluth et al. |
| 9,468,753 B2 | 10/2016 | Fisher et al. |
| 9,474,898 B2 | 10/2016 | Gozani et al. |
| 9,549,872 B2 | 1/2017 | Chen et al. |
| 9,586,038 B1 | 3/2017 | Kosierkiewicz |
| 9,597,509 B2 | 3/2017 | Hoffer et al. |
| 9,610,442 B2 | 4/2017 | Yoo et al. |
| 9,610,459 B2 | 4/2017 | Burnett et al. |
| 9,615,797 B2 | 4/2017 | John |
| 9,630,004 B2 | 4/2017 | Rajguru et al. |
| 9,649,486 B2 | 5/2017 | Holzhacker |
| 9,656,070 B2 | 5/2017 | Gozani |
| 9,669,211 B2 | 6/2017 | Wijting et al. |
| 9,675,800 B2 | 6/2017 | Li et al. |
| 9,675,801 B2 | 6/2017 | Kong et al. |
| 9,707,393 B2 | 7/2017 | Hsueh et al. |
| 9,731,126 B2 | 8/2017 | Ferree et al. |
| 9,757,584 B2 | 9/2017 | Burnett |
| 9,782,584 B2 | 10/2017 | Cartledge et al. |
| 9,861,283 B1 | 1/2018 | Giuffrida |
| 9,877,679 B1 | 1/2018 | Giuffrida |
| 9,877,680 B1 | 1/2018 | Giuffrida et al. |
| 9,884,179 B2 | 2/2018 | Bouton et al. |
| 9,924,899 B2 | 3/2018 | Pracar et al. |
| 9,956,395 B2 | 5/2018 | Bikson et al. |
| 9,974,478 B1 | 5/2018 | Brokaw et al. |
| 9,980,659 B2 | 5/2018 | Sadeghian-Motahar et al. |
| 10,004,900 B2 | 6/2018 | Kent et al. |
| 10,016,600 B2 | 7/2018 | Creasey et al. |
| 10,022,545 B1 | 7/2018 | Giuffrida |
| 10,028,695 B2 | 7/2018 | Machado et al. |
| 10,045,740 B2 | 8/2018 | John |
| 10,046,161 B2 | 8/2018 | Biasiucci et al. |
| 10,076,656 B2 | 9/2018 | Dar et al. |
| 10,080,885 B2 | 9/2018 | Nathan et al. |
| 10,112,040 B2 | 10/2018 | Herb et al. |
| 10,118,035 B2 | 11/2018 | Perez et al. |
| 10,130,809 B2 | 11/2018 | Cartledge et al. |
| 10,130,810 B2 | 11/2018 | Ferree et al. |
| 10,137,025 B2 | 11/2018 | Fior et al. |
| 10,173,060 B2 | 1/2019 | Wong et al. |
| 10,179,238 B2 | 1/2019 | Wong et al. |
| 10,213,593 B2 | 2/2019 | Kaplan et al. |
| 10,213,602 B2 | 2/2019 | Ironi et al. |
| 10,232,174 B2 | 3/2019 | Simon et al. |
| 10,252,053 B2 | 4/2019 | Page et al. |
| 10,286,210 B2 | 5/2019 | Yoo et al. |
| 10,293,159 B2 | 5/2019 | Kong et al. |
| 10,335,594 B2 | 7/2019 | Lin et al. |
| 10,335,595 B2 | 7/2019 | Ferree et al. |
| 10,342,977 B2 | 7/2019 | Raghunathan |
| 10,398,896 B2 | 9/2019 | Lin et al. |
| 10,456,573 B1 | 10/2019 | Feinstein et al. |
| 10,463,854 B2 | 11/2019 | Perez |

(56) References Cited

U.S. PATENT DOCUMENTS

| | | |
|---|---|---|
| 10,500,396 B2 | 12/2019 | Tamaki et al. |
| 10,537,732 B2 | 1/2020 | Nachum et al. |
| 10,549,093 B2 | 2/2020 | Wong et al. |
| 10,556,107 B2 | 2/2020 | Yoo et al. |
| 10,561,839 B2 | 2/2020 | Wong et al. |
| 10,603,482 B2 | 3/2020 | Hamner et al. |
| 10,610,114 B2 | 4/2020 | Buckley et al. |
| 10,625,074 B2 | 4/2020 | Rosenbluth et al. |
| 10,632,312 B2 | 4/2020 | Ziv |
| 10,661,082 B2 | 5/2020 | Kerselaers |
| 10,722,709 B2 | 7/2020 | Yoo et al. |
| 10,765,856 B2 | 9/2020 | Wong et al. |
| 10,773,079 B2 | 9/2020 | Keller et al. |
| 10,780,269 B2 | 9/2020 | Gozani et al. |
| 10,786,669 B2 | 9/2020 | Rajguru et al. |
| 10,814,130 B2 | 10/2020 | Wong et al. |
| 10,814,131 B2 | 10/2020 | Goldwasser et al. |
| 10,835,736 B2 | 11/2020 | Horter et al. |
| 10,850,090 B2 | 12/2020 | Rosenbluth et al. |
| 10,870,002 B2 | 12/2020 | Wybo et al. |
| 10,905,879 B2 | 2/2021 | Wong et al. |
| 10,918,853 B2 | 2/2021 | Creasey et al. |
| 10,940,311 B2 | 3/2021 | Gozani et al. |
| 10,945,879 B2 | 3/2021 | Black et al. |
| 10,960,207 B2 | 3/2021 | Wong et al. |
| 10,967,177 B2 | 4/2021 | Lee |
| 11,026,835 B2 | 6/2021 | Black et al. |
| 11,033,206 B2 | 6/2021 | Roh |
| 11,033,731 B2 | 6/2021 | Jeffery et al. |
| 11,033,736 B2 | 6/2021 | Edgerton et al. |
| 11,058,867 B2 | 7/2021 | Nathan et al. |
| 11,077,300 B2 | 8/2021 | McBride |
| 11,077,301 B2 | 8/2021 | Creasey et al. |
| 11,141,586 B2 | 10/2021 | Campean et al. |
| 11,141,587 B2 | 10/2021 | Campean et al. |
| 11,160,971 B2 | 11/2021 | Sharma et al. |
| 11,213,681 B2 | 1/2022 | Raghunathan |
| 11,224,742 B2 | 1/2022 | Burnett |
| 11,247,040 B2 | 2/2022 | Ferree et al. |
| 11,247,053 B2 | 2/2022 | Rajguru et al. |
| 11,266,836 B2 | 3/2022 | Charlesworth et al. |
| 11,331,480 B2 | 5/2022 | Hamner et al. |
| 11,344,722 B2 | 5/2022 | Wong et al. |
| 11,357,981 B2 | 6/2022 | Moaddeb et al. |
| 2001/0020177 A1 | 9/2001 | Gruzdowich |
| 2002/0161415 A1 | 10/2002 | Cohen et al. |
| 2002/0165586 A1 | 11/2002 | Hill et al. |
| 2002/0177882 A1 | 11/2002 | DiLorenzo |
| 2003/0032992 A1 | 2/2003 | Thacker et al. |
| 2003/0045922 A1 | 3/2003 | Northrop |
| 2003/0088294 A1 | 5/2003 | Gesotti |
| 2003/0093098 A1 | 5/2003 | Heitzmann et al. |
| 2003/0149457 A1 | 8/2003 | Tcheng et al. |
| 2003/0181959 A1 | 9/2003 | Dobak, III |
| 2003/0187483 A1 | 10/2003 | Grey et al. |
| 2003/0195583 A1 | 10/2003 | Gruzdowich et al. |
| 2004/0015094 A1 | 1/2004 | Manabe et al. |
| 2004/0088025 A1 | 5/2004 | Gesotti |
| 2004/0093093 A1 | 5/2004 | Andrews |
| 2004/0127939 A1* | 7/2004 | Grey ............... A61N 1/36014 606/204 |
| 2004/0133249 A1 | 7/2004 | Gesotti |
| 2004/0167588 A1 | 8/2004 | Bertolucci |
| 2004/0249416 A1 | 12/2004 | Yun et al. |
| 2004/0267331 A1 | 12/2004 | Koeneman et al. |
| 2005/0021103 A1 | 1/2005 | DiLorenzo |
| 2005/0055063 A1 | 3/2005 | Loeb et al. |
| 2005/0065553 A1 | 3/2005 | Ben Ezra et al. |
| 2005/0075502 A1 | 4/2005 | Shafer |
| 2005/0171577 A1 | 8/2005 | Cohen et al. |
| 2005/0234309 A1 | 10/2005 | Klapper |
| 2005/0240241 A1 | 10/2005 | Yun et al. |
| 2006/0047326 A1 | 3/2006 | Wheeler |
| 2006/0052726 A1 | 3/2006 | Weisz et al. |
| 2006/0095088 A1 | 5/2006 | De Ridder |
| 2006/0161218 A1 | 7/2006 | Danilov |
| 2006/0173509 A1 | 8/2006 | Lee et al. |
| 2006/0184059 A1 | 8/2006 | Jadidi |
| 2006/0217781 A1 | 9/2006 | John |
| 2006/0224191 A1 | 10/2006 | DiLorenzo |
| 2006/0229678 A1 | 10/2006 | Lee |
| 2006/0253167 A1 | 11/2006 | Kurtz et al. |
| 2006/0276853 A1 | 12/2006 | Tass |
| 2006/0293723 A1 | 12/2006 | Whitehurst et al. |
| 2007/0027486 A1 | 2/2007 | Armstrong |
| 2007/0073361 A1 | 3/2007 | Goren et al. |
| 2007/0123951 A1 | 5/2007 | Boston |
| 2007/0123952 A1 | 5/2007 | Strother et al. |
| 2007/0142862 A1 | 6/2007 | DiLorenzo |
| 2007/0156179 A1 | 7/2007 | Karashurov |
| 2007/0156182 A1 | 7/2007 | Castel et al. |
| 2007/0156183 A1 | 7/2007 | Rhodes |
| 2007/0156200 A1 | 7/2007 | Kornet et al. |
| 2007/0173899 A1 | 7/2007 | Levin et al. |
| 2007/0173903 A1 | 7/2007 | Goren et al. |
| 2007/0203533 A1 | 8/2007 | Goren et al. |
| 2007/0207193 A1 | 9/2007 | Zasler et al. |
| 2007/0282228 A1 | 12/2007 | Einav et al. |
| 2008/0004672 A1 | 1/2008 | Dalal et al. |
| 2008/0009772 A1 | 1/2008 | Tyler et al. |
| 2008/0021505 A1 | 1/2008 | Hastings et al. |
| 2008/0027507 A1 | 1/2008 | Bijelic et al. |
| 2008/0033259 A1 | 2/2008 | Manto et al. |
| 2008/0033504 A1 | 2/2008 | Bertolucci |
| 2008/0051839 A1 | 2/2008 | Libbus et al. |
| 2008/0058773 A1 | 3/2008 | John |
| 2008/0058871 A1 | 3/2008 | Libbus et al. |
| 2008/0058893 A1 | 3/2008 | Noujokat |
| 2008/0147146 A1 | 6/2008 | Wahlgren et al. |
| 2008/0177398 A1 | 7/2008 | Gross et al. |
| 2008/0195007 A1 | 8/2008 | Podrazhansky et al. |
| 2008/0208288 A1 | 8/2008 | Gesotti |
| 2008/0216593 A1 | 9/2008 | Jacobsen et al. |
| 2008/0288016 A1 | 11/2008 | Amurthur et al. |
| 2008/0300449 A1 | 12/2008 | Gerber et al. |
| 2008/0312520 A1 | 12/2008 | Rowlandson et al. |
| 2009/0018609 A1 | 1/2009 | DiLorenzo |
| 2009/0076565 A1 | 3/2009 | Surwit |
| 2009/0105785 A1 | 4/2009 | Wei et al. |
| 2009/0112133 A1 | 4/2009 | Deisseroth et al. |
| 2009/0157138 A1 | 6/2009 | Errico et al. |
| 2009/0187121 A1 | 7/2009 | Evans |
| 2009/0216294 A1 | 8/2009 | Ewing et al. |
| 2009/0222053 A1 | 9/2009 | Gaunt et al. |
| 2009/0247910 A1 | 10/2009 | Klapper |
| 2009/0299435 A1 | 12/2009 | Gliner et al. |
| 2009/0318986 A1 | 12/2009 | Alo et al. |
| 2009/0326595 A1 | 12/2009 | Brockway et al. |
| 2009/0326607 A1 | 12/2009 | Castel et al. |
| 2010/0004715 A1 | 1/2010 | Fahey |
| 2010/0010381 A1 | 1/2010 | Skelton et al. |
| 2010/0010572 A1 | 1/2010 | Skelton et al. |
| 2010/0057154 A1 | 3/2010 | Dietrich et al. |
| 2010/0099963 A1 | 4/2010 | Kilger |
| 2010/0107657 A1 | 5/2010 | Vistakula |
| 2010/0125220 A1 | 5/2010 | Seong |
| 2010/0152817 A1 | 6/2010 | Gillbe |
| 2010/0174342 A1 | 7/2010 | Boston et al. |
| 2010/0222630 A1 | 9/2010 | Mangrum et al. |
| 2010/0227330 A1 | 9/2010 | Fink et al. |
| 2010/0249637 A1 | 9/2010 | Walter et al. |
| 2010/0292527 A1 | 11/2010 | Schneider et al. |
| 2010/0298905 A1 | 11/2010 | Simon |
| 2010/0324611 A1 | 12/2010 | Deming et al. |
| 2011/0009920 A1 | 1/2011 | Whitehurst et al. |
| 2011/0021899 A1 | 1/2011 | Arps et al. |
| 2011/0040204 A1 | 2/2011 | Ivorra et al. |
| 2011/0054358 A1 | 3/2011 | Kim et al. |
| 2011/0071590 A1 | 3/2011 | Mounaim et al. |
| 2011/0098780 A1 | 4/2011 | Graupe et al. |
| 2011/0118805 A1 | 5/2011 | Wei et al. |
| 2011/0125212 A1 | 5/2011 | Tyler |
| 2011/0137375 A1 | 6/2011 | McBride |
| 2011/0184489 A1 | 7/2011 | Nicolelis et al. |

(56) References Cited

U.S. PATENT DOCUMENTS

| | | |
|---|---|---|
| 2011/0202107 A1 | 8/2011 | Sunagawa et al. |
| 2011/0208444 A1 | 8/2011 | Solinky |
| 2011/0213278 A1 | 9/2011 | Horak et al. |
| 2011/0224571 A1 | 9/2011 | Pascual-Leone et al. |
| 2011/0230701 A1 | 9/2011 | Simon et al. |
| 2011/0245734 A1 | 10/2011 | Wagner et al. |
| 2011/0250297 A1 | 10/2011 | Gronsky et al. |
| 2011/0282412 A1 | 11/2011 | Glukhovsky et al. |
| 2011/0288615 A1 | 11/2011 | Armstrong et al. |
| 2011/0301663 A1 | 12/2011 | Wang et al. |
| 2012/0010492 A1 | 1/2012 | Thramann et al. |
| 2012/0053491 A1 | 3/2012 | Nathan et al. |
| 2012/0078319 A1 | 3/2012 | De Ridder |
| 2012/0088986 A1 | 4/2012 | David et al. |
| 2012/0092178 A1 | 4/2012 | Callsen et al. |
| 2012/0101326 A1 | 4/2012 | Simon et al. |
| 2012/0109013 A1 | 5/2012 | Everett et al. |
| 2012/0136410 A1 | 5/2012 | Rezai et al. |
| 2012/0158094 A1 | 6/2012 | Kramer et al. |
| 2012/0184801 A1 | 7/2012 | Simon et al. |
| 2012/0185020 A1 | 7/2012 | Simon et al. |
| 2012/0220812 A1 | 8/2012 | Mishelevich |
| 2012/0239112 A1 | 9/2012 | Muraoka |
| 2012/0245483 A1 | 9/2012 | Lundqvist |
| 2012/0259255 A1 | 10/2012 | Tomlinson et al. |
| 2012/0277621 A1 | 11/2012 | Gerber et al. |
| 2012/0302821 A1 | 11/2012 | Burnett |
| 2012/0310298 A1 | 12/2012 | Besio et al. |
| 2012/0310303 A1 | 12/2012 | Popovic et al. |
| 2012/0330182 A1 | 12/2012 | Alberts et al. |
| 2013/0006322 A1 | 1/2013 | Tai |
| 2013/0053817 A1 | 2/2013 | Yun et al. |
| 2013/0060124 A1 | 3/2013 | Zietsma |
| 2013/0066388 A1 | 3/2013 | Bernhard et al. |
| 2013/0066395 A1 | 3/2013 | Simon et al. |
| 2013/0085317 A1 | 4/2013 | Feinstein |
| 2013/0090519 A1 | 4/2013 | Tass |
| 2013/0116606 A1 | 5/2013 | Cordo |
| 2013/0123568 A1 | 5/2013 | Hamilton et al. |
| 2013/0123666 A1 | 5/2013 | Giuffrida et al. |
| 2013/0131484 A1 | 5/2013 | Pernu |
| 2013/0131770 A1 | 5/2013 | Rezai |
| 2013/0158624 A1 | 6/2013 | Bain et al. |
| 2013/0158627 A1 | 6/2013 | Gozani et al. |
| 2013/0211471 A1 | 8/2013 | Libbus et al. |
| 2013/0231713 A1 | 9/2013 | De Ridder et al. |
| 2013/0236867 A1 | 9/2013 | Avni et al. |
| 2013/0238049 A1 | 9/2013 | Simon et al. |
| 2013/0245486 A1 | 9/2013 | Simon et al. |
| 2013/0245713 A1 | 9/2013 | Tass |
| 2013/0253299 A1 | 9/2013 | Weber et al. |
| 2013/0267759 A1 | 10/2013 | Jin |
| 2013/0281890 A1 | 10/2013 | Mishelevich |
| 2013/0289647 A1 | 10/2013 | Bhadra et al. |
| 2013/0296967 A1 | 11/2013 | Skaribas et al. |
| 2013/0297022 A1 | 11/2013 | Pathak |
| 2013/0331907 A1 | 12/2013 | Sumners et al. |
| 2013/0333094 A1 | 12/2013 | Rogers et al. |
| 2013/0338726 A1 | 12/2013 | Machado |
| 2014/0025059 A1 | 1/2014 | Kerr |
| 2014/0031605 A1 | 1/2014 | Schneider |
| 2014/0039573 A1 | 2/2014 | Jindra |
| 2014/0039575 A1 | 2/2014 | Bradley |
| 2014/0046423 A1 | 2/2014 | Rajguru et al. |
| 2014/0058189 A1 | 2/2014 | Stubbeman |
| 2014/0067003 A1 | 3/2014 | Vase et al. |
| 2014/0078694 A1 | 3/2014 | Wissmar |
| 2014/0081345 A1 | 3/2014 | Hershey |
| 2014/0094675 A1 | 4/2014 | Luna et al. |
| 2014/0094873 A1 | 4/2014 | Emborg et al. |
| 2014/0128939 A1 | 5/2014 | Embrey et al. |
| 2014/0132410 A1 | 5/2014 | Chang |
| 2014/0142654 A1 | 5/2014 | Simon et al. |
| 2014/0148872 A1* | 5/2014 | Goldwasser ....... A61N 1/36034 607/45 |
| 2014/0148873 A1 | 5/2014 | Kirn |
| 2014/0163444 A1 | 6/2014 | Ingvarsson |
| 2014/0171834 A1 | 6/2014 | DeGoede et al. |
| 2014/0200573 A1 | 7/2014 | Deem et al. |
| 2014/0214119 A1 | 7/2014 | Greiner et al. |
| 2014/0228927 A1 | 8/2014 | Ahmad et al. |
| 2014/0236258 A1 | 8/2014 | Carroll et al. |
| 2014/0249452 A1 | 9/2014 | Marsh et al. |
| 2014/0257047 A1 | 9/2014 | Sillay et al. |
| 2014/0257129 A1 | 9/2014 | Choi et al. |
| 2014/0276194 A1 | 9/2014 | Osorio |
| 2014/0277220 A1 | 9/2014 | Brennan et al. |
| 2014/0296752 A1 | 10/2014 | Edgerton et al. |
| 2014/0296934 A1 | 10/2014 | Gozani et al. |
| 2014/0296935 A1 | 10/2014 | Ferree et al. |
| 2014/0300490 A1 | 10/2014 | Kotz et al. |
| 2014/0309709 A1 | 10/2014 | Gozanl et al. |
| 2014/0316484 A1 | 10/2014 | Edgerton et al. |
| 2014/0324118 A1 | 10/2014 | Simon et al. |
| 2014/0330068 A1 | 11/2014 | Partsch et al. |
| 2014/0330335 A1 | 11/2014 | Errico et al. |
| 2014/0336003 A1 | 11/2014 | Franz et al. |
| 2014/0336722 A1 | 11/2014 | Rocon De Lima et al. |
| 2014/0343462 A1 | 11/2014 | Burnet |
| 2014/0350436 A1 | 11/2014 | Nathan et al. |
| 2014/0358040 A1 | 12/2014 | Kim et al. |
| 2014/0364678 A1 | 12/2014 | Harry et al. |
| 2015/0004656 A1 | 1/2015 | Tang et al. |
| 2015/0005852 A1 | 1/2015 | Hershey et al. |
| 2015/0012067 A1 | 1/2015 | Bradley et al. |
| 2015/0038886 A1 | 2/2015 | Snow |
| 2015/0044656 A1 | 2/2015 | Eichhorn et al. |
| 2015/0057506 A1 | 2/2015 | Luna et al. |
| 2015/0073310 A1 | 3/2015 | Pracar et al. |
| 2015/0080979 A1 | 3/2015 | Lasko et al. |
| 2015/0100004 A1 | 4/2015 | Goldman et al. |
| 2015/0100104 A1 | 4/2015 | Kiani et al. |
| 2015/0100105 A1 | 4/2015 | Kiani et al. |
| 2015/0148866 A1 | 5/2015 | Bulsen et al. |
| 2015/0148878 A1 | 5/2015 | Yoo et al. |
| 2015/0157274 A1 | 6/2015 | Ghassemzadeh et al. |
| 2015/0164377 A1 | 6/2015 | Nathan et al. |
| 2015/0164401 A1 | 6/2015 | Toth et al. |
| 2015/0190085 A1 | 7/2015 | Nathan et al. |
| 2015/0190634 A1 | 7/2015 | Rezai et al. |
| 2015/0196767 A1 | 7/2015 | Zaghloul |
| 2015/0202444 A1 | 7/2015 | Franke et al. |
| 2015/0208955 A1 | 7/2015 | Smith |
| 2015/0216475 A1 | 8/2015 | Luna et al. |
| 2015/0230733 A1 | 8/2015 | Heo et al. |
| 2015/0230756 A1 | 8/2015 | Luna et al. |
| 2015/0277559 A1 | 10/2015 | Vescovi et al. |
| 2015/0335882 A1 | 11/2015 | Gross et al. |
| 2016/0001096 A1 | 1/2016 | Mishelevich |
| 2016/0008620 A1 | 1/2016 | Stubbeman |
| 2016/0016014 A1 | 1/2016 | Wagner et al. |
| 2016/0022987 A1 | 1/2016 | Zschaeck et al. |
| 2016/0022989 A1 | 1/2016 | Pfeifer |
| 2016/0038059 A1 | 2/2016 | Asada et al. |
| 2016/0045140 A1 | 2/2016 | Kitamura et al. |
| 2016/0089045 A1 | 3/2016 | Sadeghian-Motahar et al. |
| 2016/0106344 A1 | 4/2016 | Nazari |
| 2016/0121110 A1 | 5/2016 | Kent et al. |
| 2016/0128621 A1 | 5/2016 | Machado et al. |
| 2016/0129248 A1 | 5/2016 | Creasey et al. |
| 2016/0158542 A1 | 6/2016 | Ahmed |
| 2016/0158565 A1 | 6/2016 | Lee |
| 2016/0198998 A1 | 7/2016 | Rahimi et al. |
| 2016/0213924 A1 | 7/2016 | Coleman et al. |
| 2016/0220836 A1 | 8/2016 | Parks |
| 2016/0262685 A1 | 9/2016 | Wagner et al. |
| 2016/0263376 A1 | 9/2016 | Yoo et al. |
| 2016/0287879 A1 | 10/2016 | Denison et al. |
| 2016/0339239 A1 | 11/2016 | Yoo et al. |
| 2017/0014625 A1 | 1/2017 | Rosenbluth et al. |
| 2017/0027812 A1 | 2/2017 | Hyde et al. |
| 2017/0042467 A1 | 2/2017 | Herr et al. |
| 2017/0056238 A1 | 3/2017 | Yi et al. |
| 2017/0056643 A1 | 3/2017 | Herb et al. |

(56) References Cited

U.S. PATENT DOCUMENTS

| | | |
|---|---|---|
| 2017/0079597 A1 | 3/2017 | Horne |
| 2017/0080207 A1 | 3/2017 | Perez et al. |
| 2017/0132067 A1 | 8/2017 | Wong et al. |
| 2017/0266443 A1 | 9/2017 | Rajguru et al. |
| 2017/0274208 A1 | 9/2017 | Nagel et al. |
| 2017/0287146 A1 | 10/2017 | Pathak et al. |
| 2017/0312505 A1 | 11/2017 | Ahmed |
| 2017/0312512 A1 | 11/2017 | Creasey et al. |
| 2017/0361093 A1 | 12/2017 | Yoo et al. |
| 2018/0001086 A1 | 1/2018 | Bartholomew et al. |
| 2018/0042654 A1 | 2/2018 | Ingvarsson et al. |
| 2018/0049676 A1 | 2/2018 | Griffiths et al. |
| 2018/0064344 A1 | 3/2018 | Nguyen |
| 2018/0064362 A1 | 3/2018 | Hennings et al. |
| 2018/0064944 A1 | 3/2018 | Grill et al. |
| 2018/0132757 A1 | 5/2018 | Kong et al. |
| 2018/0140842 A1 | 5/2018 | Olaighin et al. |
| 2018/0168905 A1 | 6/2018 | Goodall et al. |
| 2018/0214694 A1 | 8/2018 | Parramon |
| 2018/0221620 A1 | 8/2018 | Metzger |
| 2018/0235500 A1 | 8/2018 | Lee et al. |
| 2018/0236217 A1 | 8/2018 | Hamner et al. |
| 2018/0345020 A1 | 12/2018 | Ironi et al. |
| 2019/0001117 A1 | 1/2019 | Ben-David et al. |
| 2019/0126047 A1 | 5/2019 | Kassiri Bidhendi et al. |
| 2019/0134393 A1 | 5/2019 | Wong et al. |
| 2019/0143098 A1 | 5/2019 | Kaplan et al. |
| 2019/0167976 A1 | 6/2019 | Byers et al. |
| 2019/0321636 A1 | 10/2019 | Law et al. |
| 2019/0374771 A1 | 12/2019 | Simon et al. |
| 2020/0023183 A1 | 1/2020 | Ollerenshaw et al. |
| 2020/0038654 A1 | 2/2020 | Doskocil et al. |
| 2020/0046968 A1 | 2/2020 | Herr et al. |
| 2020/0061378 A1 | 2/2020 | Ganguly et al. |
| 2020/0139118 A1 | 5/2020 | John et al. |
| 2020/0147373 A1 | 5/2020 | Tamaki et al. |
| 2020/0155847 A1 | 5/2020 | Perez |
| 2020/0171269 A1 | 6/2020 | Hooper et al. |
| 2020/0171304 A1 | 6/2020 | Simon et al. |
| 2020/0215324 A1 | 7/2020 | Mantovani et al. |
| 2020/0221975 A1 | 7/2020 | Basta et al. |
| 2020/0254247 A1 | 8/2020 | Brezel et al. |
| 2020/0269046 A1 | 8/2020 | Page et al. |
| 2020/0276442 A1 | 9/2020 | Owen |
| 2020/0282201 A1 | 9/2020 | Doskocil |
| 2020/0289813 A1 | 9/2020 | Ito et al. |
| 2020/0289814 A1 | 9/2020 | Hamner et al. |
| 2020/0297999 A1 | 9/2020 | Pal |
| 2020/0316379 A1 | 10/2020 | Yoo et al. |
| 2020/0324104 A1 | 10/2020 | Labuschagne et al. |
| 2020/0367775 A1 | 11/2020 | Buckley et al. |
| 2020/0405188 A1 | 12/2020 | Sharma et al. |
| 2020/0406022 A1 | 12/2020 | Sharma et al. |
| 2021/0016079 A1 | 1/2021 | Ekelem et al. |
| 2021/0031026 A1 | 2/2021 | Simon et al. |
| 2021/0031036 A1 | 2/2021 | Sharma et al. |
| 2021/0052897 A1 | 2/2021 | Bhadra et al. |
| 2021/0060337 A1 | 3/2021 | Wybo et al. |
| 2021/0069507 A1 | 3/2021 | Gozani et al. |
| 2021/0162212 A1 | 6/2021 | Kern et al. |
| 2021/0169684 A1 | 6/2021 | Black et al. |
| 2021/0187279 A1 | 6/2021 | Bouton et al. |
| 2021/0205619 A1 | 7/2021 | Wong et al. |
| 2021/0213283 A1 | 7/2021 | Yoo et al. |
| 2021/0220650 A1 | 7/2021 | Kassiri Bidhendi et al. |
| 2021/0244940 A1 | 8/2021 | Liberatore et al. |
| 2021/0244950 A1 | 8/2021 | Ironi et al. |
| 2021/0252278 A1 | 8/2021 | Hamner et al. |
| 2021/0260379 A1 | 8/2021 | Charlesworth et al. |
| 2021/0283400 A1 | 9/2021 | Hamner et al. |
| 2021/0289814 A1 | 9/2021 | Hamner et al. |
| 2021/0299445 A1 | 9/2021 | Rajguru et al. |
| 2021/0330547 A1 | 10/2021 | Moaddeb et al. |
| 2021/0353181 A1 | 11/2021 | Roh |
| 2021/0379374 A1 | 12/2021 | Hamner et al. |
| 2021/0379379 A1 | 12/2021 | Campean et al. |
| 2021/0402172 A1 | 12/2021 | Ross et al. |
| 2022/0001164 A1 | 1/2022 | Sharma et al. |
| 2022/0016413 A1 | 1/2022 | John et al. |
| 2022/0031245 A1 | 2/2022 | Bresler |
| 2022/0054820 A1 | 2/2022 | Turner |
| 2022/0054831 A1 | 2/2022 | McBride |
| 2022/0088373 A1 | 3/2022 | Burnett |
| 2022/0126095 A1 | 4/2022 | Rajguru et al. |
| 2022/0212007 A1 | 7/2022 | Rajguru et al. |
| 2022/0218991 A1 | 7/2022 | Moaddeb et al. |

FOREIGN PATENT DOCUMENTS

| | | |
|---|---|---|
| CN | 1135722 | 11/1996 |
| CN | 103517732 | 1/2014 |
| CN | 103889503 | 6/2014 |
| CN | 104144729 | 11/2014 |
| CN | 105142714 A | 12/2015 |
| CN | 108348746 | 10/2021 |
| CN | 108778411 | 6/2022 |
| DE | 102008042373 | 4/2010 |
| DE | 102009004011 | 7/2010 |
| EP | 0000759 | 2/1979 |
| EP | 0725665 | 1/1998 |
| EP | 1062988 | 12/2000 |
| EP | 1558333 | 5/2007 |
| EP | 1727591 | 4/2009 |
| EP | 2383014 | 11/2011 |
| EP | 2291115 | 9/2013 |
| EP | 2801389 | 11/2014 |
| EP | 3020448 | 5/2016 |
| EP | 2029222 | 3/2017 |
| EP | 2780073 | 9/2017 |
| EP | 1951365 | 10/2017 |
| EP | 3154627 | 4/2018 |
| EP | 2827771 | 5/2018 |
| EP | 3184143 | 7/2018 |
| EP | 3075412 | 12/2018 |
| EP | 3349712 | 7/2019 |
| EP | 3503960 | 3/2020 |
| EP | 3352846 | 7/2020 |
| EP | 3493874 | 8/2020 |
| EP | 3409200 | 9/2020 |
| EP | 3427793 | 11/2020 |
| EP | 3641876 | 4/2021 |
| EP | 3352843 | 6/2021 |
| EP | 3679979 | 6/2021 |
| EP | 3402404 | 7/2021 |
| EP | 3562541 | 7/2021 |
| EP | 3675795 | 8/2021 |
| EP | 3100765 | 1/2022 |
| ES | 2222819 | 3/2006 |
| ES | 2272137 | 6/2008 |
| GB | 2496449 | 5/2013 |
| JP | 2002-200178 | 7/2002 |
| JP | 2003-501207 | 1/2003 |
| JP | 2004-512104 | 4/2004 |
| JP | 2006-503658 | 2/2006 |
| JP | 2008-018235 | 1/2008 |
| JP | 2009-34328 | 2/2009 |
| JP | 2009-529352 | 8/2009 |
| JP | 2010-506618 | 3/2010 |
| JP | 2010-512926 | 4/2010 |
| JP | 2010-527256 | 8/2010 |
| JP | 2012-005596 | 1/2012 |
| JP | 2012-055650 | 3/2012 |
| JP | 2012-217565 | 11/2012 |
| JP | 2013-017609 | 1/2013 |
| JP | 2013-094305 | 5/2013 |
| JP | 54-39921 | 3/2014 |
| JP | 2016-511651 | 4/2016 |
| WO | WO 1994/000187 | 1/1994 |
| WO | WO 1994/017855 | 8/1994 |
| WO | WO 1996/032909 | 10/1996 |
| WO | WO 1998/043700 | 10/1998 |
| WO | WO 1999/019019 | 4/1999 |
| WO | WO 2000/015293 | 3/2000 |
| WO | WO 2002/017987 | 3/2002 |

(56) References Cited

FOREIGN PATENT DOCUMENTS

| | | |
|---|---|---|
| WO | WO 2002034327 | 5/2002 |
| WO | WO 2005/122894 | 12/2005 |
| WO | WO 2007/112092 | 10/2007 |
| WO | WO 2009/153730 | 12/2009 |
| WO | WO 2010/111321 | 9/2010 |
| WO | WO 2010/141155 | 12/2010 |
| WO | WO 2011/119224 | 9/2011 |
| WO | WO 2011/144883 | 11/2011 |
| WO | WO 2012/040243 | 3/2012 |
| WO | WO 2013/071307 | 5/2013 |
| WO | WO 2013/074809 | 5/2013 |
| WO | WO 2014/043757 | 3/2014 |
| WO | WO 2014/053041 | 4/2014 |
| WO | WO 2014/093964 | 6/2014 |
| WO | WO 2014/113813 | 7/2014 |
| WO | WO 2014/146082 | 9/2014 |
| WO | WO 2014/151431 | 9/2014 |
| WO | WO 2014/153201 | 9/2014 |
| WO | WO 2014/207512 | 12/2014 |
| WO | WO 2015/033152 | 3/2015 |
| WO | WO 2015/039206 | 3/2015 |
| WO | WO 2015/039244 | 3/2015 |
| WO | WO 2015/042365 | 3/2015 |
| WO | WO 2015/079319 | 6/2015 |
| WO | WO 2015/095880 | 6/2015 |
| WO | WO 2015/128090 | 9/2015 |
| WO | WO 2015/164706 | 10/2015 |
| WO | WO 2015/187712 | 12/2015 |
| WO | WO 2016/007093 | 1/2016 |
| WO | WO 2016/019250 | 2/2016 |
| WO | WO 2016/094728 | 6/2016 |
| WO | WO 2016/102958 | 6/2016 |
| WO | WO 2016/110804 | 7/2016 |
| WO | WO 2016/128985 | 8/2016 |
| WO | WO 2016/149751 | 9/2016 |
| WO | WO 2016/166281 | 10/2016 |
| WO | WO 2016/179407 | 11/2016 |
| WO | WO 2016/189422 | 12/2016 |
| WO | WO 2016/195587 | 12/2016 |
| WO | WO 2016/201366 | 12/2016 |
| WO | WO 2017/004021 | 1/2017 |
| WO | WO 2017/010930 | 1/2017 |
| WO | WO 2017/023864 | 2/2017 |
| WO | WO 2017/053847 | 3/2017 |
| WO | WO 2017/062994 | 4/2017 |
| WO | WO 2017/086798 | 5/2017 |
| WO | WO 2017/088573 | 6/2017 |
| WO | WO 2017/132067 | 8/2017 |
| WO | WO 2017/199026 | 11/2017 |
| WO | WO 2017/208167 | 12/2017 |
| WO | WO 2017/209673 | 12/2017 |
| WO | WO 2017/210729 | 12/2017 |
| WO | WO 2017/221037 | 12/2017 |
| WO | WO 2018/009680 | 1/2018 |
| WO | WO 2018/028170 | 2/2018 |
| WO | WO 2018/028220 | 2/2018 |
| WO | WO 2018/028221 | 2/2018 |
| WO | WO 2018/039458 | 3/2018 |
| WO | WO 2018/093765 | 5/2018 |
| WO | WO 2018/112164 | 6/2018 |
| WO | WO 2018/187241 | 10/2018 |
| WO | WO 2019/005774 | 1/2019 |
| WO | WO 2019/014250 | 1/2019 |
| WO | WO 2019/028000 | 2/2019 |
| WO | WO 2019/082180 | 6/2019 |
| WO | WO 2019/143790 | 7/2019 |
| WO | WO 2019/169240 | 9/2019 |
| WO | WO 2019/202489 | 10/2019 |
| WO | WO 2019/213433 | 11/2019 |
| WO | WO 2020/006048 | 1/2020 |
| WO | WO 2020/068830 | 4/2020 |
| WO | WO 2020/069219 | 4/2020 |
| WO | WO 2020/086726 | 4/2020 |
| WO | WO 2020/131857 | 6/2020 |
| WO | WO 2020/185601 | 9/2020 |
| WO | WO 2021/005584 | 1/2021 |
| WO | WO 2021/055716 | 3/2021 |
| WO | WO 2021/062345 | 4/2021 |
| WO | WO 2021/127422 | 6/2021 |
| WO | WO 2021/228128 | 11/2021 |
| WO | WO 2021/252292 | 12/2021 |

OTHER PUBLICATIONS

Barbaud et al.; Improvement in essential tremor after pure sensory stroke due to thalamic infarction; European neurology; 46; pp. 57-59; Jul. 2001.

Barrios et al.: BCI algorithms for tremor identification, characterization and tracking; Seventh Framework Programme, EU; Contract No. FP7-ICT-2007-224051 (v3.0); 57 pgs.; Jul. 10, 2011.

Bartley et al.; Neuromodulation for overactive bladder; Nature Reviews Urology; 10; pp. 513-521; Sep. 2013.

Benabid et al.; A putative generalized model of the effects and mechanism of action of high frequency electrical stimulation of the central nervous system; Acta Neural Belg; 105(3); pp. 149-157; Sep. 2005.

Bergquist et al.: Motor unit recruitment when neuromuscular electrical stimulation is applied over a nerve trunk compared with a muscle belly: quadriceps femoris, Journal of Applied Physiology; vol. 113, No. 1, pp. 78-89; Jul. 2012.

Bergquist et al.; Motor unit recruitment when neuromuscular electrical stimulation is applied over a nerve trunk compared with a muscle belly: triceps surae, Journal of Applied Physiology; vol. 110, No. 3, pp. 627-637; Mar. 2011.

Bijelic et al.: E Actitrode®: The New Selective Stimulation Interface for Functional Movements in Hemiplegic Patients; Serbian Journal of Electrical Engineering; 1(3); pp. 21-28; Nov. 2004.

Birdno et al.; Pulse-to-pulse changes in the frequency of deep brain stimulation affect tremor and modeled neuronal activity.; Journal of Neurophysiology; 98; pp. 1675-1684; Jul. 2007.

Birdno et al.; Response of human thalamic neurons to high-frequency stimulation.; PloS One; 9(5); 10 pgs.; May 2014.

Birgersson et al.; Non-invasive bioimpedance of intact skin: mathematical modeling and experiments; Physiological Measurement; 32(1); pp. 1-18; Jan. 2011.

Bohling et al.; Comparison of the stratum corneum thickness measured in vivo with confocal Raman spectroscopy and confocal reflectance microscopy; Skin research and Technology; 20(1); pp. 50-47; Feb. 2014.

Bonaz, B., V. Sinniger, and S. Pellissier. "Vagus nerve stimulation: a new promising therapeutic tool in inflammatory bowel disease." Journal of internal medicine 282.1 (2017): 46-63.

Bowman et al.; Effects of waveform parameters on comfort during transcutaneous neuromuscular electrical stimulation; Annals of Biomedical Engineering; 13(1); pp. 59-74; Jan. 1985.

Bratton et al.; Neural regulation of inflammation: no neural connection from the vagus to splenic sympathetic neurons; Exp Physiol 97.11 (2012); pp. 1180-1185.

Brittain et al.; Tremor suppression by rhythmic transcranial current stimulation; Current Biology; 23; pp. 436-440; Mar. 2013.

Britton et al.; Modulation of postural tremors at the wrist by supramaximal electrical median nerve shocks in ET, PD, and normal subjects mimicking tremor; J Neurology, Neurosurgery, and Psychiatry; 56(10); pp. 1085-1089; Oct. 1993.

Buschbacher et al.; Manual of nerve conduction series; 2nd edition; Demos Medical Publishing, LLC; 2006 (part 1, Title to pg. #142).

Buschbacher et al.; Manual of nerve conduction series; 2nd edition; Demos Medical Publishing, LLC; 2006 (part 2, pg. #143 to #299).

Cagnan et al.; Phase dependent modulation of tremor amplitude in essential tremor through thalamic stimulation; Brain; 136(10); pp. 3062-3075; Oct. 2013.

Campero et al.; Peripheral projections of sensory fasicles in the human superificial radial nerve; Brain; 128(Pt 4); pp. 892-895; Apr. 2005.

Chen et al.; A web-based system for home monitoring of patients with Parkinson's disease using wearable sensors; IEEE Trans on Bio-Medical Engineering; 58(3); pp. 831-836; Mar. 2011.

(56) References Cited

OTHER PUBLICATIONS

Choi, Jong Bo, et al. "Analysis of heart rate variability in female patients with overactive bladder." Urology 65.6 (2005): 1109-1112.
Clair et al.; Postactivation depression and recovery of reflex transmission during repetitive electrical stimulation of the human tibial nerve, Journal of Neurophysiology; vol. 106, No. 1; pp. 184-192; Jul. 2011.
Clar et al.; Skin impedance and moisturization; J. Soc. Cosmet. Chem.; 26; pp. 337-353; 1975; presented at IFSCC Vilith Int'l Congresson Cosmetics Quality and Safety in London on Aug. 26-30, 1974.
Constandinou et al.; A Partial-Current-Steering Biphasic Stimulation Driver for Vestibular Prostheses; IEEE Trans on Biomedical Circuits and Systems; 2(2); pp. 106-113; Jun. 2008.
Daneault et al.; Using a smart phone as a standalone platform for detection and monitoring of pathological tremors; Frontiers in Human Neuroscience; vol. 6, article 357; 12 pgs.; Jan. 2012.
Deuschl et at; Consensus statement of the Movement Disorder Society on Tremor. Ad Hoc Scientific Committee., Movement Disorders, vol. 13 Suppl 3, pp. 2-23; (year of pub. sufficiently earlier than effective US filing date and any foreign priority date)1998.
Di Giovangiulio et al.; The Neuromodulation of the intestinal immune system and its relevance in inflammatory bowel disease; Fronteir's in Immunology; vol. 6; Article 590; Nov. 2015.
Dideriksen et al.; EMG-based characterization of pathological tremor using the iterated Hilbert transform; IEEE transactions on Biomedical Engineering; 58(10); pp. 2911-2921; Oct. 2011.
Dosen et al.: Tremor suppression using electromyography and surface sensory electrical stimulation; Converging Clinical and Engineering Research on Neurorehabilitation; vol. 1 (Siosystems & Biorobotics Series); pp. 539-543; Feb. 2013.
Doucet et al.; Neuromuscular electrical stimulation for skeletal muscle function; The Yale Journal of Biology and Medicine; 85(2); pp. 201-215; Jun. 2012.
Fiorentino, M., A. E. Uva, and M. M. Foglia. "Self calibrating wearable active running asymmetry measurement and correction." Journal of Control Engineering and Applied Informatics 13.2 (2011 ): 3-8. (Year: 2011).
Fuentes et al.; Restoration of locomotive function in Parkinson's disease by spinal cord stimulation: mechanistic approach, Eur J Neurosci, vol. 32, pp. 1100-1108; Oct. 2010 (author manuscript; 19 pgs.).
Fuentes et al.; Spinal cord stimulation restores locomotion in animal models of Parkinson's disease; Science; 323; pp. 1578-1582; Mar. 2009.
Gallego et al.; A neuroprosthesis for tremor management through the control of muscle co-contraction; Journal of Neuroengineering and Rehabilitation; vol. 10; 36; (13 pgs); Apr. 2013.
Gallego et al.; A soft wearable robot for tremor assessment and suppression; 2011 IEEE International Conference on Robotics and Automation; Shanghai International Conference Center; pp. 2249-2254; May 9-13, 2011.
Gallego et al.; Real-time estimation of pathological tremor parameters from gyroscope data.; Sensors; 10(3); pp. 2129-2149; Mar. 2010.
Gao; Analysis of amplitude and frequency variations of essential and Parkinsonian tremors; Medical & Biological Engineering & Computing; 42(3); pp. 345-349; May 2004.
Garcia et al.; Modulation of brainstem activity and connectivity by respiratory-gated auricular vagal afferent nerve stimulation in migraine patients; PAIN; International Association for the Study of Pain; 2017.
Garcia-Rill, E., et al. "Arousal, motor control, and Parkinson's disease." Translational neuroscience 6.1 pp. 198-207 (2015).
Giuffridda et al.; Clinically deployable Kinesia technology for automated tremor assessment.; Movement Disorders; 24(5); pp. 723-730; Apr. 2009.
Gracanin et al.; Optimal stimulus parameters for minimum pain in the chronic stimulatin of innervated muscle; Archives of Physical Medicine and Rehabilitation; 56(6); pp. 243-249; Jun. 1975.
Haeri et al.; Modeling the Parkinson's tremor and its treatments; Journal of Theorectical Biology; 236(3); pp. 311-322; Oct. 2005.
Halon En et al.; Contribution of cutaneous and muscle afferent fibres to cortical SEPs following median and radial nerve stimulation in man; Electroenceph. Clin. Neurophysiol.; 71(5); pp. 331-335; Sept.-Oct. 1988.
Hao et al.; Effects of electrical stimulation of cutaneous afferents on corticospinal transmission of tremor signals in patients with Parkinson's disease; 6th International Conference on Neural Engineering; San Diego, CA; pp. 355-358; Nov. 2013.
Hauptmann et al.; External trial deep brain stimulation device for the application of desynchronizing stimulation techniques; Journal of Neural Engineering; 6; 12 pgs.; Oct. 2009.
Heller et al.; Automated setup of functional electrical stimulation for drop foot using a novel 64 channel prototype stimulator and electrode array: Results from a gait-lab based study; Medical Engineering & Physic; 35(1); pp. 74-81; Jan. 2013.
Henry Dreyfuss Associates; The Measure of Man and Woman: Human Factors in Design (Revised Edition); John Wiley & Sons, New York; pp. 10-11 and 22-25; Dec. 2001.
Hernan, Miguel, et al. "Alcohol Consumption and the Incidence of Parkinson's Disease." May 15, 2003. Annals of Neurology. vol. 54. pp. 170-175.
Hua et al.; Posture-related oscillations in human cerebellar thalamus in essential tremor are enabled by voluntary motor circuits; J Neurophysiol; 93(1); pp. 117-127; Jan. 2005.
Huang, et al.; Theta burst stimulation report of the human motor cortex; Neuron, vol. 45, 201-206, Jan. 20, 2005.
Hubeaux, Katelyne, et al. "Autonomic nervous system activity during bladder filling assessed by heart rate variability analysis in women with idiopathic overactive bladder syndrome or stress urinary incontinence." The Journal of urology 178.6 (2007): 2483-2487.
Hubeaux, Katelyne, et al. "Evidence for autonomic nervous system dysfunction in females with idiopathic overactive bladder syndrome." Neurourology and urodynamics 30.8 (2011): 1467-1472.
Inoue, Masahiro, Katsuaki Suganuma, and Hiroshi Ishiguro. "Stretchable human interface using a conductive silicone elastomer containing silver fillers." Consumer Electronics, 2009. ISCE'09. IEEE 13th International Symposium on. IEEE, 2009.
Jacks et al.; Instability in human forearm movements studied with feed-back-controlled electrical stimulation of muscles; Journal of Physiology; 402; pp. 443-461; Aug. 1988.
Jobges et al.; Vibratory proprioceptive stimulation affects Parkinsonian tremor; Parkinsonism & Related Disorders; 8(3); pp. 171-176; Jan. 2002.
Joundi et al.; Rapid tremor frequency assessment with the iPhone accelerometer.; Parkinsonism & Related Disorders; 17(4); pp. 288-290; May 2011.
Kim et al.: Adaptive control of movement for neuromuscular stimulation-assisted therapy in a rodent model; IEEE Trans on Biomedical Engineering,; 56(2); pp. 452-461; Feb. 2009.
Krauss et al.; Chronic spinal cord stimulation in medically intractable orthostatic tremor; J Neurol Neurosurg Psychiatry; 77(9); pp. 1013-1016; Sep. 2006.
Krishnamoorthy et al.; Gait Training After Stroke: A pilot study combining a gravity balanced orthosis, functional electrical stimulation and visual feedback, Journal of Neurologic Physical Therapy, vol. 32, No. 4, pp. 192-202, 2008.
Kuhn et al.; Array electrode design for transcutaneous electrical stimulation a simulation study; Medical Engineering & Physics; 31 (8); pp. 945-951; Oct. 2009.
Kuhn et al.; The Influence of Electrode Size on Selectivity and Comfort in Transcutaneous Electrical Stimulation of the Forearm; Neural Systems and Rehabilitation Engineering, IEEE Transactions on; 18(3); pp. 255-262; Jun. 2010.
Kunz, Patrik, et al. "5 kHz transcranial alternating current stimulation: lack of cortical excitability changes when grouped in a theta burst pattern." Frontiers in Human Neuroscience 10 (2016): 683.
Lagerquist et al.: Influence of stimulus pulse width on M-waves, H-reflexes, and torque during tetanic low-intensity neuromuscular stimulation, Muscle & Nerve, 42(6), pp. 886-893; Dec. 2010.

(56) References Cited

OTHER PUBLICATIONS

Laroy et al.; The sensory innervation pattern of the fingers; J. Neurol.; 245 (5); pp. 294-298; May 1998.
Lee et al.; Resetting of tremor by mechanical perturbations: A comparison of essential tremor and parkinsonian tremor; Annals of Nuerology; 10(6); pp. 523-531; Dec. 1981.
Legon et al.; Pulsed ultrasound differentially stimulates somatosensory circuits in humans as indicated by EEG and fMRI; PLoS ONE; 7(12); e51177; 14 pgs.; Dec. 2012.
Liao, Wen-Chien, et al. "A noninvasive evaluation of autonomic nervous system dysfunction in women with an overactive bladder." International Journal of Gynecology & Obstetrics 110.1 (2010): 12-17.
Lourenco et al.; Effects produced in human arm and forearm motoneurones after electrical stimulation of ulnar and median nerves at wrist level; Experimental Brain Research; 178(2); pp. 267-284; Apr. 2007.
Malek et al.; The utility of electromyography and mechanomyography for assessing neuromuscular function: a noninvasive approach; Phys Med Rehabil in N Am; 23(1); pp. 23-32; Feb. 2012.
Mamorita et al.; Development of a system for measurement and analysis of tremor using a three-axis accelerometer; Methods Inf Med; 48(6); pp. 589-594; epub Nov. 2009.
Maneski et al.; Electrical Stimulation for suppression of pathological tremor; Med Biol Eng Comput; 49(10); pp. 1187-1193; Oct. 2011.
Marsden et al.; Coherence between cerebellar thalamus, cortex and muscle in man; Brain; 123; pp. 1459-1470; Jul. 2000.
Marshall, Ryan, et al. "Bioelectrical stimulation for the reduction of inflammation in inflammatory bowel disease." Clinical Medicine Insights: Gastroenterology 8 (2015): CGast-S31779.
McAuley et al.; Physiological and pathological tremors and rhythmic central motor control; Brain; 123(Pt 8); pp. 1545-1567; Aug. 2000.
McIntyre et al.; Finite element analysis of current-density and electric field generated by metal microelectrodes; Annals of Biomedical Engineering; 29(3); pp. 227-235; Mar. 2001.
Meekins et al.; American Association of Neuromuscular & Electrodiagnostic Medicine evidenced-based review: use of surface electromyography in the diagnosis and study of neuromuscular disorders; Muscle Nerve 38(4); pp. 1219-1224; Oct. 2008.
Mehnert, Ulrich, et al. "Heart rate variability: an objective measure of autonomic activity and bladder sensations during urodynamics." Neurourology and urodynamics 28.4 (2009): 313-319.
Miguel et al.; Alcohol consumption and the incidence of Parkinson's disease; Ann. Neurol.; 54(2); pp. 170-175; May 15, 2003.
Miller et al.; Multiplexed microneedle-based biosensor array for characterization of metabolic acidosis; Talanta; 88; pp. 739-742; Jan. 2012 (author manuscript; 13 pgs.).
Miller et al.; Neurostimulation in the treatment of primary headaches; Pract Neurol; Apr. 11, 2016;16:pp. 362-375.
Milne et al.; Habituation to repeated in painful and non-painful cutaneous stimuli: A quantitative psychophysical study; Experimental Brain Research; 87(2); pp. 438-444; Nov. 1991.
Mommaerts et al.; Excitation and nerve conduction; in Comprehensive Human Physiology; Springer Berlin Heidelberg; Chap. 13; pp. 283-294; Mar. 1996.
Mones et al.; The response of the tremor of patients with Parkinsonism to peripheral nerve stimulation; J Neurology, Neurosurgery, and Psychiatry; 32(6); pp. 512-518; Dec. 1969.
Morgante et al.: How many parkinsonian patients are suitable candidates for deep brain stimulation of subthalamic nucleus?; Results of a Questionnaire, Partkinsonism Relat Disord; 13; pp. 528-531; Dec. 2007.
Munhoz et al.; Acute effect of transcutaneous electrical nerve stimulation on tremor; Movement Disorders; 18(2); pp. 191-194; Feb. 2003.
Nardone et al.; Influences of transcutaneous electrical stimulation of cutaneous and mixed nerves on subcortical somatosensory evoked potentials; Electroenceph. Clin. Neurophysiol.; 74(1); pp. 24-35; Jan.-Feb. 1989.
Nonis et al.; Evidence of activation of vagal afferents by non-invasive vagus nerve stimulation: An electrophysiological study in healthy volunteers; Cephalalgia; pp. 1285-1293; vol. 37(13); Mar. 28, 2017.
Perez et al.; Patterned Sensory Stimulation Induces Plasticity in Reciprocal Ia Inhibition in Humans; The Journal of Neuroscience; 23(6); pp. 2014-2018; Mar. 2003.
Perlmutter et al.; Deep brain stimulation; Ann Rev Neurosci; 29; pp. 229-257; Jul. 2006.
Popović-Bijelić, Ana, et al. "Multi-field surface electrode for selective electrical stimulation." Artificial organs 29.6 (2005): 448-452.
Prochazka et al.; Attenuation of pathological tremors by functional electrical stimulation I: Method; Annals of Biomedical Engineering; 20(2); pp. 205-224; Mar. 1992.
Pulliam et al.; Continuous in-home monitoring of essential tremor; Parkinsonism Relat Disord; 20(1); pp. 37-40; Jan. 2014.
Quattrini et al.; Understanding the impact of painful diabetic neuropathy; Diabetes/Metabolism Research and Reviews; 19, Suppl. 1; pp. S2-8; Jan-Feb. 2003.
Rocon et al.; Design and validation of a rehabilitation robotic exoskeleton for tremor assessment and suppression; IEEE Trans Neural Sys and Rehab Eng.; 15(3); pp. 367-378; Sep. 2007.
Sigrist et al.; Augmented visual, auditory, haptic and multimodal feedback in motor learning; A review. Psychonomic Bulletin & Review, 20(1), pp. 21-53 (2012).
Silverstone et al.; Non-invasive Neurostimulation In The Control of Familial Essential Tremor Using The Synaptic Neuromodulator; Conference Proceedings, International Functional Electrical Stimulation Society (IFES); Ed. Paul Meadows; 3 pgs.; May 1999.
Singer et al.; The effect of EMG triggered electrical stimulation plus task practice on arm function in chronic stroke patients with moderate-severe arm deficits; Restor Neurol Neurosci; 31(6); pp. 681-691; Oct. 2013.
Solomonow, Met al. "Studies Toward Spasticity Suppression With High Frequency Electrical Stimulation". Orthopedics, vol. 7, No. 8, 1984, pp. 1284-1288. SLACK, Inc., https://dol.org/10.3928/0147-7447-19840801-11 (Year: 1998).
Straube et al.; Treatment of chronic migraine with transcutaneous stimulation of the auricular branch of the vagal nerve (auricular t-VNS): a randomized, monocentric clinical trial; The Journal of Headache and Pain (2015) 16:63.
Takanashi et al.; A functional MRI study of somatotopic representation of somatosensory stimulation in the cerebellum; Neuroradiology; 45(3); pp. 149-152; Mar. 2003.
Tass et al.; Coordinated reset has sustained aftereffects in Parkinsonian monkeys; Ann Neurol; 72(5); pp. 816-820; Nov. 2012.
Tass et al.; Counteracting tinnitus by acoustic coordinated reset neuromodulation; Restorative neurology and Neuroscience; 30(2); pp. 137-159; Apr. 2012.
Tass; A Model of desynchronizing deep brain stimulation with a demand-controlled coordinated reset of neural subpopulations; Bioi Cybern; 89(2); pp. 81-88; Aug. 2003.
Thomas et al.; A review of posterior tibial nerve stimulation for faecal incontinence; Colorectal Disease; 2012 The Association of Coloproctology of Great Britain and Ireland. 15, pp. 519-526; Jun. 25, 2012.
Toloso et al.; Essential tremor: treatment with propranolol; Neurology; 25(11); p. 1041; Nov. 1975.
TRACEY; The inflammatory reflex; Nature; vol. 420; pp. 853-859; 19/26 Dec. 2002.
Treager; Interpretation of skin impedance measurements; Nature; 205; pp. 600-601; Feb. 1965.
Valente; Novel methods and circuits for field shaping in deep brain stimulation; Doctoral thesis, UCL (University College London); 222 pp. 2011.
Vitton et al.; Transcutaneous posterior tibial nerve stimulation for fecalIncontinence in inflammatory bowel disease patients: a therapeutic option?; Inflamm Bowel Dis; vol. 15, No. 3, Mar. 2009; pp. 402-405.

(56) References Cited

OTHER PUBLICATIONS

Von Lewinski et al.; Efficacy of EMG-triggered electrical arm stimulation in chronic hemiparetic stroke patients; Restor Neurol Neurosci; 27(3); pp. 189-197; Jun. 2009.
Wardman et al.; Subcortical, and cerebellar activation evoked by selective stimulation of muscle and cataneous afferents: an fMRI study; Physiol. Rep.; 2(4); pp. 1-16; Apr. 2014.
Wiestler et al.; Integration of sensory and motor representations of single fingers in the human; J. Neurophysiol.; 105(6); pp. 3042-3053; Jun. 2011.
Woldag et al.; Evidence-based physiotherapeutic concepts for improving arm and hand function in stroke patients R A review; J Neurol; 249(5); pp. 518-528; May 2002.
Woolf et al.; Peripheral nerve injury triggers central sprouting of myelinated afferents; Nature; 355(6355); pp. 75-78; Jan. 1992.
Yarnitsky et al.; Nonpainful remote electrical stimulation alleviates episodic migraine pain; Neurology 88; pp. 1250-1255; Mar. 28, 2017.
Yeh, Kuei-Lin, Po-Yu Fong, and Ying-Zu Huang. "Intensity sensitive modulation effect of theta burst form of median nerve stimulation on the monosynaptic spinal reflex." Neural plasticity 2015 (2015) in 8 pages.
Yilmaz, Ozlem O., et al. "Efficacy of EMG-biofeedback in knee osteoarthritis." Rheumatology international 30.7 (2010): 887-892.
Zhang et al.; Neural oscillator based control for pathological tremor suppression via functional electrical stimulation; Control Engineering Practice; 19(1); pp. 74-88; Jan. 2011.
Zorba et al.; Overactive bladder and the pons; Rize University, Medical Faculty, Department of Urology; 123-124; Undated.
Zwarts et al.; Multichannel surface EMG: basic aspects and clinical utility; Muscle Nerve; 28(1); pp. 1-17; Jul. 2003.
PCT, PCT/US2014/012388 (published as WO 2014/113813, filed Jan. 21, 2014.
U.S., U.S. Appl. No. 14/805,385 (now U.S. Pat. No. 9,452,287), filed Jul. 21, 2015.
U.S., U.S. Appl. No. 15/277,946 (now U.S. Pat. No. 10,850,090), filed Sep. 27, 2016.
U.S. U.S. Appl. No. 15/983,024 (now U.S. Pat. No. 10,625,074), filed May 17, 2018.
U.S., U.S. Appl. No. 17/107,435 (published as U.S. Pub. No. 2021/0100999), filed Nov. 30, 2020.
PCT, PCT/US2019/039193 (published as PCT Pub. No. WO 2020/006048), filed Jun. 26, 2019.
U.S., U.S. Appl. No. 14/271,669 (published as U.S. Pub. No. 2014/0336722), filed Nov. 13, 2014.
PCT, PCT/US2015/033809 (published as WO 2015/187712), filed Jun. 2, 2015.
U.S., U.S. Appl. No. 15/354,943 (now U.S. Pat. No. 9,802,041), filed Nov. 17, 2016.
U.S., U.S. Appl. No. 15/721,475 (now U.S. Pat. No. 10,179,238), filed Sep. 29, 2017.
U.S., U.S. Appl. No. 15/721,480 (now U.S. Pat. No. 10,173,060), filed Sep. 29, 2017.
U.S., U.S. Appl. No. 16/242,983 (now U.S. Pat. No. 10,549,093), filed Jan. 8, 2019.
U.S., U.S. Appl. No. 16/247,310 (now U.S. Pat. No. 10,561,839), filed Jan. 14, 2019.
U.S., U.S. Appl. No. 16/780,758 (now U.S. Pat. No. 10,905,879), filed Feb. 3, 2020.
U.S., U.S. Appl. No. 16/792,100 (now U.S. Pat. No. 10,960,207), filed Feb. 14, 2020.
U.S., U.S. Appl. No. 17/164,576 (published as U.S. Pub. No. 2021/0330974), filed Feb. 1, 2021.
U.S., U.S. Appl. No. 17/216,372 (published as U.S. Pub. No. 2021/0308460), filed Mar. 29, 2021.
PCT, PCT/US2016/037080 (published as WO 2016/201366), filed Jun. 10, 2016.
U.S., U.S. Appl. No. 15/580,631 (now U.S. Pat. No. 10,765,856), filed Dec. 7, 2017.
U.S., U.S. Appl. No. 17/013,396 (published as U.S. Pub. No. 2021/0052883), filed Sep. 4, 2020.
PCT, PCT/US2017/014431 (published as WO 2017/132067), filed Jan. 20, 2017.
U.S., U.S. Appl. No. 16/071,056, (now U.S. Pat. No. 11,344,722), filed Jul. 18, 2018.
U.S., U.S. Appl. No. 17/633,004, filed May 11, 2022.
PCT, PCT/US2018/025752 (published as WO 2018/187241), filed Apr. 2, 2018.
U.S., U.S. Appl. No. 16/500,377 (now U.S. Pat. No. 11,331,480), filed Apr. 2, 2018.
U.S., U.S. Appl. No. 17,663,010, filed May 11, 2022.
PCT, PCT/US2016/045038 (published as WO 2017/023864), filed Aug. 1, 2016.
U.S., U.S. Appl. No. 15/748,616 (published as U.S. Publ No. 2020/0093400), filed Jan. 29, 2018.
PCT, PCT/US2016/053513 (published as WO 2017/053847), filed Sep. 23, 2016.
U.S., U.S. Appl. No. 15/762,043 (now U.S. Pat. No. 10,603,482), filed Mar. 21, 2018.
U.S., U.S. Appl. No. 16/833,388 (published as U.S. Pub. No. 2020/0289814), filed Mar. 27, 2020.
PCT, PCT/US2017/040920 (published as WO 2018/009680), filed Jul. 6, 2017.
U.S., U.S. Appl. No. 16/241,846 (now U.S. Pat. No. 10,814,130), filed Jan. 7, 2019.
U.S., U.S. Appl. No. 17/080,544 (published as U.S. Pub. No. 2021/0113834), filed Oct. 26, 2020.
PCT, PCT/US2017/048424 (published as WO 2018/039458), filed Aug. 24, 2017.
U.S., U.S. Appl. No. 16/327,780 (published as U.S. Pub. No. 2021/0283400), filed Feb. 22, 2019.
PCT, PCT/US2019/013966 (publihsed as WO 2019/143790), filed Jan. 17, 2019.
U.S., U.S. Appl. 16/962,810 (published as U.S. Pub. No. 2021/0252278), filed Jan. 17, 2019.
PCT, PCT/US2019/030458 (published as WO 2019/213433), filed May 2, 2019.
U.S., U.S. Appl. No. 17/052,483 (published as U.S. Pub. No. 2021/0244940), filed Jan. 17, 2019.
PCT, PCT/US2019/053297 (published as WO 2020/069219), filed Sep. 26, 2019.
U.S., U.S. Appl. No. 17/279,048 (published as U.S. Pub. No. 2021/0402172), filed Mar. 23, 2021.
PCT, PCT/US2019/057674 (published as WO 2020/086726), filed Oct. 23, 2019.
U.S., U.S. Appl. No. 17/287,471 (published as U.S. Pub. No. 2021/0379374), filed Apr. 21, 2021.

* cited by examiner

PRE POST

SYSTEMS AND METHODS FOR PERIPHERAL NERVE STIMULATION IN THE FINGER OR HAND TO TREAT HAND TREMORS

CROSS REFERENCE TO RELATED APPLICATIONS

This application claims the benefit as a continuation of U.S. patent application Ser. No. 15/762,043 filed on Mar. 21, 2018, now U.S. Pat. No. 10,603,482, which is the U.S. National Stage of PCT App. No. PCT/US2016/053513 which claims priority to U.S. Provisional Application No. 62/222,210, filed Sep. 23, 2015, and U.S. Provisional Application No. 62/251,617, filed Nov. 5, 2015, each of the foregoing of which is herein incorporated by reference in their entireties.

INCORPORATION BY REFERENCE

All publications and patent applications mentioned in this specification are herein incorporated by reference to the same extent as if each individual publication or patent application was specifically and individually indicated to be incorporated by reference.

This application may be related to International Patent Application No. PCT/US2014/012388, filed Jan. 21, 2014, International Patent Application No. PCT/US2015/033809, filed Jun. 2, 2015, and International Patent Application No. PCT/US2016/037080, filed Jun. 10, 2016, each of which is herein incorporated by reference in its entirety.

Campero M, Serra J, Ochoa J L. Peripheral projections of sensory fascicles in the human superficial radial nerve. Brain 2005; 128:892-895.

Halonen J P, Jones S, Shawkat F. Contribution of cutaneous and muscle afferent fibres to cortical SEPs following median and radial nerve stimulation in man Electroenceph Clin Neurophysiol 1988; 71:331-335.

Laroy V, Spaans F, Reulen J. The sensory innervation pattern of the fingers. J Neurol 1998; 245:294-298.

Nardone A, Schieppati M. Influences of transcutaneous electrical stimulation of cutaneous and mixed nerves on subcortical and cortical somatosensory evoked potentials. Electroenceph Clin Neurophysiol 1989; 74:24-35.

Takanashi M, Abe K, Yanagihara T, Sakoda S, Tanaka H, Hirabuki N, Nakamura H, Fujita N. A functional MRI study of somatotopic representation of somatosensory stimulation in the cerebellum. Neuroradiology 2003; 45:149-152.

Wardman D L, Gandevia S C, Colebatch J G. Cerebral, subcortical, and cerebellar acivation evoked by selective stimulation of muscle and cutaneous afferents: an fMRI study. Physiol Rep, 2014; 2(4):1-16.

Wiestler T, McGonigle D J, Diedrichsen J. Integration of sensory and motor representations of single fingers in the human cerebellum. J Neurophysiol 2011; 105:3042-305.

FIELD

Embodiments of the invention relate generally to systems, devices, and methods for treating tremor using peripheral nerve stimulation, and more specifically to systems, devices, and methods for stimulating peripheral nerves in the fingers or hand to treat tremor.

BACKGROUND

Essential tremor (ET) is the most common movement disorder in the United States and currently affects an estimated 10 million individuals. Its prevalence increases with age, making it a growing concern for the U.S. aging population. ET affects 6.3% of the population over 65, but over 20% of people over the age of 95. It is characterized by 4-7 Hz oscillatory movement in the distal limbs, especially the hands. Unlike Parkinsonian tremor, which predominantly occurs during rest, essential tremor is postural (induced by holding a limb against gravity) and kinetic (present during movement).

Tremor is also a significant problem for patients with orthostatic tremor, multiple sclerosis, dystonia and Parkinson's disease. Although the underlying etiology of tremor in these conditions differs from that of ET, treatment options are similarly limited.

A number of conditions, such as tremors, can be treated through some form of transcutaneous peripheral nerve stimulation. Previous work and patent applications (e.g., PCT/US2014/012388, PCT/US2015/033809, PCT/US2016/037080) have focused on applying stimulation to the median, radial, and/or ulnar nerves on the arm or wrist. However, applying stimulation to the arm or wrist remains challenging because of natural variation in wrist diameter, nerve locations, nerve depolarization characteristics, and skin conduction. This leads to significant challenges in designing a device to comfortably, safely, and reliably stimulate the peripheral nerves across a broad population of potential users. For example, variation in the size and location of the ulnar styloid process (i.e., a bony formation on the wrist) may prevent the comfortable application of a wrist-worn stimulator that requires an electrode to conform to the wearer's skin. Additionally, as the wrist has a large range of motion with many tendons, there may be greater variability in stimulation sensation of a wrist worn stimulator due to normal hand motion.

SUMMARY OF THE DISCLOSURE

The present invention relates generally to systems, devices, and methods for treating tremor using peripheral nerve stimulation, and more specifically to systems, devices, and methods for stimulating peripheral nerves in the fingers or hand to treat tremor.

Prior neurophysiology research studies have demonstrated that electrical stimulation of the digits in the hand can activate similar pathways in the brain and spine as stimulation of individual mixed nerves at the wrist (Halonen et al., 1988; Nardone et al., 1990; Takanashi et al., 2003; Wiestler et al., 2011; Wardman et al., 2014). The sensory innervation of the hand has been mapped out in detail (Laroy et al., 1998; Campero et al., 2005), providing a rationale for selective targeting of individual nerves by applying focal cutaneous stimulation of digits.

To overcome challenges with anatomical sizing, variation in nerve location, and comfort, this application describes devices and methods for applying electrical stimulation to the nerves that innervate the hand and fingers. As shown in FIGS. 1A and 1B, the branches of the median, radial, and ulnar nerves that innervate the hand and fingers can be stimulated by a device worn on the hand or fingers and achieve tremor reduction. Further, targeting the nerves at the fingers improves stimulation specificity since nerves at the finger are predominantly sensory (i.e., afferent) while nerves at the wrist contain both sensory (i.e., afferent) and motor fibers (i.e., efferent). The electrodes are positioned to target the sensory branches of the median, radial and ulnar nerves in the hand. Specifically, these afferent nerves may carry cutaneous sensory information about the position of the fingers in time and space to the central nervous system. In addition, various pairs of nerves, such as the radial and median nerve, can be selectively stimulated by stimulating the index and middle fingers and the thumb, which also avoids stimulation of ulnar nerve. Stimulation of the little finger allow selective stimulation of the ulnar nerve, and stimulation of the ring finger allows stimulation of all three nerves. As shown in FIG. 2, this sensory information is thought to input into or be transmitted to the thalamic relay nuclei (e.g., ventral posterolateral (VPL) or ventral intermediate (VIM) nucleus) pathway, where it may intersect and disrupt or desynchronize the tremor circuit in the central nervous system.

As a proof of concept, two patients with tremor have been stimulated on their index finger to assess the effect of electrical stimulation of the finger on reduction of hand tremors. Patient 01 was a 69 year old male. The top and middle segments of the index finger were stimulated on the palmar side of the finger with a 1 cm×2 cm electrode pair, as shown in FIG. 3A. Patient 01 received constant stimulation at 150 Hz for 30 minutes. Spirals drawn pre-stimulation and post-stimulation show a noticeable reduction in hand tremor, as shown in FIG. 3B. Patient 02 was a 61 year old female tested on Sep. 11, 2015. The patient was stimulated on the distal segment of the index finger with two 1 cm×2 cm electrode pairs, as shown in FIG. 4A (i.e., an electrode pair on the palmar side and an electrode pair on the dorsal side). The stimulation alternated a 150 Hz biphasic waveform between the electrode pairs at a frequency that matched the patient's measured tremor frequency (e.g., between 4-12 Hz). Spirals drawn pre-stimulation and post-stimulation show a noticeable reduction in hand tremor as shown in FIG. 4B. Both subjects were consented under an IRB approved protocol.

Additionally, social stigma and embarrassment greatly affect the quality of life of people with ET and other types of hand tremor. A hand-worn device or ring can have a form that is more discreet than an arm or wrist-worn device. This is relevant during social and other public situations when it is desired to keep the tremor reduction therapy discreet. Additionally, compared to the arm or wrist, less power is required to stimulate the branches of the median, radial, and ulnar nerves in the hand and fingers. This would allow for a smaller power source and stimulator.

Additionally, a peripheral nerve stimulator worn on the finger, such as a ring, provides better contact with the wearer's skin. This is due in part to the tissue composition in the finger, which includes malleable fatty tissue, and reduced patient to patient size variation in the finger as compared to other body parts, such as the wrist. Movement of the finger is less likely to move the device relative to the locations of the median, radial, and ulnar nerves. This allows a hand or finger-worn device to maintain strong contact with the skin throughout the range of normal motion. This contact enables the use of dry- or wetted-electrodes instead of sticky gels and adhesives.

Additionally, there are advantages to measuring upper extremity tremor motion at the hand and/or fingers, as opposed to the arm and/or wrist. While it is possible to generate data and measure tremor motion at the arm and/or wrist, it is more accurate to do so at the hand and/or fingers. Tremor at the hand and/or fingers is a better representation of the functional impact that tremor has on a patient's ability to perform activities of daily living.

In some embodiments, a wearable ring device for treating hand tremors by electrically stimulating one or more sensory nerves on a finger of a patient's hand is provided. The device includes an annular member defining an aperture that is sized to receive a finger of the patient; a first electrode, a second electrode, and a third electrode housed on an inside surface of the annular member and configured to be in contact with the patient's skin when worn on the finger; and a stimulation unit that is configured to connect to the annular member, wherein when the unit is connected to the annular member the unit is in electrical communication to the first electrode, the second electrode, and the third electrode, wherein the unit houses a power source and a pulse generator configured to deliver pulsed electrical stimulation to the one or more sensory nerves in the finger.

In some embodiments, when worn the first electrode is configured to be positioned on the dorsal side of the finger, the second electrode is configured to be positioned on the palmar side of the finger, and the third electrode is configured to be positioned between the first and second electrodes.

In some embodiments, the third electrode is a common ground electrode.

In some embodiments, the finger is the index finger, middle finger, or the ringer finger.

In some embodiments, the device further includes a fourth electrode housed on the inside surface of the annular member.

In some embodiments, the power source is a capacitor.

In some embodiments, the power source is a rechargeable battery.

In some embodiments, the stimulation unit is detachable.

In some embodiments, the third electrode is configured to be positioned approximately equidistant between the first and second electrodes when the device is worn.

In some embodiments, the first, second, and third electrodes comprise a dry conductive polymer or rubber with a textured surface configured to capture moisture from the skin, air, or other external sources.

In some embodiments, the first, second, and third electrodes comprise a wicking conductive fabric configured to capture moisture from the skin, air, or other external sources.

In some embodiments, the device further includes a wireless transceiver electrically connected to the pulse generator and configured to communicate with at least one external electronic device.

In some embodiments, the annular member comprises a flexible housing material, and the first, second, and third electrodes are electrically connected with flexible electronic circuitry that is configured to conform to a predetermined range of finger diameters and configured to accommodate variation in finger diameter over time.

In some embodiments, the annular member comprises one or more motion sensors, and wherein the pulse generator is configured to modulate the pulsed electrical stimulation based on measurements of tremor motion and activity from the one or more motion sensors, wherein the one or more motion sensors are selected from the group consisting of an inertial measurement unit, an accelerometer, a gyroscope, and a magnetometer.

In some embodiments, the one or more motion sensors in the annular member along with a processor located in the stimulation unit or at least one external device are configured to measure and detect one or more predetermined motions and to modulate the pulsed electrical stimulation based on the measurement and detection of the one or more predetermined motions.

In some embodiments, one or more predetermined motions is selected from the group consisting of knocking the hand of the patient on an object a predetermined number of times, raising the arm up, waving the hand, opening and closing the hand, tapping the finger on a table a predetermined number of times, snapping the fingers, clapping of hands, and pointing.

In some embodiments, the inside surface of the annular member is free from gels and adhesives.

In some embodiments, the device further includes a second annular member defining an aperture that is sized to receive the first finger of the patient, wherein the second annular member comprises one or more motion sensors configured to measure motion of the patient's hand.

In some embodiments, the second annular member is configured to communicate with the stimulation unit and/or the at least one external device.

In some embodiments, the second annular member is configured to detachably connect to the stimulation unit.

In some embodiments, the second annular member comprises a wireless transceiver.

In some embodiments, when worn the first electrode is configured to be positioned on the dorsal side of the first finger, the second electrode is configured to be positioned on the palmar side of the first finger, and the third electrode is a circumferential electrode configured to be positioned circumferentially on the inside surface of the annular member and proximal of first and second electrodes.

In some embodiments, a wearable ring device for treating hand tremors by electrically stimulating one or more sensory nerves on one or more fingers of a patient's hand is provided. The device includes a first annular member defining an aperture that is sized to receive a first finger of the patient, wherein the first finger is an index, middle, or ring finger; a second annular member defining an aperture that is sized to receive a second finger of the patient; a first electrode and a second electrode disposed on an inside surface of the first annular member and configured to be in contact with the patient's skin when worn on the first finger; a third electrode and a fourth electrode disposed on an inside surface of the annular member and configured to be in contact with the patient's skin when worn on the second finger; and a unit housing a power source and a pulse generator configured to deliver pulsed electrical stimulation to the one or more sensory nerves through the first electrode and the second electrode, and the third electrode and the fourth electrode.

In some embodiments, a method of reducing tremor in a patient's hand is provided. The method includes measuring motion in the patient's hand with a sensor worn on one of the patient's fingers; determining one or more characteristics of the tremor based on a signal generated by the motion sensor; and stimulating one or more sensory nerves in a first finger of the patient according to a set of stimulation parameters using a wearable stimulator, wherein the set of stimulation parameters is based in part on the one or more of the determined tremor characteristics, wherein the one or more sensory nerves is selected from the group consisting of the medial nerve, the radial nerve, and the ulnar nerve.

In some embodiments, the one or more characteristics of the tremor is selected from the group consisting of the tremor frequency, tremor amplitude, and tremor phase.

In some embodiments, the step of stimulating one or more sensory nerves comprises stimulating two sensory nerves.

In some embodiments, the method further includes isolating tremor based motion from non-tremor based motion in the measured motion.

In some embodiments, a system for treating hand tremors by electrically stimulating one or more sensory nerves on a finger of a patient's hand is provided. The system includes a ring device that includes an annular member defining an aperture that is sized to receive a first finger of the patient, wherein the first finger is an index or a middle finger; and a first electrode, a second electrode, and a third common ground electrode housed on an inside surface of the annular member and configured to be in contact with the patient's skin when worn on the first finger. The system further includes a wrist unit in electrical communication with the ring device that is configured to be worn around the patient's wrist, wherein the wrist unit houses a processor, a power source, and a pulse generator configured to deliver pulsed electrical stimulation to the one or more sensory nerves in the first finger through the ring device.

In some embodiments, a system for treating hand tremors by electrically stimulating one or more sensory nerves on a finger of a patient's hand is provided. The system includes a ring device that includes an annular member defining an aperture that is sized to receive a first finger of the patient, wherein the first finger is an index or a middle finger; and a first electrode, a second electrode, and a third common ground electrode housed on an inside surface of the annular member and configured to be in contact with the patient's skin when worn on the first finger. The system further includes a mobile phone comprising a processor and a battery; and an adapter in electrical communication with both the ring device and the mobile phone, wherein the adapter comprises a pulse generator configured to deliver pulsed electrical stimulation to the one or more sensory nerves in the first finger through the ring device, wherein the mobile phone is configured to control the pulse generator.

The devices and methods of this disclosure each have several innovative aspects, no single one of which is solely responsible for the desirable attributes disclosed herein. The present application discloses devices and methods to reduce tremor in an individual. In some embodiments, a device is provided. The device can include a housing and one or more affectors, power sources, or controls. In some embodiments, the device additionally includes one or more sensors. Further aspects and embodiments of the present invention are set forth herein.

These and other aspects and embodiments of the invention are described in greater detail below, with reference to the drawing figures.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Our invention is a device and system to measure and collect motion data, analyze said data, as to interpret how these measures may influence motion disorders, and stimulate individual peripheral nerve targets to reduce tremor. The purpose of the data analysis is to see how the measured data may influence motion disorders. The applied stimulation may or may not be modified based on the measured data.

Figure 1A:
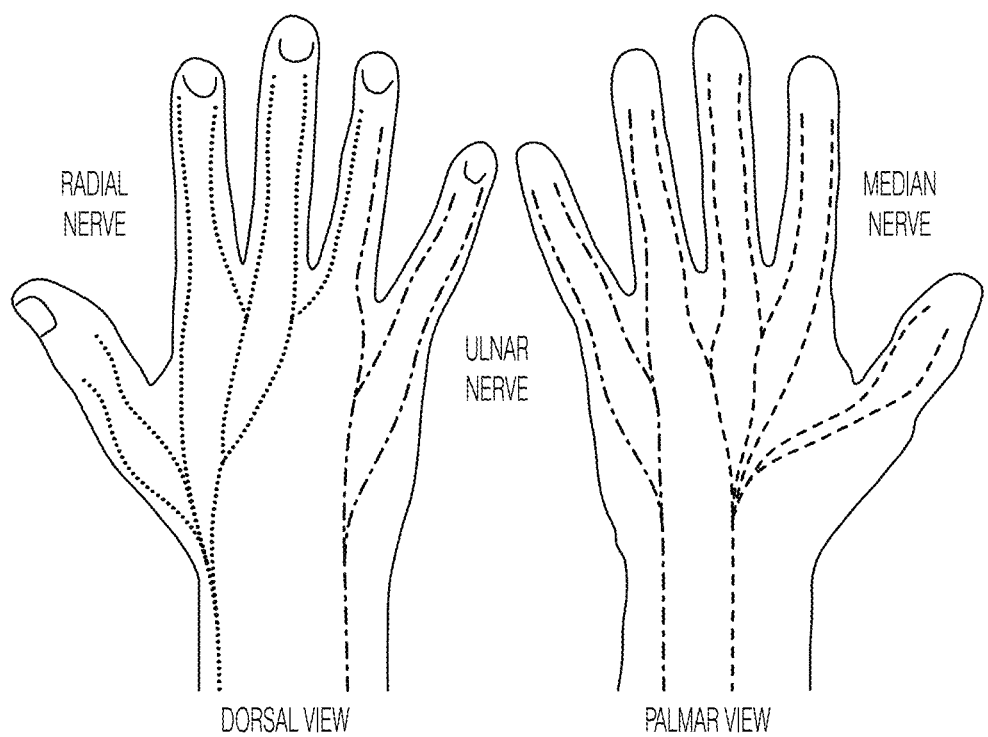
FIG. 1A illustrates a diagram of nerves and nerve distribution in the hand and fingers. Radial nerve is dotted, ulnar nerve is dash-dot, and median nerve is dashed.
Figure 1B:
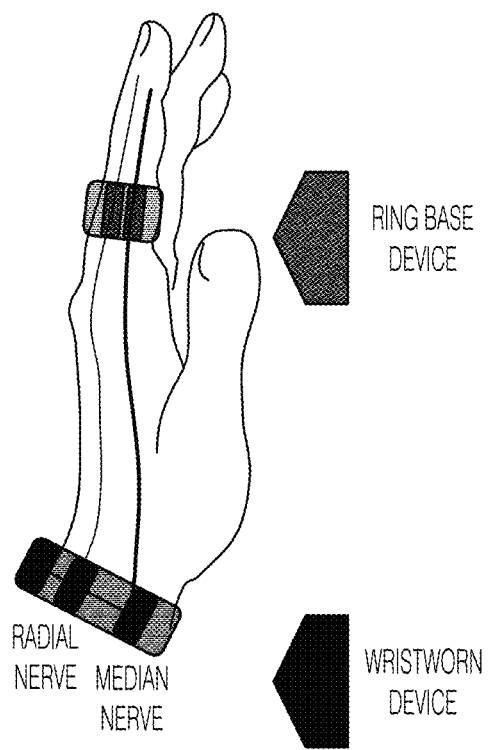
FIG. 1B illustrates a diagram of the radial and median nerve branches from the wrist to the finger, illustrating how a ring-based device could stimulate the same pathways as a wrist worn device.
Figure 2:
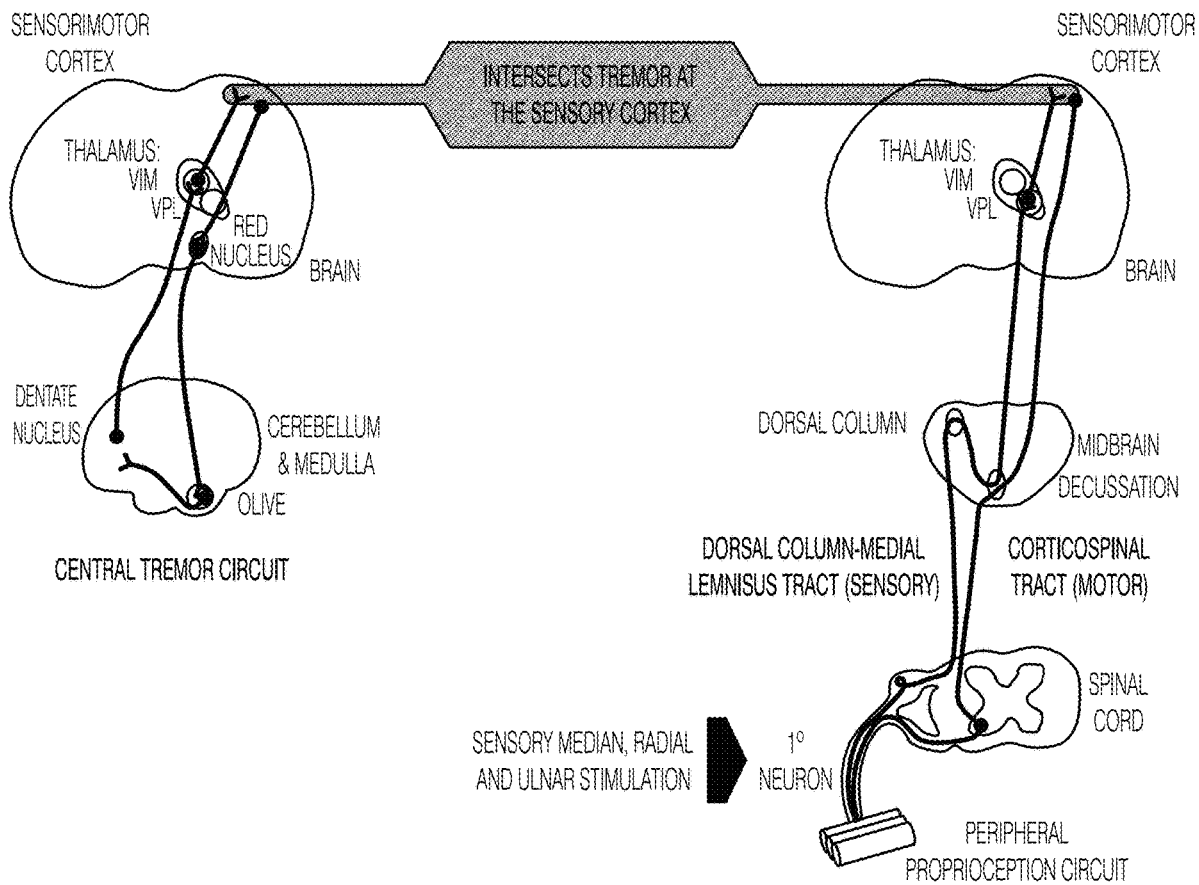
FIG. 2 illustrates how sensory stimulation from a peripheral nerve stimulation device intersects the tremor circuit in the central nervous system.
Figure 3A:
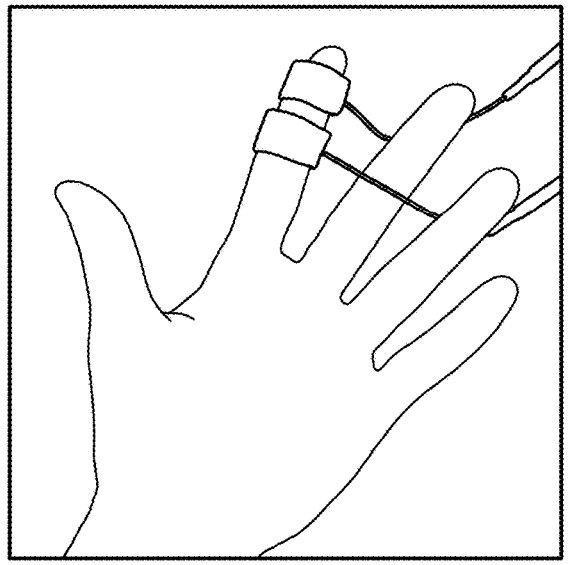
FIG. 3A illustrates an embodiment of a finger of a first patient being stimulated on the top and middle segments on the palmar side of the index finger with 1 cm×2 cm electrodes.
Figure 3B:
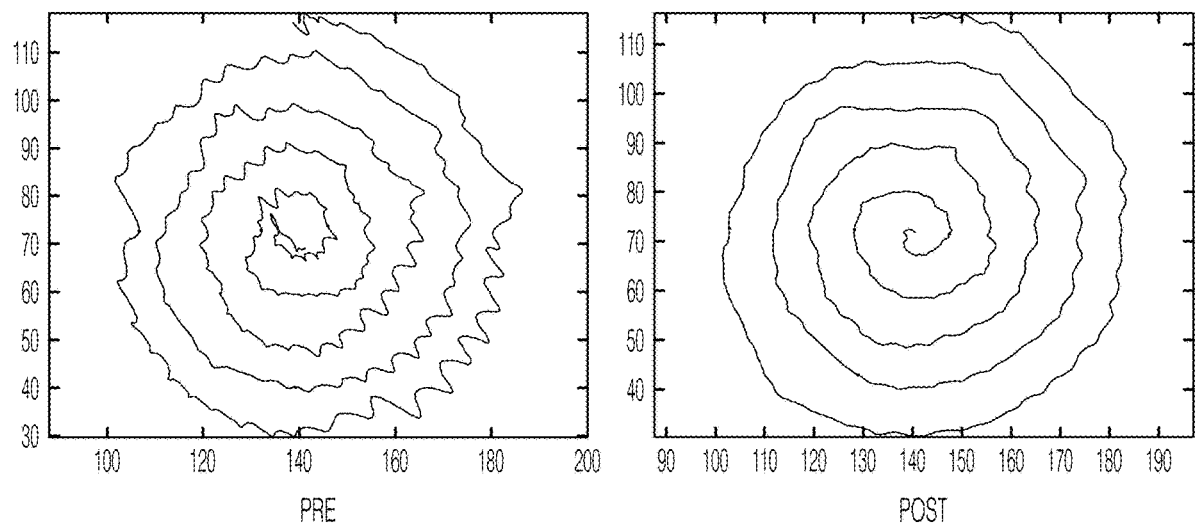
FIG. 3B illustrates spirals drawn by the first patient in FIG. 3A pre-stimulation and post-stimulation. Stimulation was constant 150 Hz bi-phasic waveform from an LGTech Elite device for 30 minutes.
Figure 4A:
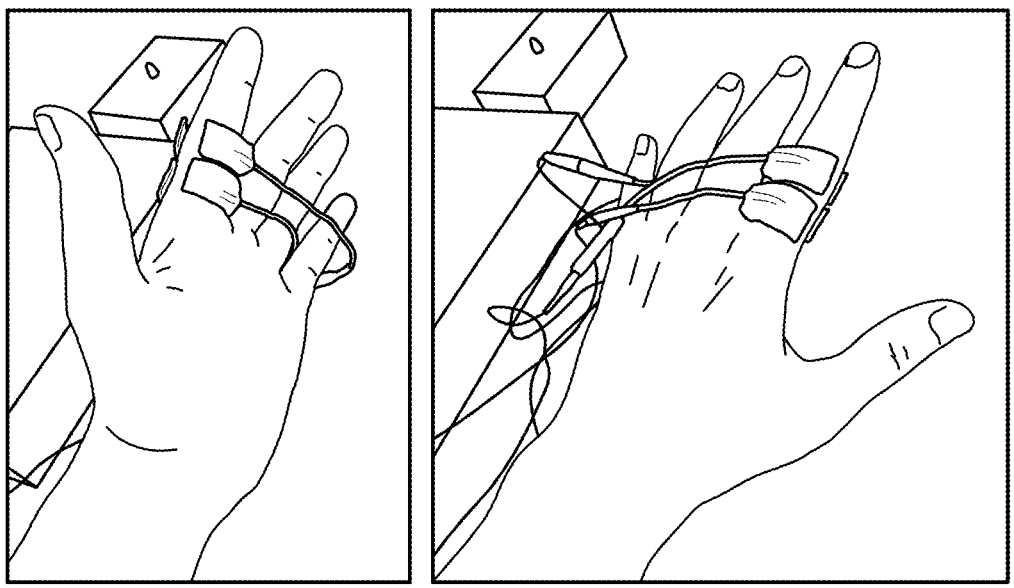
FIG. 4A illustrates an embodiment of a finger of a second patient being stimulated on the distal segment of the index finger with two 1 cm×2 cm electrode pairs, one on the palmar side and one on the dorsal side. Stimulation lasted 30 minutes and was a 150 Hz bi-phasic waveform that alternated between the electrode pairs at a frequency that matched the patient's measured tremor frequency.
Figure 4B:
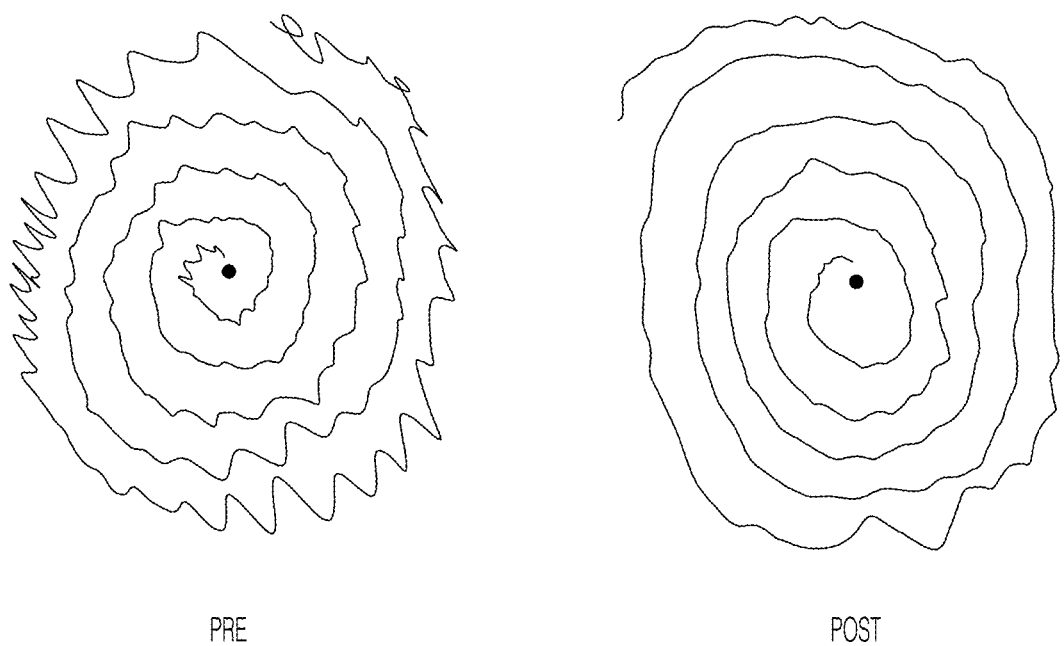
FIG. 4B illustrates spirals drawn by the second patient pre-stimulation and post-stimulation.
Figure 5A:
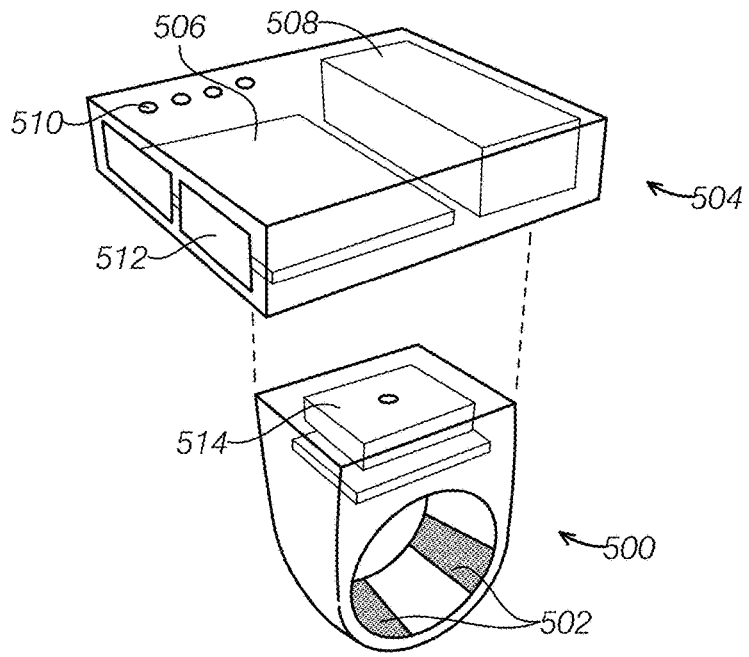
FIG. 5A illustrates an embodiment of a ring worn peripheral nerve stimulator with a RING unit to apply stimulation to the skin through electrode, which may also monitor tremor motion; and a stimulation unit that may contain an electrical stimulation signal generator, power source, and a microprocessor to control the stimulation.
Figure 5B:
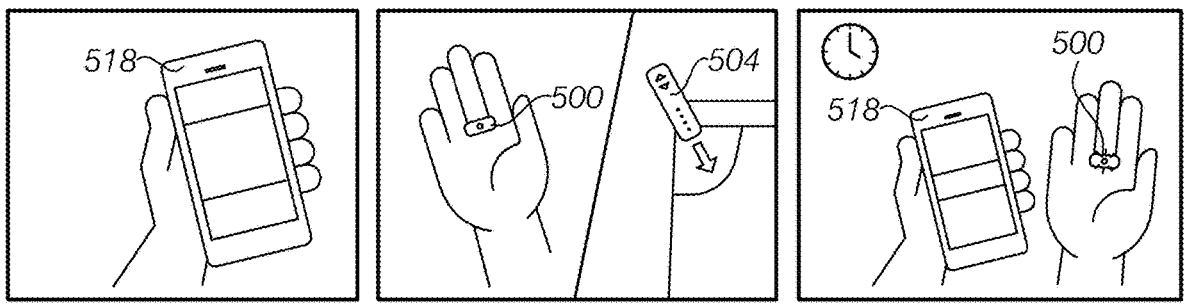
FIG. 5B illustrates how the ring and stimulation unit can be charged daily with a charging station and communicate with an external computing device, such as a smartphone or tablet, to store and analyze measured data, including stimulation parameters, and provide notifications to the ring wearer.

As shown in FIGS. 5A and 5B, one embodiment is a two-part system that includes 1) a ring-like unit 500 worn on the finger that contains electrodes 502 to transcutaneously apply electrical stimulation to the branches of the median, radial, and/or ulnar nerves in the finger, and 2) a detachable stimulation power unit 504 that may contain an electrical stimulation signal generator 506, power source 508, and/or a microprocessor to control the stimulation. The detachable stimulation power unit 504 can also have a user interface that can include a display, such as LEDs 510, and buttons 512 for entering inputs and adjusting stimulation parameters, such as amplitude. The stimulation power unit can connect directly through complementary contacts 514 on the ring-like unit 500 and/or a complementary receptacle on the stimulation power unit and/or wirelessly with the ring-like unit 500. FIG. 5B illustrates how the ring 500 and stimulation unit 504 can be charged daily with a charging station 516 and communicate wirelessly with an external computing device 518, such as a smartphone or tablet, to store and analyze measured data, including stimulation parameters, and provide notifications to the ring wearer.

Figure 7A:
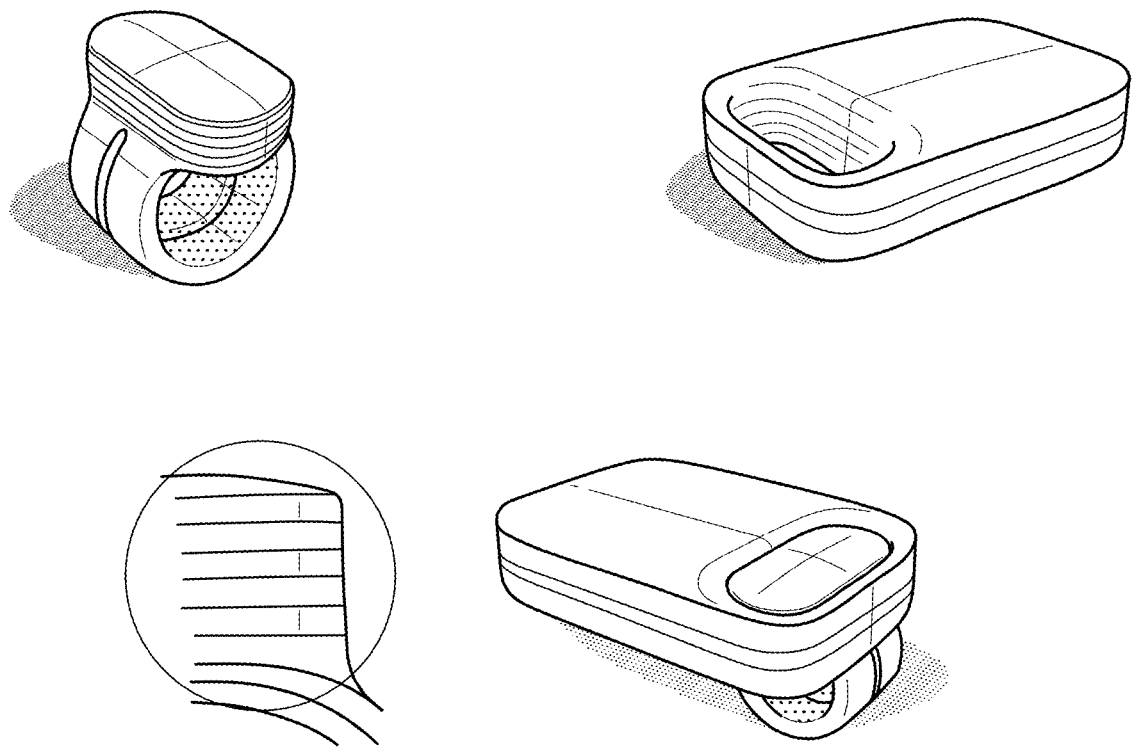
FIGS. 7A-7D illustrate additional embodiments of a ring unit and a stimulation unit.
Figure 7B:
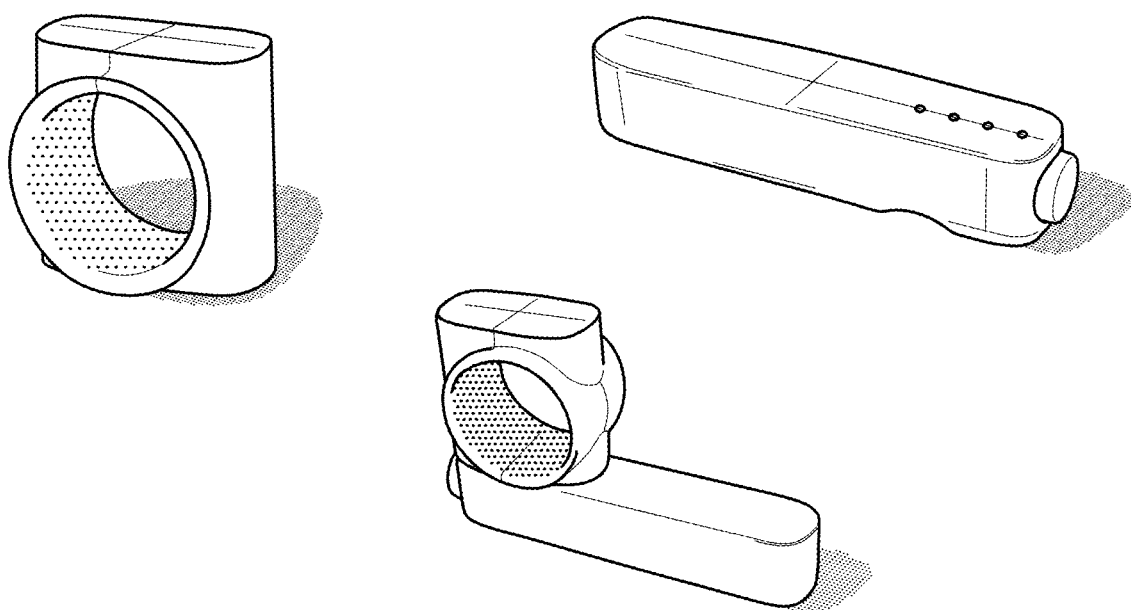
Figure 7C:
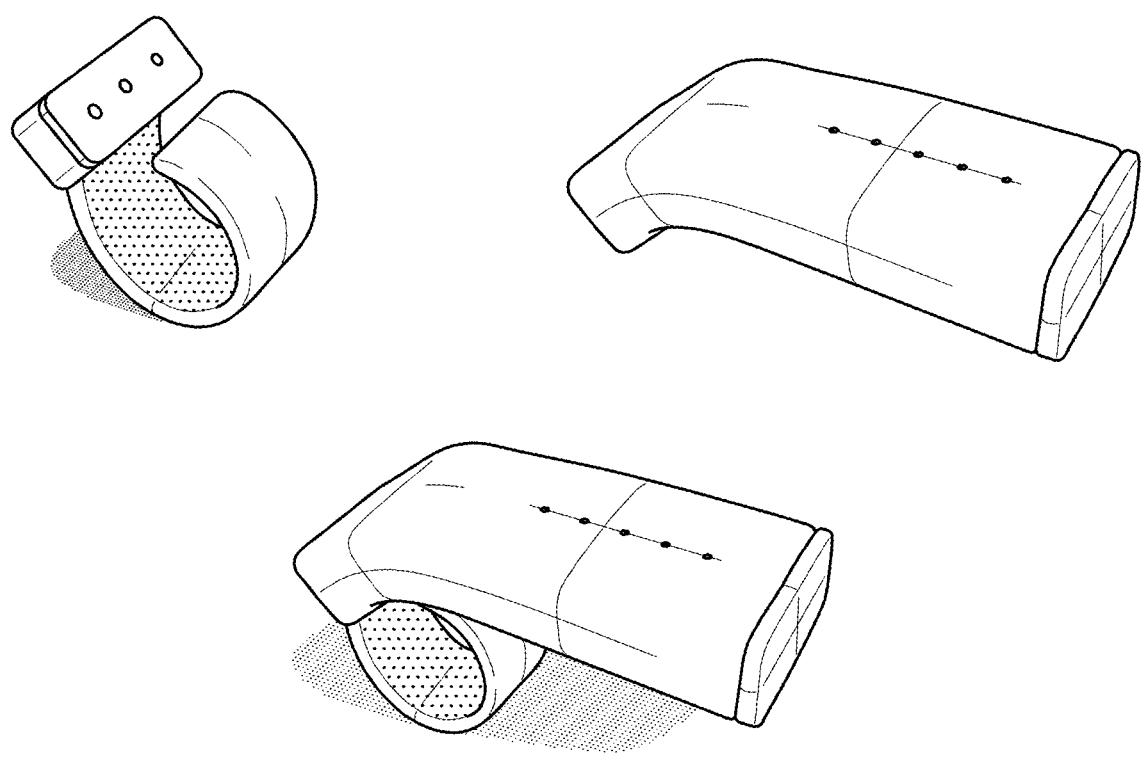
Figure 7D:
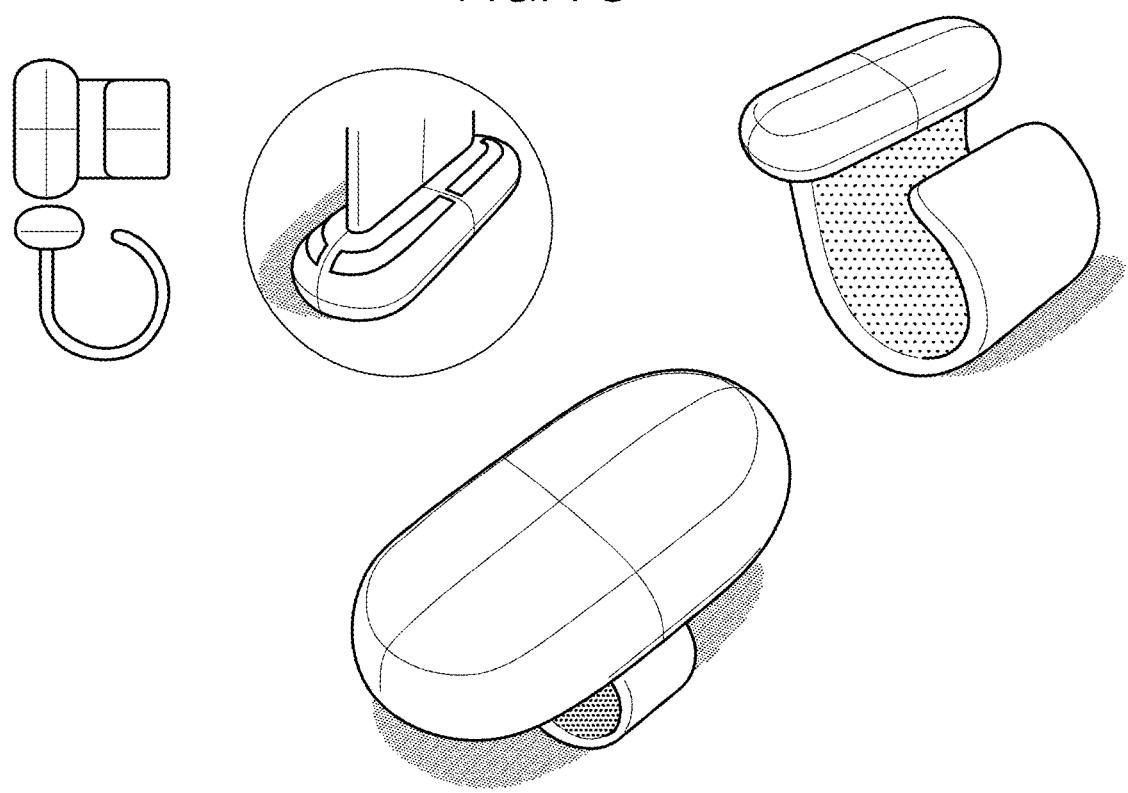
Figure 8A:
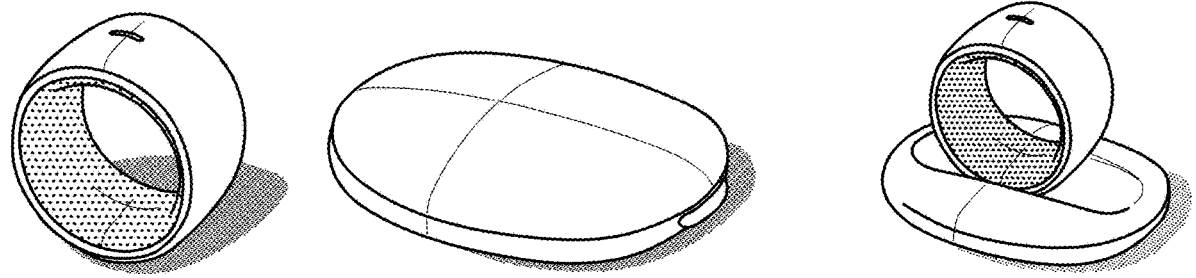
FIGS. 8A-8C illustrate additional embodiments of a ring unit and a stimulation unit.
Figure 8B:
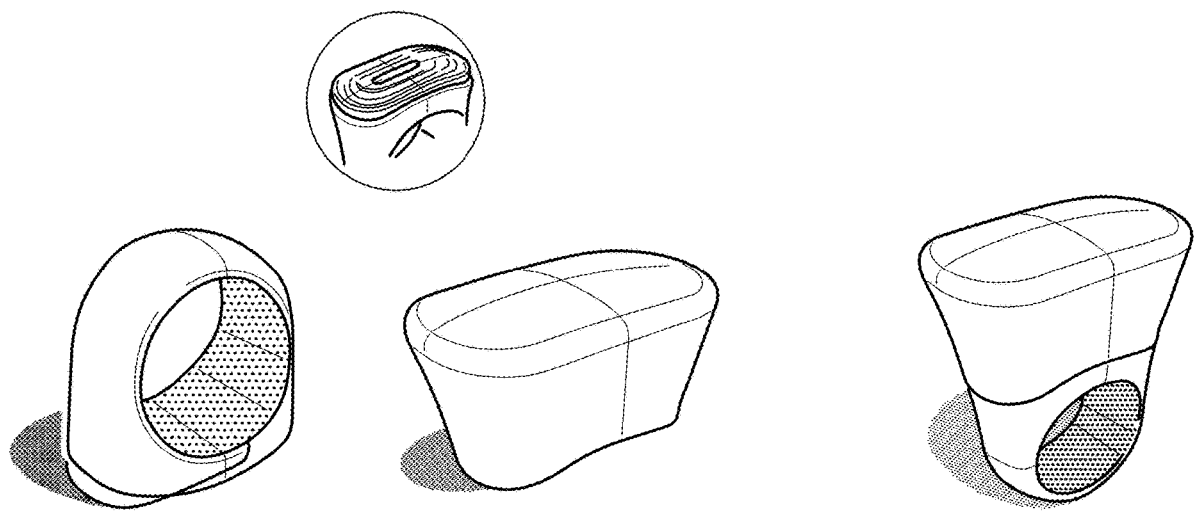
Figure 8C:
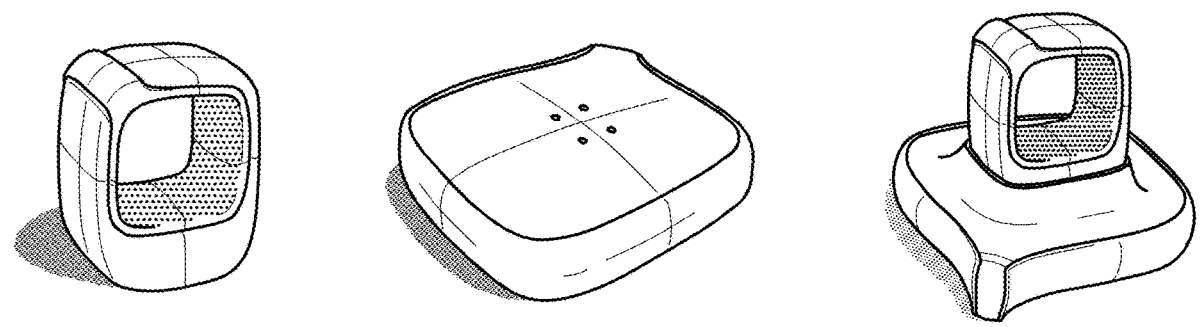

FIGS. 6A-D, FIGS. 7A-D, and FIGS. 8A-C show eleven variations of an embodiment of a two-part system that includes a ring-like unit and a stimulator unit. FIG. 7A shows a ring unit that has electrical contacts between the ring unit and stimulator that allow for two separate circumferential electrodes. FIGS. 7C-D show a ring-like unit where the mass of the ring rests at the crevice between two fingers and has an open band that is flexible to allow for variation in finger size.

In the above embodiment, the ring-like unit may contain sensors to measure tremor motion and activity using an inertial measurement unit (IMU), accelerometer, gyroscope, and/or magnetometer.

Figure 9A:
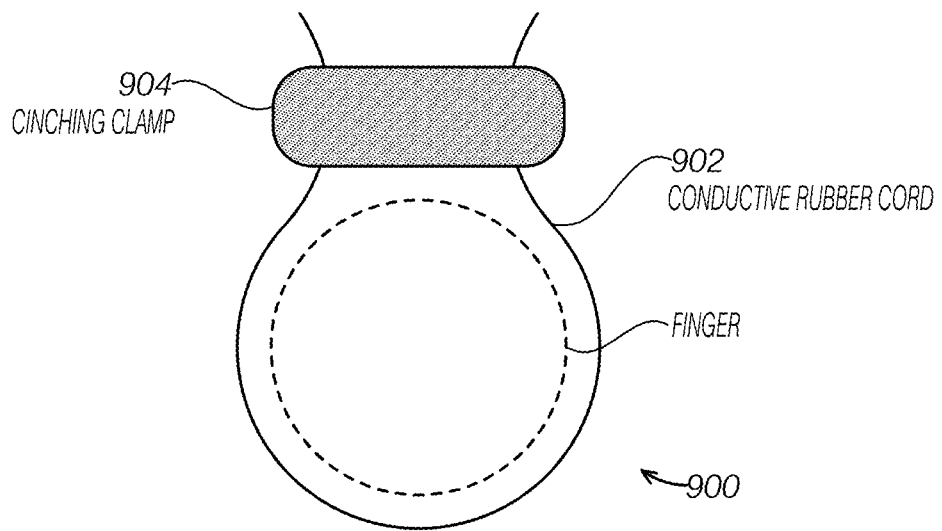
FIG. 9A illustrates an embodiment of a ring-like unit formed from a conductive rubber cord that can be cinched around a finger.
Figure 9B:
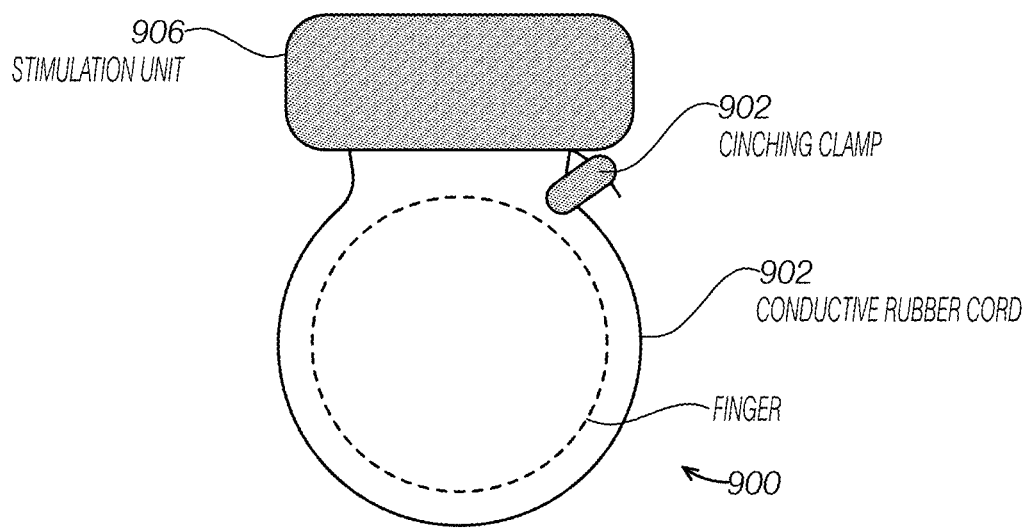
FIG. 9B illustrates the embodiment of the ring-like unit shown in FIG. 9A with a stimulation unit attached.

In any of the above embodiments, as shown in FIGS. 9A and 9B, the ring-like unit 900 may be a conductive rubber cord 902 or wire that is cinched, using a cinching claim 904 for example, to fit snuggly around the finger. The cinching rubber cord 902 may also attach a stimulation unit 906 that contain an electrical stimulation signal generator, power source, and/or a microprocessor to control the stimulation.

Figure 10:
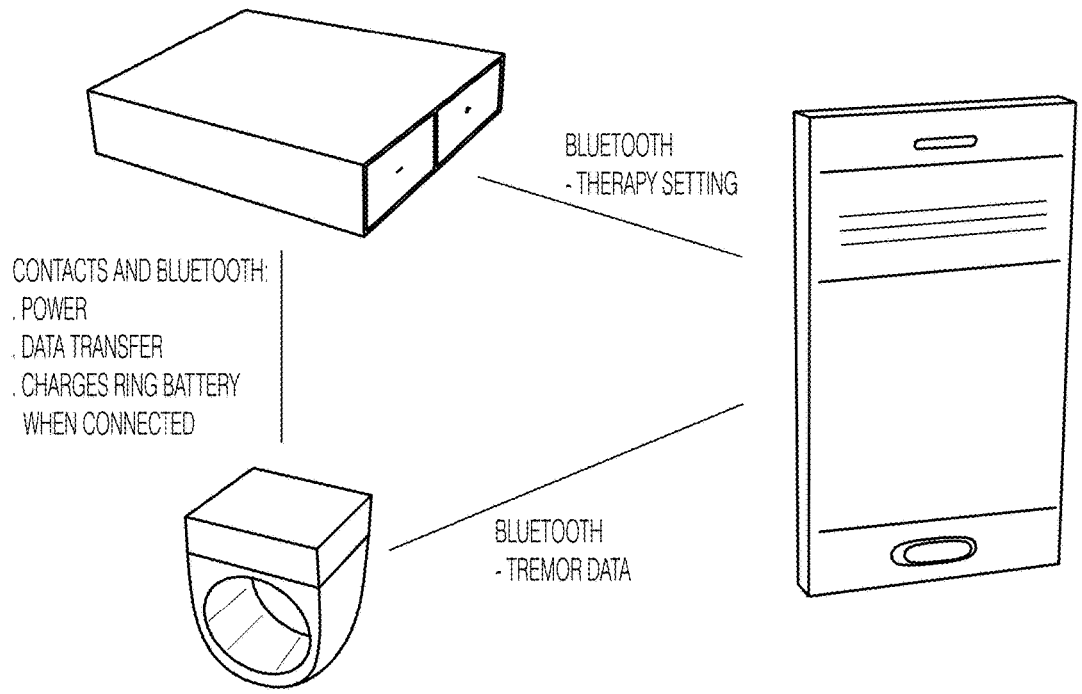
FIG. 10 illustrates an embodiment of the ring unit and the stimulation unit communicating with an external computing device, such as a smart phone and tablet, using wireless communication, such as low-energy Bluetooth.

In an extension of the above embodiment, as shown in FIG. 10, the ring unit 1000 and the stimulation unit 1002 may communicate with an external computing device 1004, such as a smart phone and tablet, using wireless communication, such as low-energy Bluetooth. The communication may also be tethered with a wired connection. Communication may be real time, at set intervals (e.g., hourly, daily, weekly), and/or when the devices are within range of each other.

Figure 11:
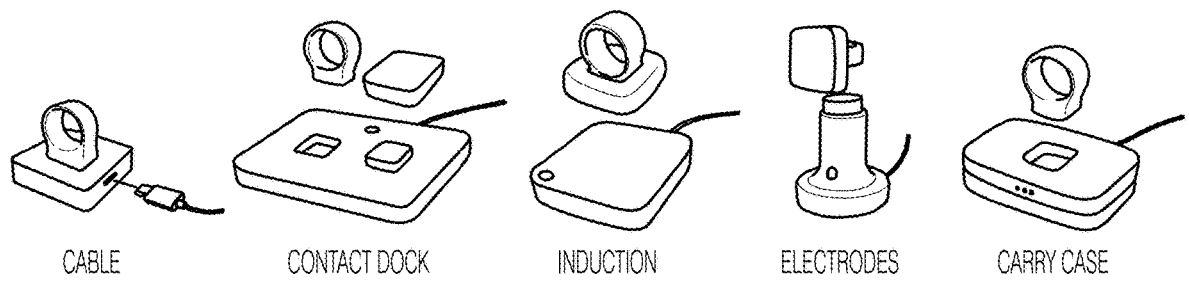
FIG. 11 illustrates embodiments for charging the ring and/or stimulation units when not being worn.

In the above embodiments, the ring unit 1000 and/or stimulation unit 1002 can be charged directly with a cable (e.g., micro USB), a contact dock 1006 with direct connection to the power source, inductive charging, direct contact with the stimulation electrodes (i.e., electrodes contact the charging station, which does not require a separate charging connection), and/or a separate carrying case, as shown in FIG. 11, that combines the above concepts on charging and data transfer.

Figure 12:
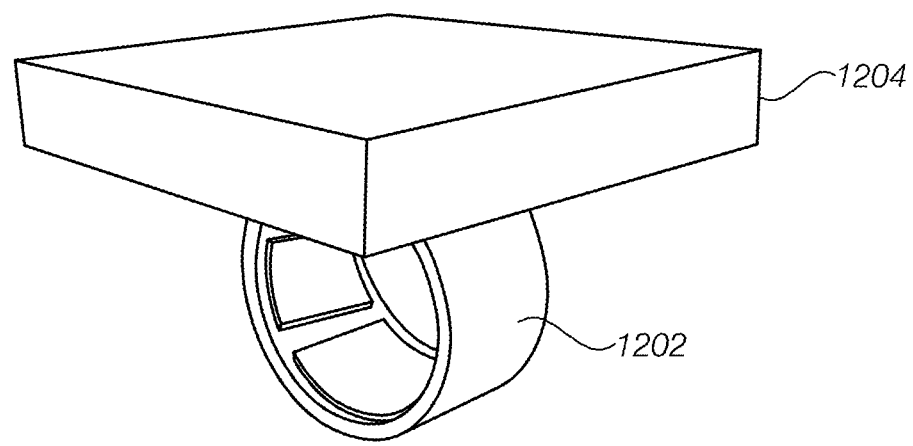
FIG. 12 illustrates an embodiment of a thin ring worn motion monitor and a separate ring worn stimulation unit that may contain an electrical stimulation signal generator, power source, and a microprocessor to control the stimulation.
Figure 12:
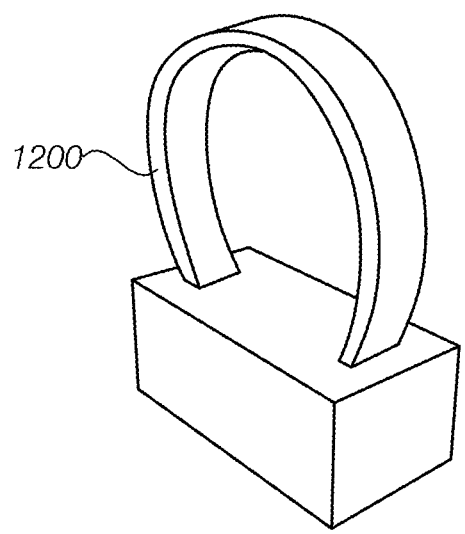
Figure 12:
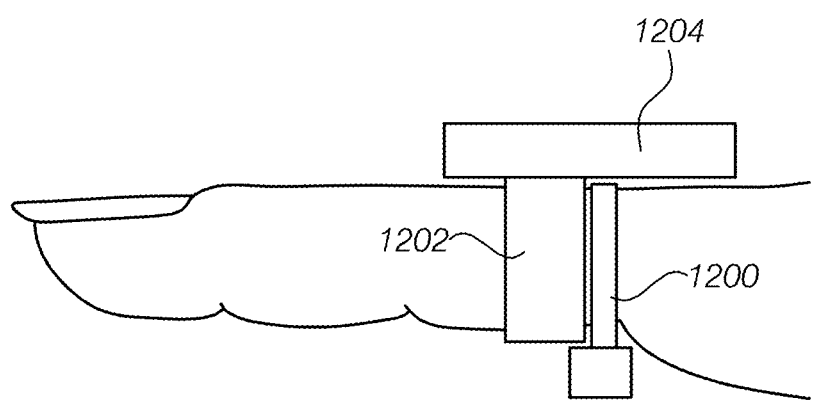

Another embodiment as shown in FIG. 12 is a two-part system that includes 1) a ring-like unit 1200 worn on the finger that contains sensors to measure tremor motion and activity using an inertial measurement unit (IMU), accelerometer, gyroscope, and/or magnetometer, and 2) a second ring-like unit 1202 that contains electrodes and applies transcutaneous electrical stimulation to the branches of the median, radial, and/or ulnar nerves in the finger, an electrical stimulation signal generator, a power source, and a microprocessor to control the stimulation. The stimulation unit 1204, which is attached to the second ring unit 1202 may also be permanently affixed to the ring unit 1200 that measures motion or may be detachable from one or both ring units.

Figure 13:
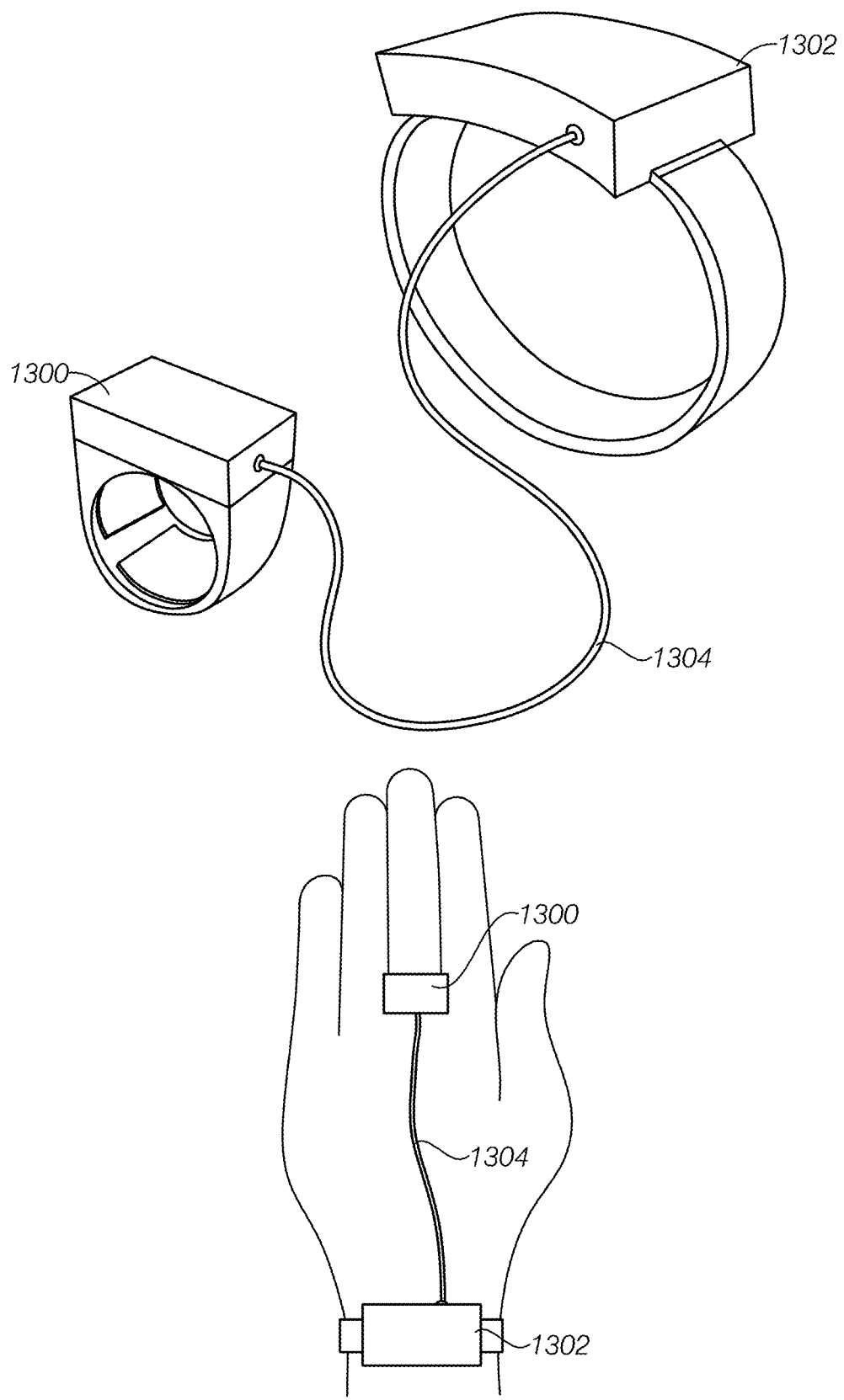
FIG. 13 illustrates an embodiment of a ring worn peripheral nerve stimulator with a ring to apply stimulation and monitor tremor motion; and a wrist worn stimulation unit that may contain an electrical stimulation signal generator, power source, and a microprocessor to control the stimulation. The wrist-worn stimulation unit is tethered by wire to the ring.

Another embodiment as shown in FIG. 13 is a two-part system that includes 1) a ring-like unit 1300 worn on the finger that contains electrodes to transcutaneously apply electrical stimulation to the branches of the median, radial, and/or ulnar nerves in the finger, and 2) a wrist-worn stimulation power unit 1302 that may contain an electrical stimulation signal generator, power source, and a microprocessor to control the stimulation. This wrist-worn power unit 1302 is tethered by wire 1304 to the ring-like unit 1300.

Figure 14:
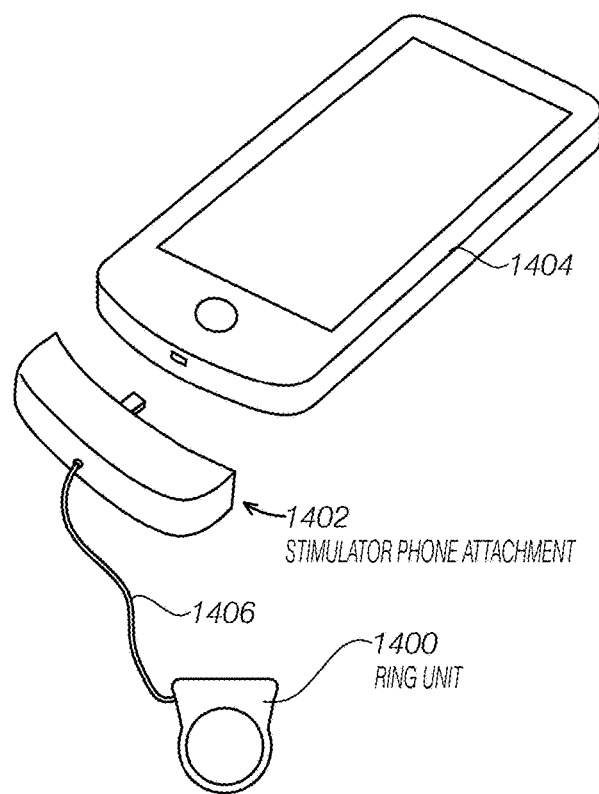
FIG. 14 illustrates an embodiment of a ring worn peripheral nerve stimulator that is connected to a smartphone or tablet through an attachment device. The ring could have minimal electronics to provide stimulation to the finger and the phone/attachment could house an electrical stimulation signal generator, power source, and a microprocessor to control the stimulation.

In another related embodiment as shown in FIG. 14, the ring unit 1400 could be attached to a non-wrist-worn (or worn device) device. Such a device could be an electronics unit 1402, such as a ring unit-phone adapter, that is connected to a mobile phone 1404 (e.g., different credit card readers). The advantage of the direct attachment to the phone is that additional electronics could be integrated into a phone case and power could be either be drawn from a separate battery hidden in the case or the phone itself. The ring unit 1400 can be tethered to the adapter through a wire 1406 which can transmit data and power from the phone to the ring unit. Additionally, this would allow easy access to the functionality of the phone, especially for services like per-treatment billing. While a phone may seem bulky, holding a phone during treatment could seem relatively normal and socially acceptable.

Figure 15:
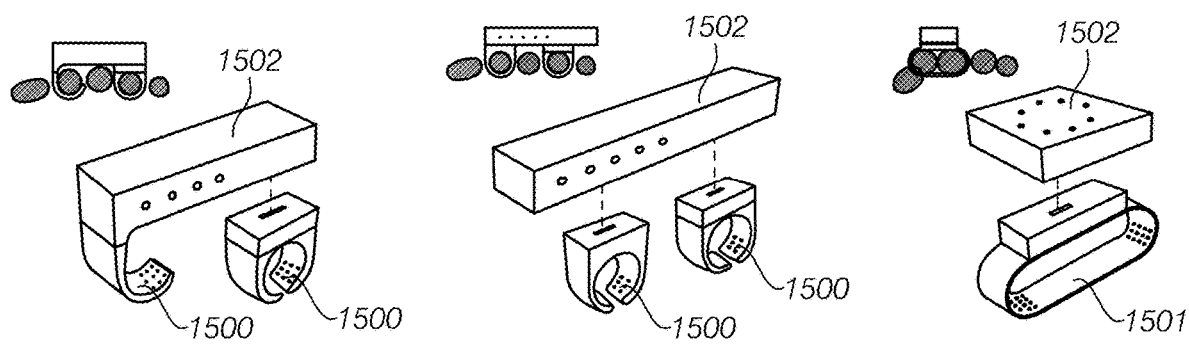
FIG. 15 illustrates an embodiment of a ring worn peripheral nerve stimulator and a stimulation unit that has multiple rings or a band that wraps the fingers to stimulate multiple fingers simultaneously.

In another embodiment as shown in FIG. 15, there could be two or three ring-like units 1500 connected with a stimulation unit 1502 to provide electrical stimulation to multiple fingers simultaneously. The ring-like unit 1501 could also be a band that wraps around multiple fingers. These ring-like units may contain electrodes to transcutaneously apply electrical stimulation to the branches of the median, radial, and/or ulnar nerves in the fingers. The stimulation unit may contain an electrical stimulation signal generator, power source, and a microprocessor to control the stimulation.

In another embodiment, the ring-like unit is a stand-alone device that has a motion monitor, electrodes, electrical stimulation signal generator, power source, and microprocessor to control the stimulation. The ring-like unit may provide transcutaneous stimulation to the branches of the median, radial, and/or ulnar nerves in the finger.

Figure 16A:
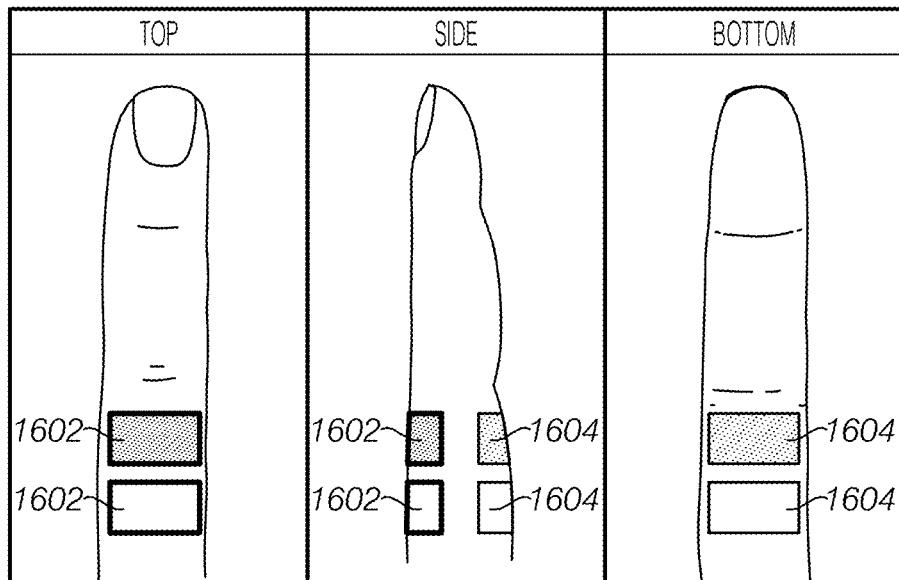
FIG. 16A illustrates an embodiment of a horizontal electrode configuration housed in a ring-like unit that provides electrical stimulation transcutaneously to nerves in the finger. This illustration is of an index finger with an electrode pair on the dorsal side to stimulate the radial nerve, and an electrode pair on the palmar side to stimulate the median nerve.
Figure 16B:
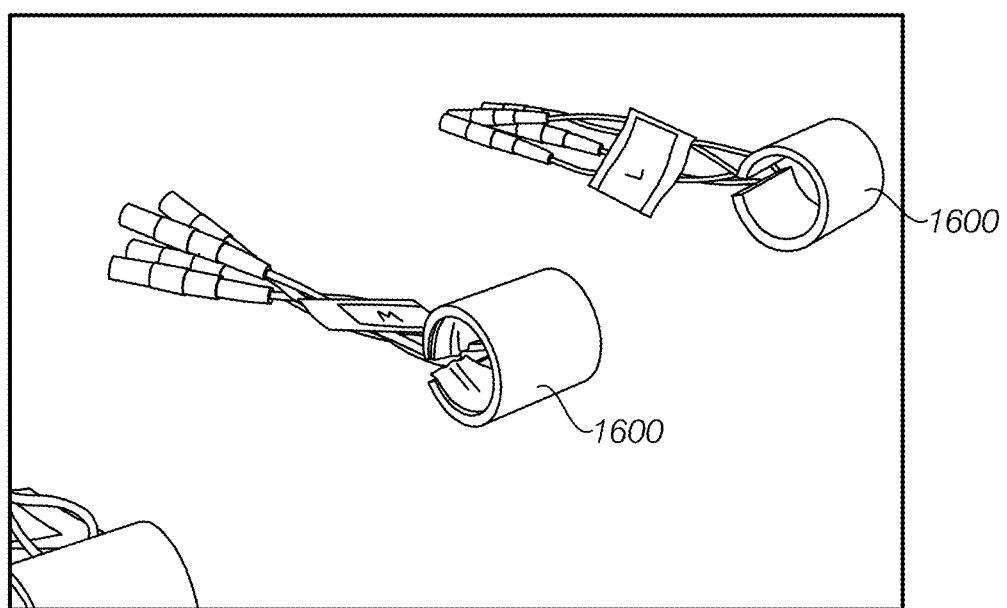
FIG. 16B illustrates embodiments of horizontal electrode configuration implemented in ring housings of different sizes. These electrode configurations were implemented and tested on three people, and paresthesia of the nerves was verified.

In another embodiment as shown in FIGS. 16A and 16B, the ring-like unit 1600 contains a horizontal electrode configuration to transcutaneously provide electrical stimulation to branches of the median, radial, and/or ulnar nerves in the finger (FIG. 16). There is an electrode pair 1602 on the dorsal side to stimulate the radial nerve, and an electrode pair 1604 on the palmar side to stimulate the median nerve. In the index figure, electrodes on the dorsal side stimulate the radial nerve, and electrodes on the palmar side stimulate the median nerve. These electrode configurations were implemented and tested on three people, and paresthesia of the nerves was verified.

Figure 17A:
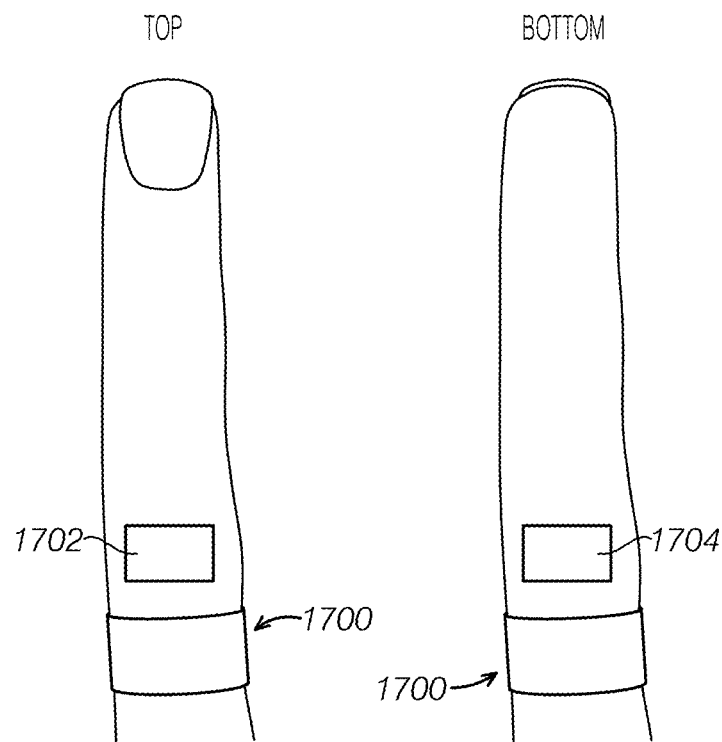
FIGS. 17A and 17B illustrate an embodiment of a horizontal electrode configuration with a single common ground electrode that wraps continuously around the finger. With the common electrode, the total electrode count is reduced to 3.
Figure 17B:
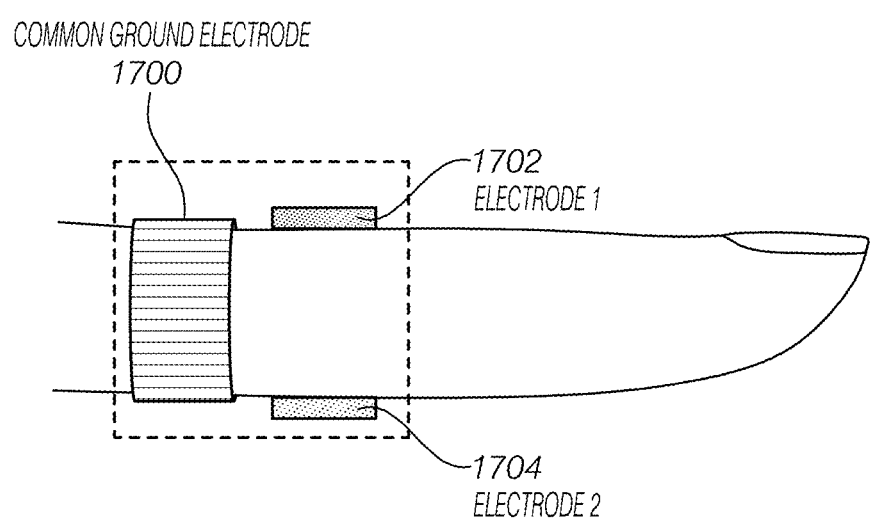
Figure 18A:
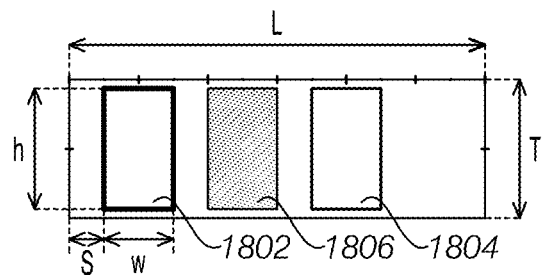
FIG. 18A-18D illustrate an embodiment of a vertical electrode configuration housed in a ring-like unit that provides electrical stimulation transcutaneously to nerves in the finger. This illustration is of an index finger with an electrode on the dorsal side to stimulate the radial nerve, and an electrode on the palmar side to stimulate the median nerve. These two electrodes share a common ground electrode that is oriented 90° between the other two electrodes. These electrode configurations were implemented and tested on three people, and paresthesia of the nerves was verified.
Figure 18A:
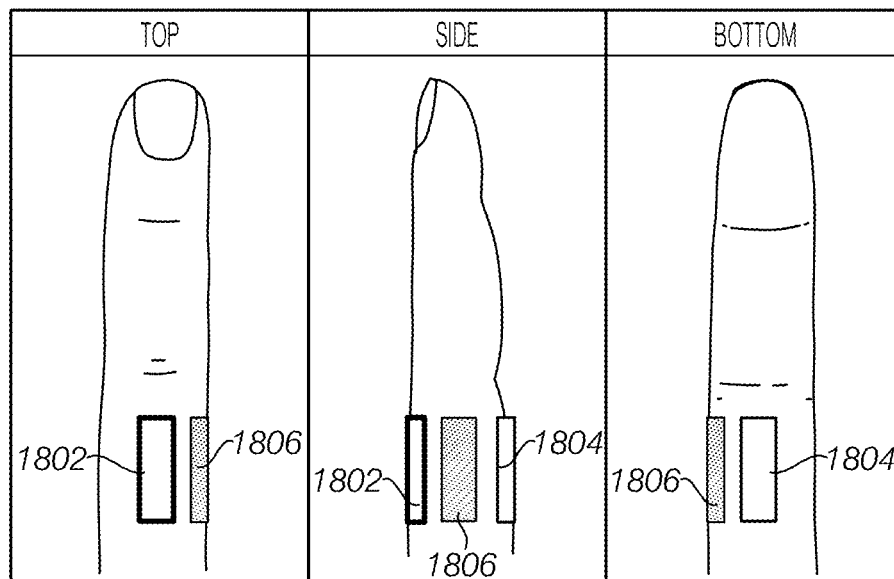
Figure 18A:
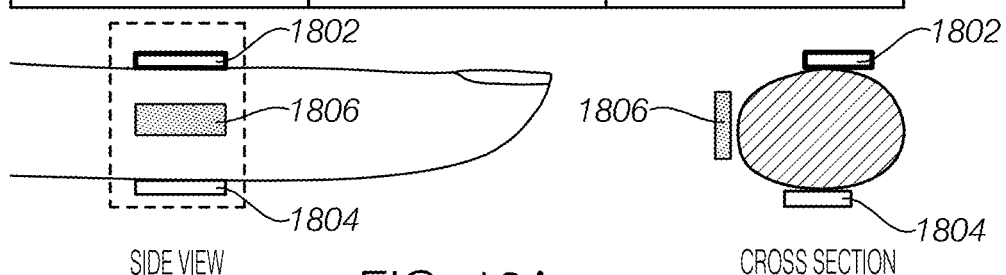
Figure 18B:
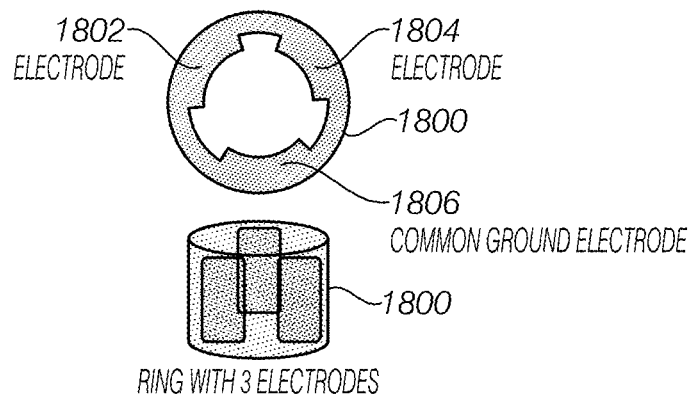
Figure 18C:
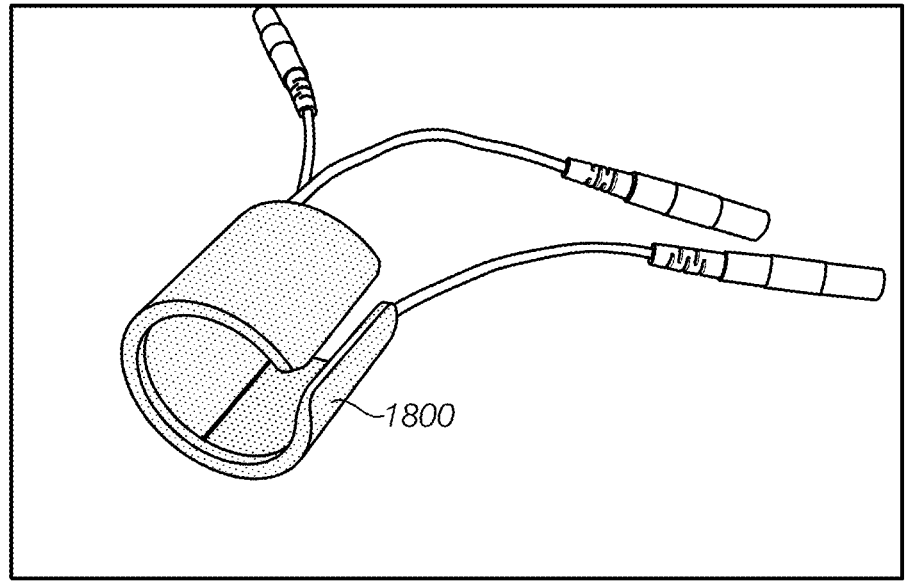
Figure 18D:
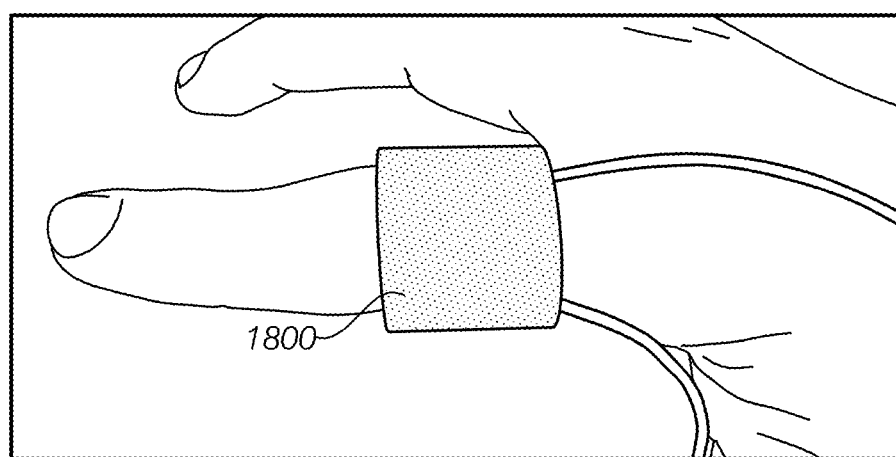

In another embodiment of the configuration above as shown in FIGS. 17A and 17B, a common electrode 1700 can be created out of two of the electrodes to reduce the total electrode count to 3 for a configuration that can stimulate a nerve on the dorsal side using a dorsal electrode 1702 and the common electrode 1700 and a nerve on the palmar side using a palmar electrode 1704 and the common electrode 1700. The common electrode can be a ring electrode that spans both sides of the finger, and as shown, the electrode pairs it forms are arranged longitudinally with respect to the finger.

In one embodiment as shown in FIGS. 18A-D, the ring-like unit 1800 contains a vertical or circumferential electrode configuration to transcutaneously provide electrical stimulation to the branches of the median, radial, and/or ulnar nerves in the finger. There is an electrode 1802 on the dorsal side to stimulate the radial nerve, and an electrode 1804 on the palmar side to stimulate the median nerve. These two electrodes share a common ground electrode 1806 that is oriented approximately 90° between the two electrodes. In the index finger, the electrode on the dorsal side stimulates the radial nerve, and the electrode on the palmar side stimulates the median nerve. These electrode configurations were implemented and tested on three people, and paresthesia of the nerves was verified.

Figure 19:
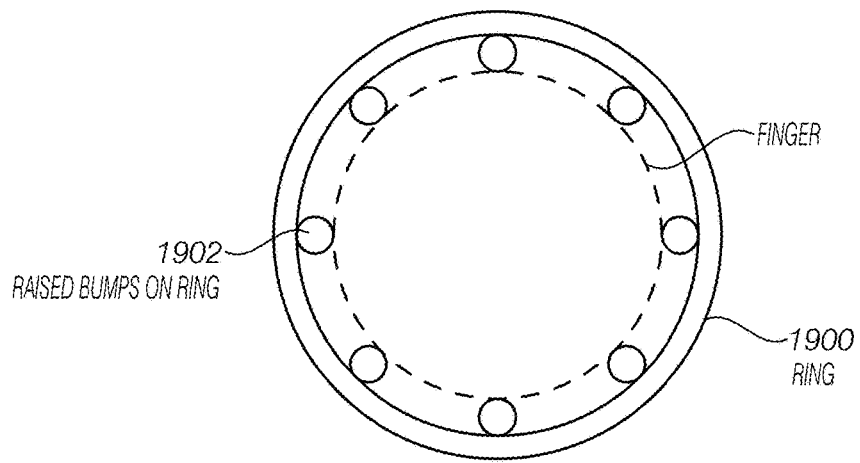
FIG. 19 illustrates an embodiment of a ring-like unit with bumps or contours on the inside surface to accommodate variation in finger size.

In one embodiment as shown in FIG. 19, the ring-like unit 1900 has bumps 1902 and contours on the inside surface of the ring. This allows better conformation to the skin to accommodate the natural variety in finger size between different people, or between different fingers on the same person. It also allows a single ring-like unit to tightly conform to a person's finger despite natural variations in finger size over time.

Figure 20:
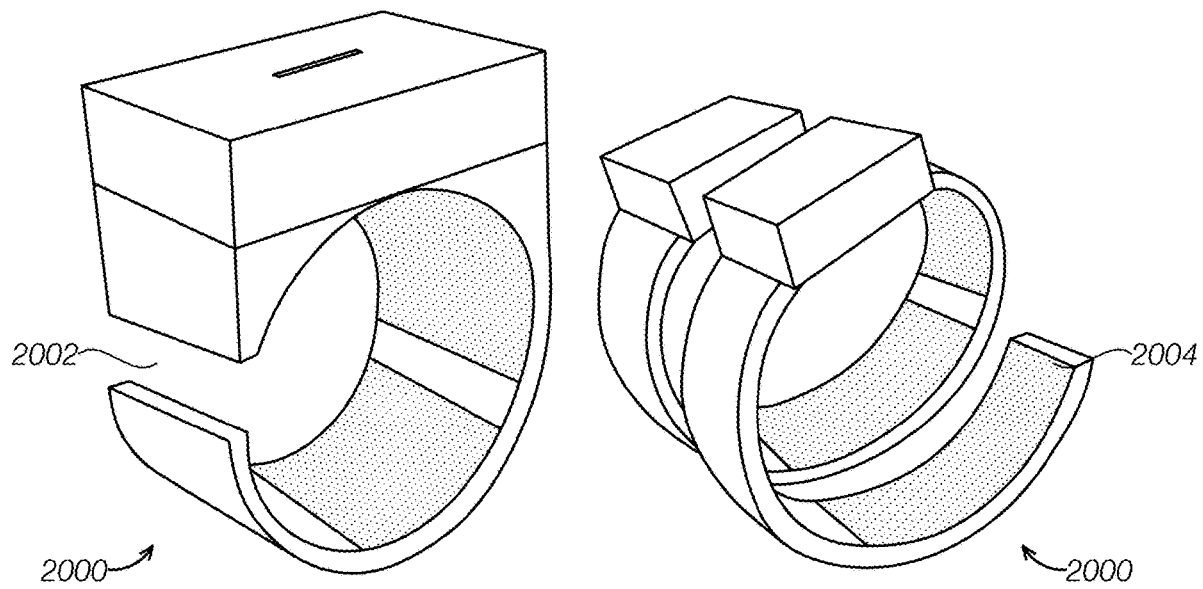
FIG. 20 illustrates an embodiment of a ring-like unit with a flexible form to accommodate variation in finger size.

In one embodiment as shown in FIG. 20, the ring-like unit 2000 may be flexible or manufactured from an elastic material, such as silicone, rubber, or elastic fabric. This allows better conformation to the skin to accommodate the natural variety in finger size between different people, or between different fingers on the same person. It also allows a single ring-like unit to tightly conform to a person's finger despite natural variations in finger size over time. The ring can have a slit 2002 or be formed from a spiral 2004 that facilitates the increase in ring diameter when needed.

Figure 21:
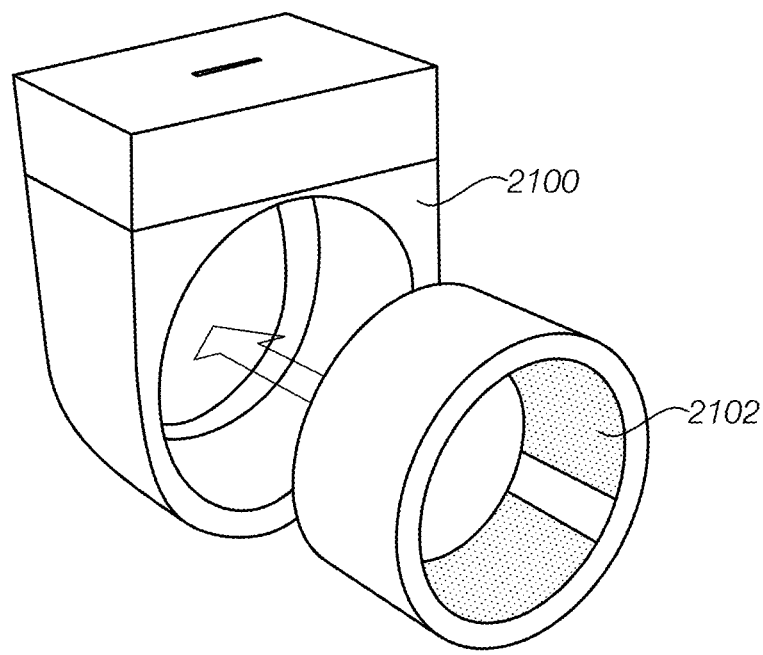
FIG. 21 illustrates an embodiment of a ring-like unit with inserts to accommodate variation in finger size.

In one embodiment as shown in FIG. 21, the ring-like unit 2100 could have separate, multiple inserts 2102 to accommodate variations in finger size. This allows better conformation to the skin to accommodate the natural variety in finger size between different people, or between different fingers on the same person. Thicker inserts can be used for people with small fingers, and thinner inserts can be used for people with large fingers. It also allows a single ring-like unit to tightly conform to a person's finger despite natural variations in finger size over time. The inserts 2102 can have electrodes and electrical contacts for electrically coupling with the ring unit.

Figure 22:
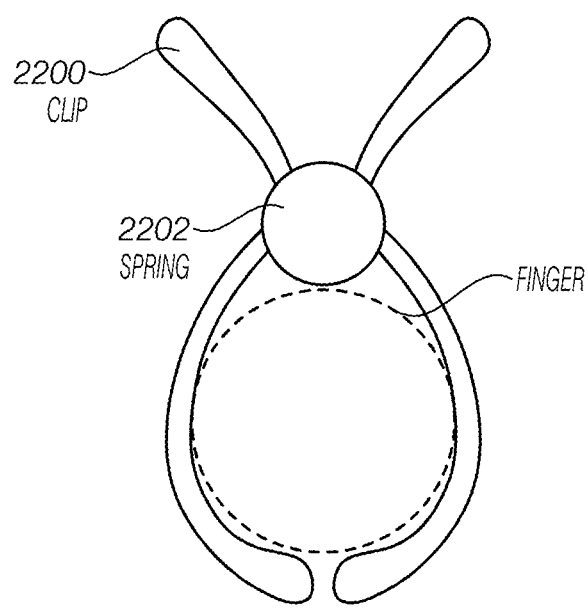
FIG. 22 illustrates an embodiment of a ring-like unit as a c-clip with a spring hinge to accommodate variation in finger size and improve ease of attaching the device to the finger.

In one embodiment as shown in FIG. 22, the ring-like unit 2200 could be in the shape of a C-clip with spring hinge 2202 that allows the device to be attached over the finger and would not require specific ring sizing. The spring-hinge would apply a small amount of pressure through the clip to ensure good conformance and contact between the electrodes and the skin. The c-clip could also be easier for people to attach to their finger, especially people with hand tremors. This allows better conformation to the skin to accommodate the natural variety in finger size between different people, or between different fingers on the same person. It also allows a single ring-like unit to tightly conform to a person's finger despite natural variations in finger size over time. Additionally, the clip could attach to the distal end of the finger (i.e., the fingertip, similar to a pulse-oximeter), as early experiments previously described show that top and middle segments can be used to successfully stimulate nerves in the finger.

Figure 23:
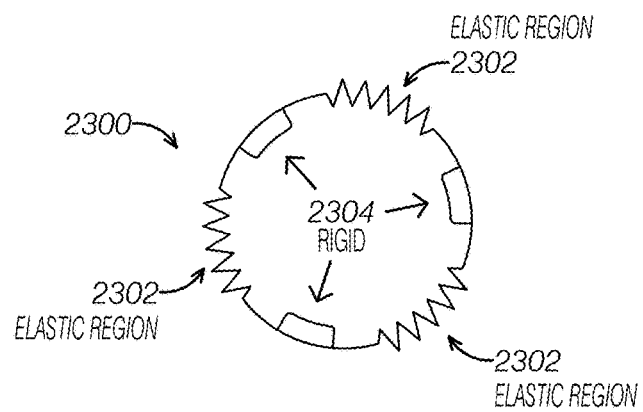
FIG. 23 illustrates an embodiment of a ring-like unit with elastic material connecting the electrodes together around the finger.

In another embodiment as shown in FIG. 23, the ring 2300 could contain neighboring regions of elastic 2302 and nonelastic 2304 materials. The nonelastic regions could contain the electrode areas while the elastic regions allow better conformance to the finger size. This is analogous to what is done in children's pants to accommodate different waist sizes.

In another embodiment, the ring-like unit connects wirelessly (e.g., low-energy Bluetooth) or is physically tethered to an external device that contains an electrical stimulation signal generator, power source, and a microprocessor to control the stimulation, such as a smart phone or tablet. The ring-like unit would transcutaneously provide electrical stimulation to the branches of the median, radial, and/or ulnar nerves in the finger.

Figure 24:
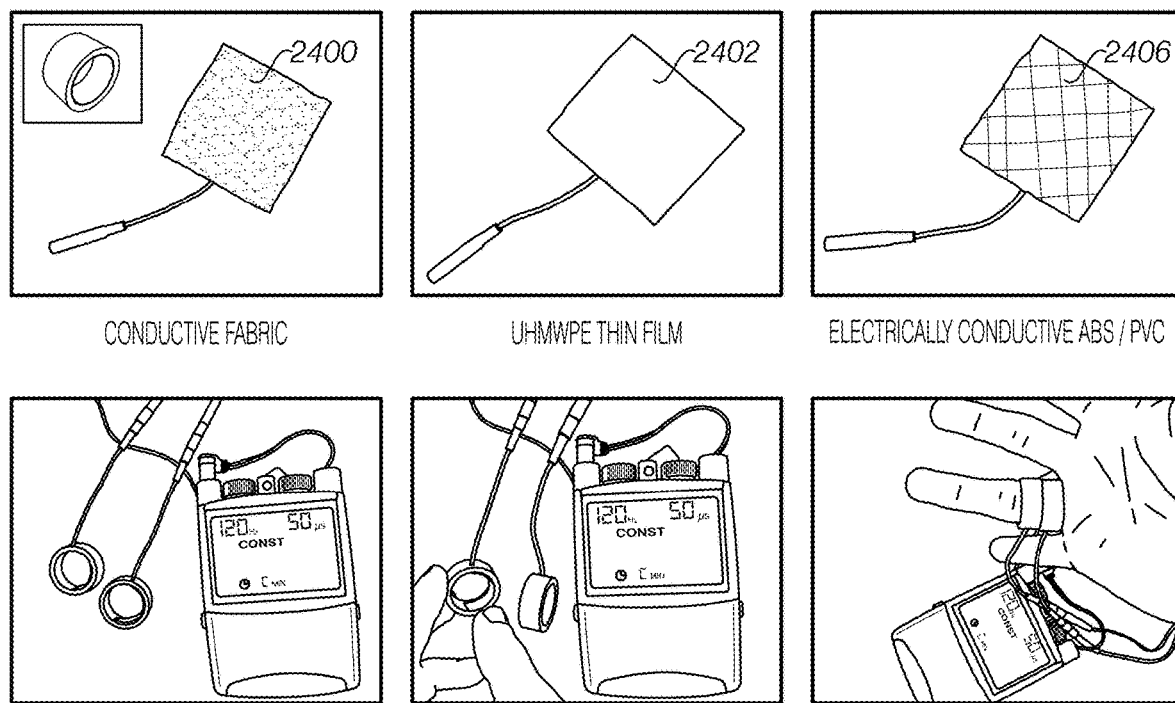
FIG. 24 illustrates various embodiments of dry-contact electrodes housed in a ring-like unit. Top panel shows three different dry electrode materials, and bottom panel shows implementation of a dry electrode ring with a thin-film ultra-high molecular weight polyethylene (UHMWPE).

In some embodiments as shown in FIG. 24, the electrodes could be dry-contact 2400 (e.g., fabric or silicone impregnated with conductive fillers such as carbon or silver particles, thin-film carbon-doped UHMWPE polymer 2402, conductive ABS/PC polymer 2404, a conductive gel (e.g., hydrogels), a wet electrode surface (e.g., a sponge with water or conductive liquids), or fine micro needles. In some embodiments, dry electrodes can be made to have better contact by attaching them to a springy/spongy surface. This produces a comfortable, conformal surface. For example, a stainless steel fabric could be sewn to a neoprene rubber. The neoprene will have enough stretch and give to allow conformance to the surface.

Figure 25:
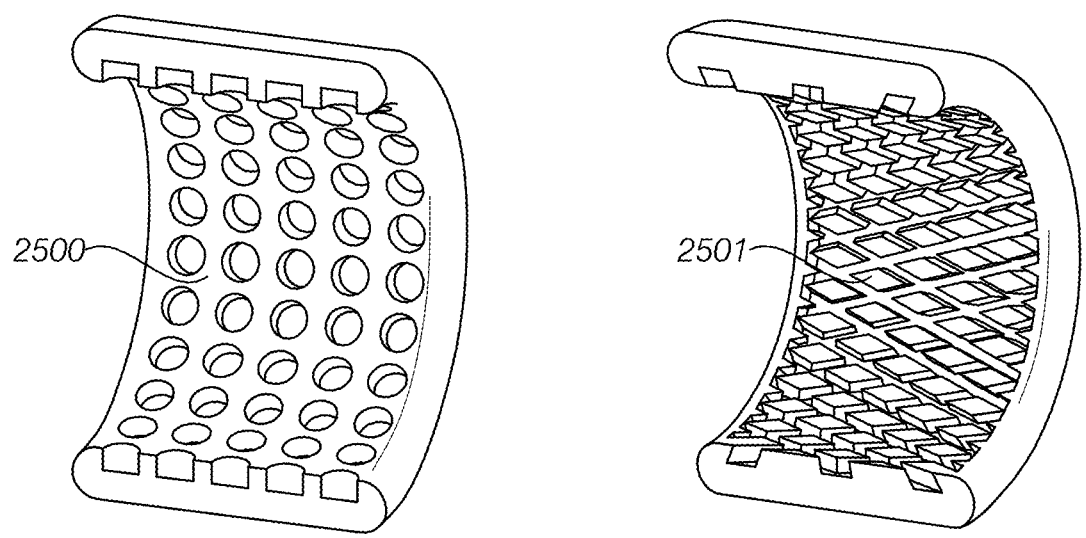
FIG. 25 illustrates a cross-sectional view of an embodiment of a ring-like unit with textured surface for capturing moisture. Moisture can improve the conductivity of the stimulation. These textured surfaces were created—when worn and run under water the units retained moisture for at least 30 minutes.

In some embodiments as shown in FIG. 25, the electrodes in a ring-like unit could have textured surfaces 2500, 2501 that trap moisture from the skin, air, or some external source, such as a sink. Moisture can improve the conductivity of the stimulation. These illustrated textured surfaces were created in ring-like units that when worn and run under water. These units retained moisture for at least 30 minutes. The ring-like unit could also have a dry contact electrode with a similar textured surface.

In some embodiments, the electrodes could be a wicking fabric impregnated with conductive fillers or fibers. The wicking fabric would draw moisture from the skin or from the surrounding air (e.g., humidity) to improve conductivity of the stimulation.

Figure 26:
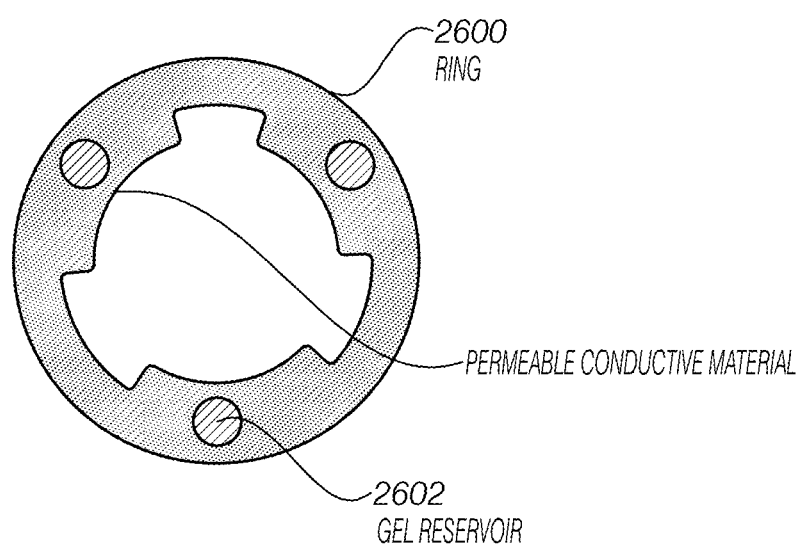
FIG. 26 illustrates an embodiment of a ring-like unit that contains a reservoir for conductive gel or liquid with a permeable membrane to slowly release the gel or liquid to the electrode-skin interface to improve stimulation conductivity.

In some embodiments as shown in FIG. 26, the ring-like unit 2600 could contain a reservoir 2602 or a plurality of reservoirs for a conductive gel or liquid that is slowly released through a permeable membrane. Fluid flow could be driven by gravity or by pressure applied to the ring manually, or from placing the ring on the finger. The reservoir could be filled by the wearer through an opening on the ring; or the reservoir could contain a wicking material that draws moisture from the skin or surrounding air.

In some embodiments, the wearable tremor monitor can use a plurality of sensors to collect, store, and analyze biological measures about the wearer including, but not limited to, motion (e.g., accelerometers, gyroscopes, magnetometer, bend sensors, barometer, altimeter), cardiovascular measures (e.g., heart rate, heart rate variability, blood pressure, cardiac output), skin conductance (e.g., skin conductance response, galvanic skin response), skin temperature, and sleep state (e.g., awake, light sleep, deep sleep, REM). In particular, studies have shown that increased stress levels can increase tremor in people with essential tremor, Parkinson's disease, and other diseases causing tremor. Thus, using statistical analysis and data mining techniques, including, but not limited to, logistic regression, linear regression, support vector machines, and Naïve Bayes classifiers, these biological measures can be analyzed to assess a person's state, including, but not limited to, stress level. This, in turn, can serve as a predictor for fluctuations in tremor level. In an early pilot study, patients were asked to perform activities prior to and after a stressful event. In this case, the stressful event was to take a timed math test. In preliminary studies, the patients' amplitude of tremor appeared to increase by about 20% after the stressful timed math test.

The wearable tremor monitor can have a microprocessor to analyze biological measures about the wearer to: determine or predict the onset of increased tremor activity, set parameters of the stimulation waveform applied by the stimulation unit, and/or adapt the stimulation waveform applied by the stimulation unit in real time. Parameters of the stimulation waveform that could be modified based on analysis of biological measures, include, but are not limited to, frequency, amplitude, shape, and burst sequence.

In one embodiment of the system, the wearable tremor monitor automatically detects and records stimulation usage to (1) track therapy compliance, (2) combine with the measurement of tremor activity to assess therapeutic effectiveness, and (3) determine or predict the onset of an increase or decrease in tremor activity.

In some embodiments, the wearable tremor monitor can have a visual, auditory, tactile (e.g., squeezing band), or vibrotactile cues to notify the wearer of key events based on analysis of biological measures, including, but not limited to, prediction of tremor onset, increase in tremor activity, and/or increase in stress level. The cuing system could also notify the wearer of other predetermined events or reminders set by the wearer. The cuing system is used to communicate information to the wearer, such as onset of increased tremor activity or other predetermined events in a more discreet, personalized way, without drawing attention from others in social situations.

In one embodiment, the wearable monitor can have a processing unit that collects, stores, processes, and analyzes the biological measures, along with other data input by the wearer.

In some embodiments, the wearable monitor can take user input about events, including diet history, medication history, caffeine intake, alcohol intake, etc. The monitor can use accelerometers to measure specific movements, gestures, or tapping patterns to record user inputs at specific prompts. Other touch sensors, such as resistive strips or pressure sensitive screens, or accelerometer and gyroscopes could be used to measure specific gestures, movements, or tapping to record user inputs. These gesture based measures to record user input minimized the complexity of steps required to input user data into the device. The data can be stored in memory and processed by the processing unit. In some embodiments, the data can be transmitted from the wearable monitor to an external computing device, such as a smartphone or a tablet.

In one embodiment, the wearable monitor can connect with other applications, such as calendars and activity logs to sync and track events, or a saved calendar can be saved and stored on the device. In some embodiments, the wearable monitor can communicate with a variety of computing devices, such as a smart phone, tablet, laptop, or desktop computer that have the appropriate software.

Figure 5B:
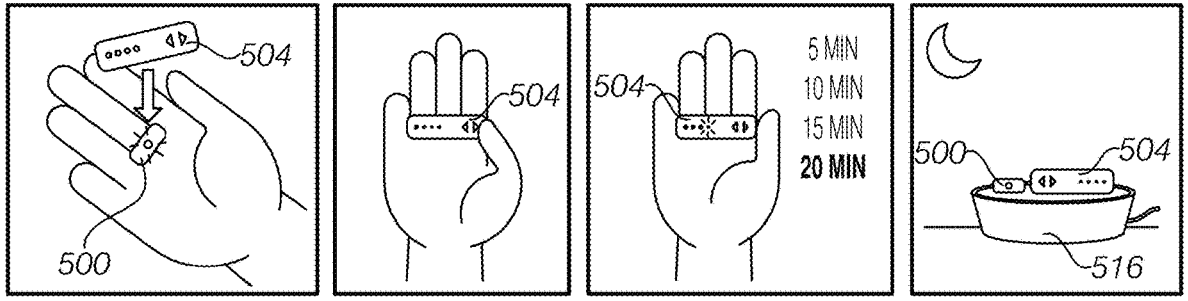
Figure 6A:
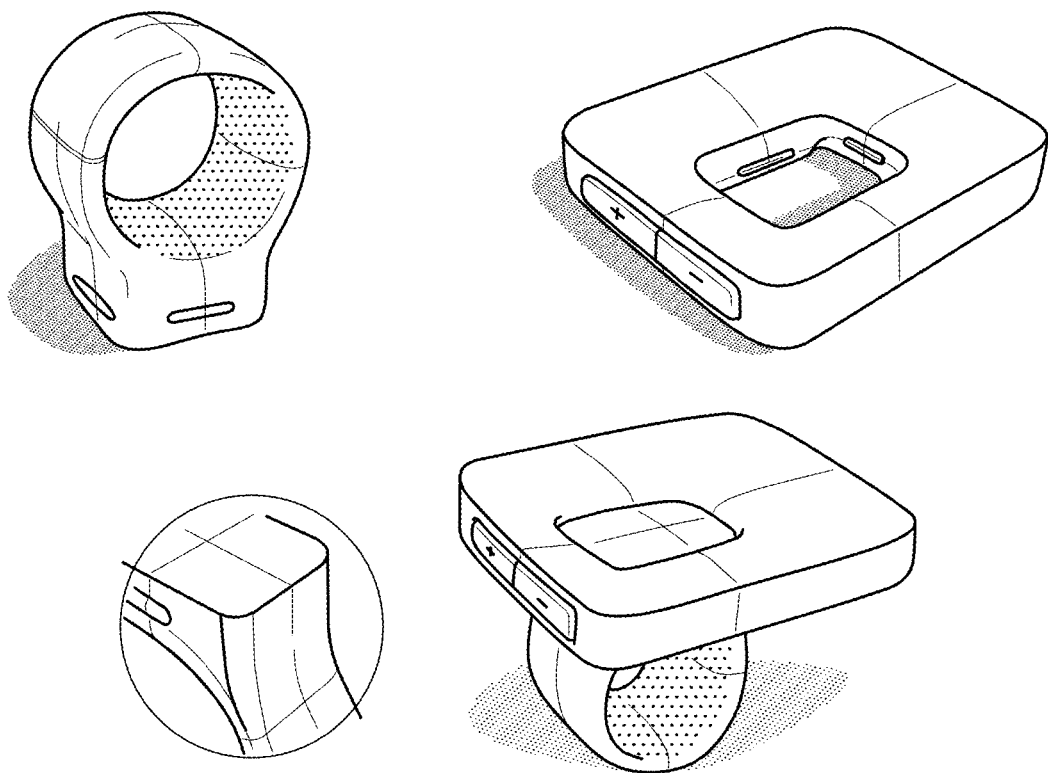
FIGS. 6A-6D illustrate various embodiments of a ring unit and a stimulation unit.
Figure 6B:
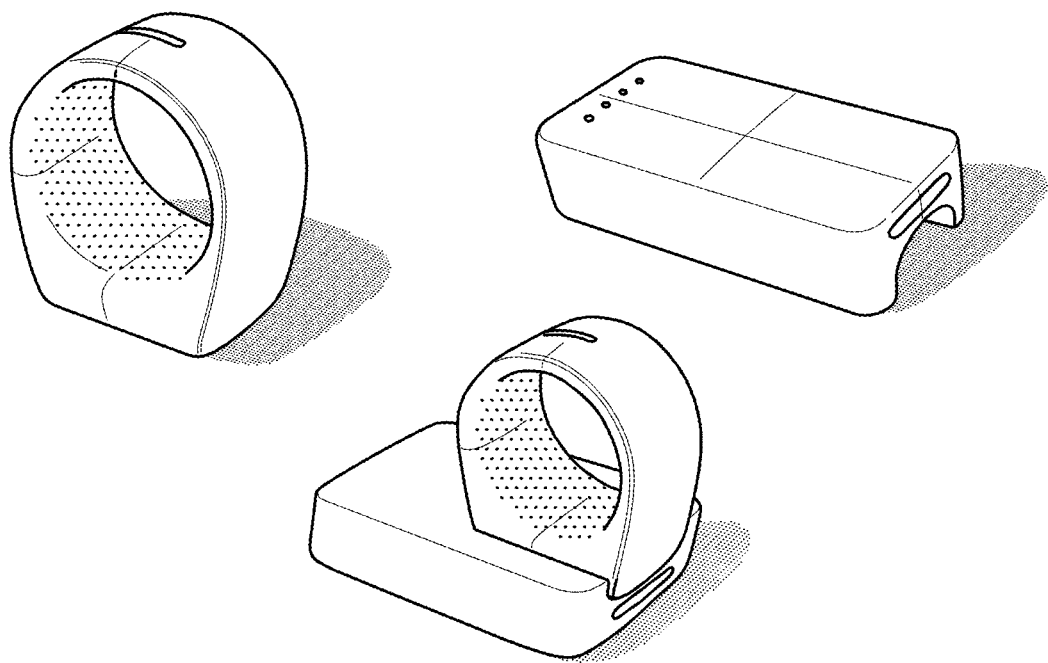
Figure 6C:
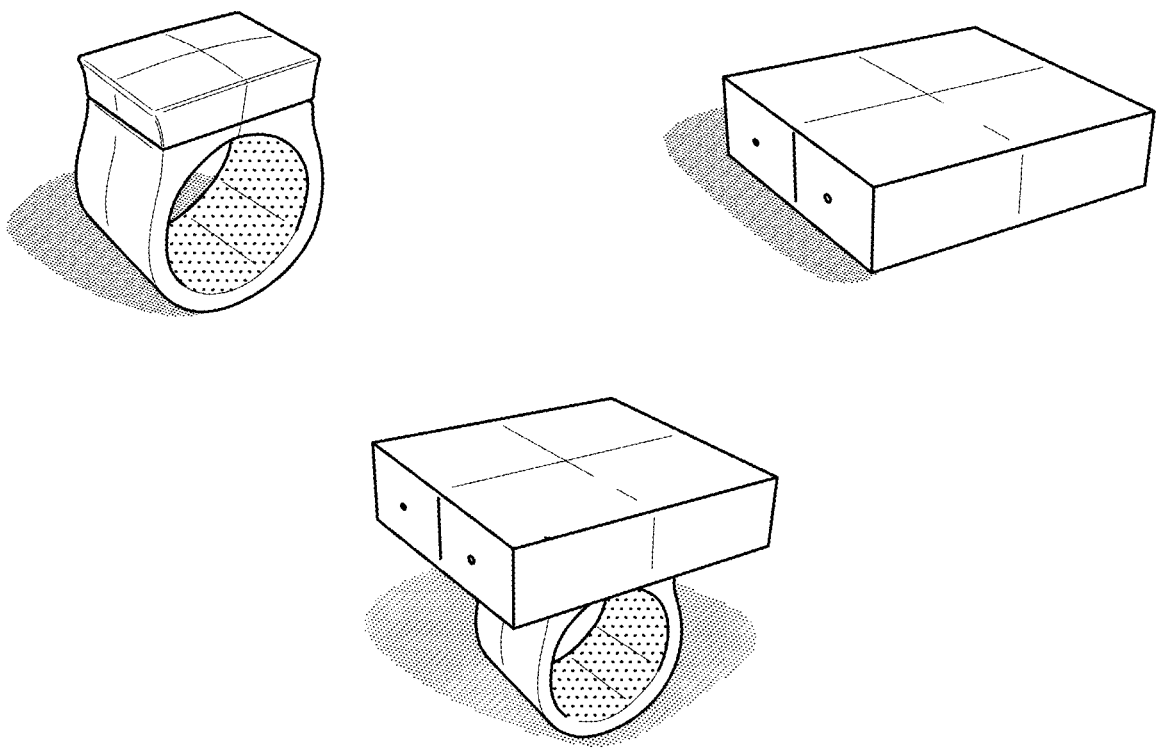
Figure 6D:
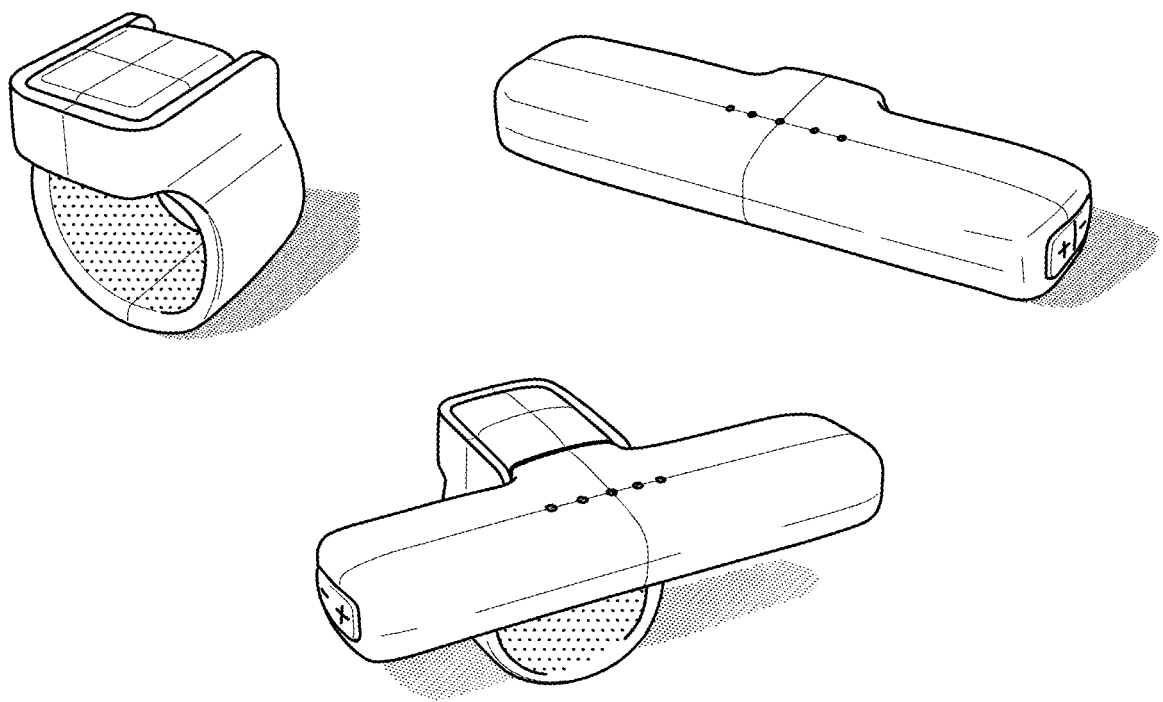

In one embodiment, the wearable monitor can have a GPS or similar device to track the location and assess activity of the wearer. GPS measures can be combined with mapping or location systems to determine context of the wearer's activity (e.g., gym versus office) or determine changes in elevation during specific activities, such as running or cycling. This may also be done by adding sensors to the wearable monitor such as barometers and altimeters In one embodiment, the ring and stimulation unit have a unique power charging station that can simultaneously charge both devices units. The charging station could have a custom direct electrical connection to the power source of the stimulation units or could charge the units inductively (e.g., wirelessly) in a close proximity (FIG. 5).

In one embodiment, the wearable monitor can track parameters about stimulation provided by the stimulation unit, including time of stimulation, duration of the stimulation session, and power used by the stimulation unit. This data can be stored on memory in the wearable monitor, processed by the wearable monitor, and/or transmitted to an external computing device, such as a smartphone, tablet, laptop, or desktop computer.

In some embodiments, the wearable monitor can communicate with an external computer or device (e.g., tablet, smartphone, smartwatch, or custom base station) to store data. Communication between the monitor and external device can be a direct, physical connection, or with a wireless communication connection such as Bluetooth, GSM, or cellular.

In some embodiments, the power source can be a rechargeable battery, which can be housed in the ring or stimulation unit, or can be used as a detachable power source that can be inserted into a port or receptacle in the ring or stimulation unit. Recharging the rechargeable battery can done through a wired connection or wirelessly.

In other embodiments, the power source can be a capacitor or a supercapacitor. Use of a capacitor may allow the size of the power source to be substantially reduced, which is important for a device that is designed to be worn on the finger. The capacitor can be recharged by an external power source through a wired connection or wirelessly (e.g., inductively). Recharging the capacitor can be performed between stimulations, during stimulations, or both.

It is understood that this disclosure, in many respects, is only illustrative of the numerous alternative device embodiments of the present invention. Changes may be made in the details, particularly in matters of shape, size, material and arrangement of various device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wearable ring device for treating hand tremors by electrically stimulating one or more sensory nerves on a finger of a patient's hand, the device comprising:
   an annular member defining an aperture that is sized to receive a finger of the patient;
   a first electrode, a second electrode, and a third electrode housed on an inside surface of the annular member and configured to be in contact with the patient's skin when worn on the finger; and
   a stimulation unit that is configured to connect to the annular member, wherein when the unit is connected to the annular member the unit is in electrical communication to the first electrode, the second electrode, and the third electrode, wherein the unit houses a power source and a pulse generator configured to deliver pulsed electrical stimulation to the one or more sensory nerves in the finger,
   wherein when worn the first electrode is configured to be positioned on the dorsal side of the finger, the second electrode is configured to be positioned on the palmar side of the finger, and the third electrode is configured to be positioned between the first and second electrodes.

2. The device of claim 1, wherein the third electrode is a common ground electrode.

3. The device of claim 1, wherein the finger is the index finger, middle finger, or the ringer finger.

4. The device of claim 1, further comprising a fourth electrode housed on the inside surface of the annular member.

5. The device of claim 1, wherein the power source is a capacitor.

6. The device of claim 1, wherein the power source is a rechargeable battery.

7. The device of claim 1, wherein the stimulation unit is detachable.

8. The device of claim 1, wherein the third electrode is configured to be positioned approximately equidistant between the first and second electrodes when the device is worn.

9. The device of claim 1, wherein the first, second, and third electrodes comprise a dry conductive polymer or rubber with a textured surface configured to capture moisture from the skin, air, or other external sources.

10. The device of claim 1, wherein the first, second, and third electrodes comprise a wicking conductive fabric configured to capture moisture from the skin, air, or other external sources.

11. The device of claim 1, further comprising a wireless transceiver electrically connected to the pulse generator and configured to communicate with at least one external electronic device.

12. The device of claim 1, wherein the annular member comprises a flexible housing material, and the first, second, and third electrodes are electrically connected with flexible electronic circuitry that is configured to conform to a predetermined range of finger diameters and configured to accommodate variation in finger diameter over time.

13. The device of claim 1, wherein the annular member comprises one or more motion sensors, and wherein the pulse generator is configured to modulate the pulsed electrical stimulation based on measurements of tremor motion and activity from the one or more motion sensors, wherein the one or more motion sensors are selected from the group consisting of an inertial measurement unit, an accelerometer, a gyroscope, and a magnetometer.

14. The device of claim 1, wherein the inside surface of the annular member is free from gels and adhesives.

15. The device of claim 1, further comprising a second annular member defining an aperture that is sized to receive the finger of the patient, wherein the second annular member comprises one or more motion sensors configured to measure motion of the patient's hand.

16. A wearable ring device for treating hand tremors by electrically stimulating one or more sensory nerves on a finger of a patient's hand, the device comprising:
   an annular member defining an aperture that is sized to receive a finger of the patient;
   a first electrode, a second electrode, and a third electrode housed on an inside surface of the annular member and configured to be in contact with the patient's skin when worn on the finger; and
   a stimulation unit that is configured to connect to the annular member, wherein when the unit is connected to the annular member the unit is in electrical communication to the first electrode, the second electrode, and the third electrode, wherein the unit houses a power source and a pulse generator configured to deliver pulsed electrical stimulation to the one or more sensory nerves in the finger,
   wherein the annular member comprises one or more motion sensors, and wherein the pulse generator is configured to modulate the pulsed electrical stimulation based on measurements of tremor motion and activity from the one or more motion sensors, wherein the one or more motion sensors are selected from the group consisting of an inertial measurement unit, an accelerometer, a gyroscope, and a magnetometer.

17. The device of claim 16, wherein the one or more motion sensors in the annular member along with a processor located in the stimulation unit or at least one external device are configured to measure and detect one or more predetermined motions and to modulate the pulsed electrical stimulation based on the measurement and detection of the one or more predetermined motions.

18. The device of claim 17, wherein one or more predetermined motions is selected from the group consisting of knocking the hand of the patient on an object a predetermined number of times, raising the arm up, waving the hand, opening and closing the hand, tapping the finger on a table a predetermined number of times, snapping the fingers, clapping of hands, and pointing.

19. A wearable ring device for treating hand tremors by electrically stimulating one or more sensory nerves on a finger of a patient's hand, the device comprising:
   an annular member defining an aperture that is sized to receive a finger of the patient;
   a first electrode, a second electrode, and a third electrode housed on an inside surface of the annular member and configured to be in contact with the patient's skin when worn on the finger;
   a stimulation unit that is configured to connect to the annular member, wherein when the unit is connected to the annular member the unit is in electrical communication to the first electrode, the second electrode, and the third electrode, wherein the unit houses a power source and a pulse generator configured to deliver pulsed electrical stimulation to the one or more sensory nerves in the finger; and
   a second annular member defining an aperture that is sized to receive the finger of the patient, wherein the second annular member comprises one or more motion sensors configured to measure motion of the patient's hand.

20. The device of claim 19, wherein the second annular member is configured to communicate with the stimulation unit and/or the at least one external device.

21. The device of claim 19, wherein the second annular member is configured to detachably connect to the stimulation unit.

* * * * *